United States Patent [19]
Terasawa et al.

[11] Patent Number: 5,658,920
[45] Date of Patent: Aug. 19, 1997

[54] SUBSTITUTED 1H,12H-BENZ-[DE]PYRANO [3',4':6,7] INDOLIZINO[1,2-B]QUINOLINE-10, 13(9H,15H)-DIONE COMPOUND

[75] Inventors: Hirofumi Terasawa, Sagamihara; Akio Ejima, Tokyo; Satoru Ohsuki, Ichihara; Kouichi Uoto, Tokyo, all of Japan

[73] Assignees: Daiichi Pharmaceutical Co., Ltd.; Kabushiki Kaisha Yakult Honsha, both of Tokyo, Japan

[21] Appl. No.: 455,706

[22] Filed: May 31, 1995

Related U.S. Application Data

[63] Continuation of Ser. No. 274,143, Jul. 14, 1994, abandoned, which is a continuation of Ser. No. 967,130, Oct. 27, 1992, abandoned, which is a continuation-in-part of Ser. No. 820,232, Jan. 14, 1992, abandoned.

[30] Foreign Application Priority Data

Jan. 16, 1991  [JP]  Japan ................................. 3-015812

[51] Int. Cl.$^6$ ................................................ A61K 31/47
[52] U.S. Cl. ................................................ 514/279; 546/41
[58] Field of Search ................................. 514/279; 546/41

[56] References Cited

U.S. PATENT DOCUMENTS

| 4,604,463 | 8/1986 | Miyasaku ................................. 314/361 |
| 4,939,255 | 7/1990 | Tagawa et al. ........................... 546/41 |
| 5,061,795 | 10/1991 | Tagawa et al. ........................... 540/578 |
| 5,340,817 | 8/1994 | Wall ......................................... 514/279 |

FOREIGN PATENT DOCUMENTS 0495432  7/1992  European Pat. Off. .

OTHER PUBLICATIONS

Burger, "Medicinal Chemistry, 2d Ed" Interscience NY, 1960 p. 42.
Patent Abstracts of Japan, vol. 14, No. 377(C-0748), Aug. 15, 1990, & JP-A-2-138186, May 28, 1990, A. Ejima, et al., "Camptothecin Relative Compound".
Kolata, N.Y.T. 26 Jul. 1994, p. C3.
Martin et al, Cancer Treatment Reports 68, 1317 (1984).
Gottlieb, Cancer Chemotherapy Reports 56, 103 (1972).
Moertel, Cancer Chemotherapy Reports 56, 95 (1972).
Estey, Cancer Treatment Reports 70, 1105 (1986).
Boven, Ed., "The nude mouse in Oncology Research" (1991) pp.305-316.
Dermer, Bio/Technology 12, p.320 (Mar. 1994).
Kawato, Anti. Microbial Agents and Chemotherapy 1991. p.192.
"84th Annual Meeting of the Am. Assoc. for Cancer Research", Poster #2510 (undated).
Schnur J. Med. Chem 34, 914 (1991).
Abstract for EP 296597.

*Primary Examiner*—Donald G. Daus
*Attorney, Agent, or Firm*—Oblon, Spivak, McClelland, Maier & Neustadt, P.C.

[57] ABSTRACT

A novel hexa-cyclic compound, a derivative of camptothecin, of the general formula:

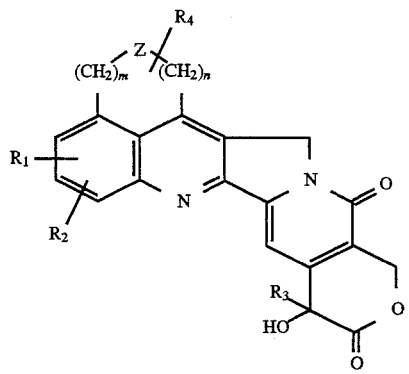

The compound is prepared from an aminoketone compound and a pyranoindolizine compound by the condensation-ring closing reaction. It is abundantly water-soluble, and has an excellent antitumor activity and a high degree of safety, and can be applied as an antitumor medicine for curing tumors of various kinds.

3 Claims, No Drawings

SUBSTITUTED 1H,12H-BENZ-[DE]PYRANO [3',4':6,7] INDOLIZINO[1,2-B]QUINOLINE-10, 13(9H,15H)-DIONE COMPOUND

This application is a Continuation of application Ser. No. 08/274,143, filed on Jul. 14, 1994, abandoned, which is a Continuation of Ser. No. 07/967,130, filed on Oct. 27, 1992, abandoned, which is a Continuation-in-Part of Ser. No. 07/820,232, filed on Jan. 14, 1992, abandoned.

FIELD OF THE INVENTION

This invention relates to a novel compound having an antitumor activity and a process for preparing this compound.

DESCRIPTION OF THE BACKGROUND

Camptothecin is a penta-cyclic alkaloid isolated from barks, roots, fruits, or leaves of camptotheca acuminata. This compound is known to exhibit an antitumor activity because of its capability of inhibiting nucleic acid synthesis. According to the results of clinical tests conducted in the United States, however, the compound was found to have a problem in view of safety, and its research and development as a medicine have been discontinued. Thereafter, research on derivatives of camptothecin possessing better activity and reduced toxicity has been undertaken worldwide. However, no report has surfaced so far on the derivative with satisfactory clinical results.

The scarce solubility of camptothecin in water is another problem of this compound in administering it as a medicine. A method of opening the lactone ring and converting it into the sodium carbonate is known as one of the means for making camptothecin water-soluble. The product obtained by this method, however, exhibits a very reduced antitumor activity. The development of a water-soluble camptothecin derivative with the lactone ring being retained as is has therefore been desired.

The present inventors have conducted extensive studies for the purpose of obtaining camptothecin derivatives with more excellent activity and higher safety, as well as excellent characteristics required for a drug to be administered, and found that hexa-cyclic compounds obtained by the addition of a water-soluble ring to camptothecin had characteristics superior to camptothecin. This finding has led to the completion of this invention.

SUMMARY OF THE INVENTION

Accordingly, an object of this invention is to provide a hexa-cyclic compound represented by the following general formula:

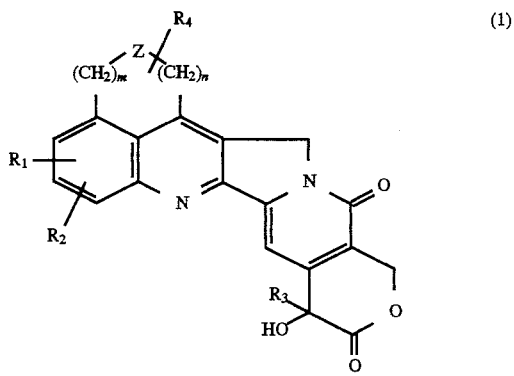

(1)

wherein $R_1$ and $R_2$ individually represent a hydrogen atom, a hydroxyl group, a $C_{1-6}$ alkyl group ("$C_{1-6}$ alkyl group means an alkyl group having 1 to 6 carbon atoms. Hereinafter defined in the same manner.) which may contain a halogen manner.) which may contain a halogen atom, a nitro or cyano group, a $C_{1-6}$ alkenyl group, a $C_{1-6}$ alkynyl group, a $C_{1-6}$ alkoxyl group, a $C_{1-6}$ aminoalkoxyl group, a halogen atom, a nitro group, a cyano group, a mercapto group, a alkylthio group, an amino group which may contain a protective group, a $C_{1-6}$ aminoalkyl groups which may contain a protective group or a $C_{1-6}$ alkyl group at the amino-position, a $C_{1-6}$ aminoalkylamino group which may contain a protective group or a $C_{1-6}$ alkyl group at the amino-position, a $C_{1-6}$ alkyl group with a heterocyclic ring which may contain a $C_{1-6}$ alkyl, $C_{1-6}$ alkoxyl, amino, halogeno, nitro, or cyano group, a carbonyl with a heterocyclic ring which may contain a $C_{1-6}$ alkyl, $C_{1-6}$ alkoxyl, amino, halogeno, nitro, or cyano group, a $C_{1-6}$ alkylamino group with a heterocyclic ring which may contain $C_{1-6}$ alkyl, $C_{1-6}$ alkoxyl, amino (which may contain a protective group), halogeno, nitro, cyano or a protective group, an amino-heterocyclic group which may contain a protective group or a $C_{1-6}$ alkyl group at the nitrogen atom of the heterocyclic ring moiety or at the amino position, a heterocyclic-amino group which may contain a protective group or a $C_{1-6}$ alkyl group at the nitrogen atom of the heterocyclic ring moiety or at the amino position, or a carbamoyl group which may contain a protective group or a $C_{1-6}$ alkyl group; $R_3$ represents a $C_{1-6}$ alkyl group; $R_4$ represents an amino group which may contain a protective group, a quaternary trialkyl ammonium such as $—N^+(CH_3)_3$, a $C_{1-6}$ alkylamino group which may contain a protective group, a $C_{1-6}$ aminoalkyl group which may contain a protective group, a $C_{1-6}$ alkylaminoalkyl group which may contain a protective group, a sulfonic acid group, or a carboxyl group; Z represents an oxygen atom, a sulfur atom, $CR_5R_6$, wherein $R_5$ and $R_6$ individually represent a hydrogen atom or a $C_{1-6}$ alkyl, or N—$R_7$, wherein $R_7$ stands for a hydrogen atom, a $C_{1-6}$ alkyl group, a $C_{1-6}$ aminoalkyl group which may contain a protective group, a $C_{1-6}$ aminoalkyl group which may contain a protective group, a $C_{1-6}$ alkylaminoalkyl group which may contain a protective group, or a protective group for the amino group; and m and n individually represent 0, 1 or 2.

Other objects, features and advantages of the invention will hereinafter become more readily apparent from the following description.

DETAILED DESCRIPTION OF THE INVENTION AND PREFERRED EMBODIMENTS

Preferred examples of groups represented by $R_1$ or $R_2$ in formula (I) are $C_{1-3}$ alkyl, $C_{1-3}$ alkenyl, hydroxymethyl, hydroxyl, $C_{1-3}$ alkoxyl, halogen, nitro, amino, $C_{1-3}$ alkylamino, cyano-$C_{1-3}$ alkyl, aminomethyl, dimethylhydrazino, morphorine-1-yl, piperidine-1-yl, and the like.

Ethyl group and the like are given as preferable groups for $R_3$.

Amino group, $C_{1-6}$ alkylamino, amino-$C_{1-6}$ alkyl, $C_{1-6}$ alkylamino-$C_{1-6}$ alkyl groups are given as preferred groups for $R_4$. Among these, especially preferable are methylamino, dimethylamino, aminomethyl, ethylamino, diethylamino, aminoethyl, methylaminomethyl, dimethylaminomethyl, hydroxy ethylamino and the like.

When substituent $R_4$ and substituent $R_1$ or $R_2$ of compound (I) are suitably selected, the compound possesses sufficient water-solubility and a suitable degree of lipophilicity, and thus exhibits excellent properties. The lipophilicity is a parameter of cell membrane permeability of the compound, and the improved cell membrane permeability promises cytotoxicity against cacerous cells.

Examples of preferable combination of $R_4$, $R_1$ and $R_2$ include such that:

$R_4$ is $NH_2$, $NHCH_3$ or $N(CH_3)_2$, and $R_1$ or $R_2$ is $CH_3$ or $C_2H_5$ Among them, most preferred is a combination where $R_4$ is $NH_2$, $R_1$ is 4-methyl and $R_5$ is 5-fluoro.

When $R_4$ is $NH_2$, and $R_1$ or $R_2$ is OH, only an insufficient cell mimbrane permeability is obtained, and therefore, it is prererred that the compound be converted to a pro-drug, in other words, the OH group is converted to —O—Y or —O—CO—Y. Here, Y is amino, dialkylamino, dialkylaminoalkylamino, aminoalkyl, alkylaminoalkyl, dialkylaminoalkyl, heterocyclic group which may contain one or more $C_{1-6}$ alkyl, $C_{1-6}$ alkoxyl, amino, halogeno, nitro or cyano group, or alkyl troup with heterocyclic ring which may contain one or more $C_{1-6}$ alkyl, $C_{1-6}$ alkoxyl, amino, halogeno, nitro or cyano groups.

A quaternary trialkyl ammonium such as —$N^+(CH_3)_3$ is also priferred as $R_4$.

Methylene group, oxygen atom, sulfur atom, imino(—NH—), alkylimino(—N(alkyl)—), and the like are given as preferable groups represented by Z.

As preferred protective groups for amino group, given are formyl, acetyl, trithyl, tert-butoxycarbonyl, benzyl, p-methoxybenzyloxycarbonyl, and the like.

Given as preferred examples for heterocyclic groups are 4–7 membered rings having one or more nitrogen atoms which may contain one or more oxygen atoms or sulfur atoms, such as azetidine, piperazine, morpholine, pyrrolidine, piperidine, imiazole, thiazole, oxazole, pyridine, and the like. Among them, those having 5 or 6 membered rings such as pyrrolidine, piperidine, piperazine, morpholine and the like are especially preferred.

Among the compounds of formula (I), those having a six-membered ring for the A-ring, which are represented by the following formula (IA) is particularly preferable.

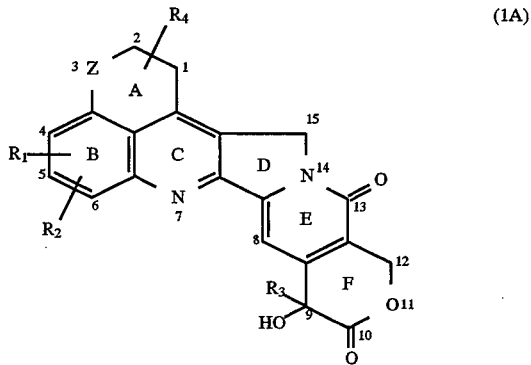

(IA)

Furthermore, among the compounds of formula (I), those in which the asymmetric carbon at 9 position of the F-ring takes the S-type configuration are preferable from the aspect of medicinal activity.

The compounds of the present invention can be prepared according to the process exemplified by the following reaction scheme.

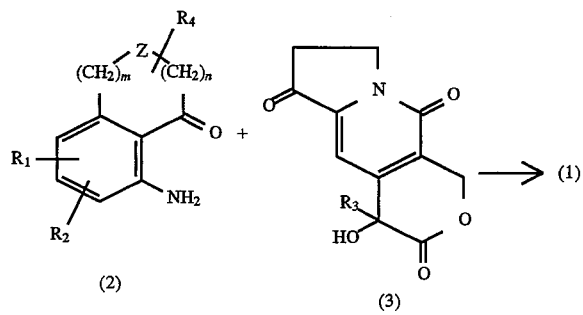

According to the above process scheme, an aminoketone compound (2) and a pyranoindolizine compound (3) are condensed by the Friedlaender reaction to produce the compound (I).

Aminoketone compounds (2) are known compounds and can be readily prepared according to the methods known in the art. The conditions of this condensation ring-closing reaction of compounds (2) and (3) can be suitably selected from the conditions, wherein the reaction is conducted at room temperature or an elevated temperature in the presence of an acid or a base.

There is no specific limitation to the kind of the solvent used, so long as the solvent is inert to the reaction. Examples of such solvents include aromatic hydrocarbons such as benzene, toluene, xylene, and the like, halogenated hydrocarbons such as dichloromethane, chloroform, 1,2-dichloroethane, and the like, ethers such as diethyl ether, diisopropyl ether, tetrahydrofuran, dimethyl cellosolve, diethyl cellosolve, diglyme, and the like, lower alcohols such as methanol, ethanol, propanol, tert-butanol, and the like, amides such as acetamide, dimethylacetamide, N,N-dimethylformamide, and the like, and acetic acid. Particularly preferable solvents are benzene, toluene, and acetic acid.

Either an organic acid or inorganic acid can be used for the reaction. Hydrochloric acid and sulfuric acid are typical examples given of inorganic acids. Organic acids which can be used include sulfonic acids such as methanesulfonic acid, trifluoromethanesulfonic acid, benzenesulfonic acid, p-toluenesulfonic acid, pyridine-p-toluene sulfonate; carboxylic acids such as acetic acid; and the like. Among these especially preferable are p-toluenesulfonic acid, pyridine-p-toluene sulfonate, acetic acid, and the like. Here, acetic acid can function also as a solvent.

A base to be employed in the reaction may be either an inorganic-or organic base. Given as examples of inorganic bases are hydroxides, carbonates, bicarbonates, and hydrides of alkali metal such as lithium hydroxide, sodium hydroxide, potassium hydroxide, lithium carbonate, sodium carbonate, potassium carbonate, sodium bicarbonate, potassium bicarbonate, sodium hydride, and the like. Organic bases include alkoxide of alkali metal such as sodium methoxide, sodium ethoxide, potassium tert-butoxide, and the like; tert-alkyl amines such as triethylamine, N,N-diisopropylethylamine, and the like; aromatic tertiary amines such as N,N-dimethylaniline, N,N-diethylaniline, N,N-dimethylaminopyridine, and the like; pyridine; 1,8-diazabicycloundecene; and the like. Preferred bases are potassium carbonate and triethylamine.

Some compounds of formula (3) are unstable against basic compounds. Deliberate considerations therefore must be given to the reaction conditions when a base is used. For example, measures must be taken such as carrying out the reaction at a relatively low temperature, for a shorter period of time, or under acidic conditions.

The reaction is carried out at a temperature usually of 20°–150° C. and preferably 80°–120° C. Depending on the characteristics of compound (3), however, the reaction under ice-cooling is desirable. The reaction time may be between 1 hour and 48 hours. Usually, the reaction is completed within 1–24 hours.

A typical example of performing the reaction is refluxing the reaction mixture in benzene, toluene, or acetic acid in the presence of pyridine p-toluenesulfonate.

When a group $R_1$, $R_2$, or $R_4$, or their substituent is an amino group with a protective group, such a protective group can be removed by the reduction or hydrolysis with an acid or alkali.

A compounds having an alkoxyl group can be converted into the corresponding hydroxyl compounds by treating them with aluminum chloride or aluminum bromide in an inert solvent such as toluene, benzene, or the like, or by heating in a solution of hydrobromic acid.

A compound having a nitro group can be converted into the corresponding amino compound by catalytic reduction using platinum, palladium, or the like.

A compound having an amino group can be converted into the corresponding hydroxyl compound via a diazonium compound by the treatment with sodium nitrite or the like in an acidic solvent at a low temperature, followed by hydrolysis of the diazonium salt.

A compound having an amino group can also be converted into the corresponding halogeno compound by the Sandmeyer reaction via diazonium salt mentioned above. General Sandmeyer reaction conditions can be applicable to this reaction using cuprous chloride, cuprous bromide, or the like.

The compound of this invention can optionally be converted into a form of physiologically acceptable salt, e.g., a salt of an alkali metal or alkali earth metal, by using a hydroxide of these metals; or when such a compound is a basic compound such as that possessing an amino group or the like, may be converted into an inorganic or organic salt using an inorganic acid such as hydrochloric acid, sulfuric acid, phosphoric acid, or the like, or an organic acid such as formic acid, acetic acid, methanesulfonic acid or the like.

Antitumor effects of the compound of this invention thus prepared are hereinafter described by way of experimental examples.

EXPERIMENTAL EXAMPLE 1

P388 murine leukemia cells were spread over a 96-well microplate, 2.5×10³ cells per well. A sample to be tested was added after 24 hours. Cells were cultivated under the conditions of 5% $CO_2$ at 37° C. for 3 days. 3-(4,5-Dimethylthiazol-2-yl)-2,5-diphenyl-2H-tetrazolium bromide (MTT) was added 4 hours after the addition of the sample. Upon the addition of 200 µl/ml of isopropyl alcohol containing 0.04N HCl the absorption at 540 nm was measured to determine $IC_{50}$.

The results are shown in Table 1.

TABLE 1

| | $IC_{50}$ (ng/ml) |
|---|---|
| Compound of Example 2 (Isomer A) | 3.38 |
| Compound of Example 2 (Isomer B) | 12.40 |
| Compound of Example 4 (Isomer A) | 9.21 |

TABLE 1-continued

| | $IC_{50}$ (ng/ml) |
|---|---|
| Compound of Example 4 (Isomer B) | 27.80 |
| Compound of Example 7 (Isomer A) | 11.40 |
| Compound of Example 7 (Isomer B) | 11.90 |

As shown in Table 1, the compounds of this invention have an excellent antitumor activity and a high degree of safety, and are water-soluble. They are useful as an antitumor medicine.

Other features of the invention will become apparent in the course of the following description of the exemplary embodiments which are given for illustration of the invention and are not intended to be limiting thereof.

EXAMPLES

Example 1

Preparation of (9S)-1-acetylamino-9-ethyl-2,3-dihydro-9-hydroxy-1H,12H-benzo[de]pyrano[3',4':6,7]indolizino[1,2-b]-quinoline-10,13(9H,15H)-dione

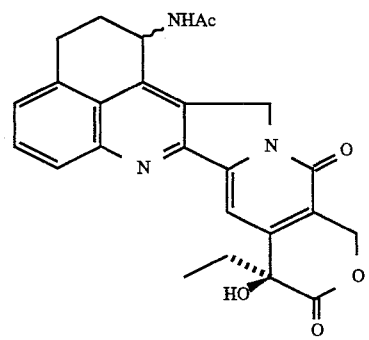

(1) 8-Acetylamino-1-tetralone 10 gm of 1-acetylamino-tetraline was dissolved into a mixed solvent of 400 ml acetone and 40 ml of 15% aqueous solution of magnesium sulfate. The solution was kept at 0° C. to add 42 gm of potassium permanganate, followed by stirring for 20 minutes at the same temperature. 800 ml of water was added to the residue obtained by concentrating the solvent. Precipitates thus obtained was extracted with chloroform and the extract was washed with brine and dried over magnesium sulfate. The residue obtained by the concentration of the solvent was subjected to silica gel column chromatography using chloroform as an eluant to obtain fractions containing the target compound. The fractions were concentrated to produce 5.46 gm of the title compound.

NMR(CDCl₃)δ: 2.08–2.14(2H, m), 2.23(3H, s), 2.70(2H, t,J=6.8 Hz), 2.97(2H, t, J=6.8 Hz), 6.93(1H, d, J=6.8 Hz), 7.44(1H, t, J=8.3 Hz), 8.59(1H, d, J=8.3 Hz)

(2) 8-Acetylamino-2-hydroxyimino-1-tetralone

To a reaction solution obtained by suspending 316 mg of potassium tert-butoxide in 18 ml of tetrahydrofuran (hereinafter abbreviated as THF) and cooling the suspension to 0° C. under a nitrogen stream was added a solution of 500 mg of the compound prepared in (1) above in 2 ml of THF, a bit at a time. After stirring for 10 minutes at the same temperature and an addition of 0.35 ml of butyl nitrite, the mixture was heated at 50° C. for 1 hour while stirring. Precipitates obtained by the addition of diethyl ether to the reaction mixture were collected by filtration. The powder thus obtained was suspended into a 10% aqueous solution of hydrochloric acid and extracted with ethyl acetate. The extract was washed with brine and dried over magnesium sulfate. The residue obtained by the concentration of the solvent was subjected to silica gel column chromatography using an ethyl acetate-hexane (1:1) mixed solvent as an eluant to obtain fractions containing the target compound. The fractions were concentrated to produce 320 mg of the title compound.

IRv$_{max}^{KBr}$ cm$^{-1}$: 3440, 1698, 1678, 1608, 1580, 1518. NMR(CDCl$_3$)δ: 2.26(3H, s), 3.08(4H, s), 6.98(1H, d, J=7.4 Hz),7.53(1H, t, J=7.7 Hz), 8.64(1H, d, J=8.5 Hz). MASS m/z: 232 (M$^+$)

(3) 2,8-Diacetylamino-1-tetralone 1 gm of zinc powder was added to a solution of 300 mg of the compound prepared in (2) above dissolved in a mixed solvent of 10 ml of acetic acid and 10 ml of acetic anhydride, and the mixture was stirred for 40 minutes at room temperature. Insoluble substances were removed by filtration and filtrate was concentrated. The residue was recrystallized in ethyl acetate and hexane to obtain 263 mg of the title compound.

IRv$_{max}^{KBr}$ cm$^{-1}$: 3280, 1660, 1596, 1516. NMR(CDCl$_3$) δ: 1.6–2.0(1H, m), 2.11(3H, s), 2.23(3H, s), 2.6–3.0(1H, m), 3.1–3.4(2H, m), 4.6–4.8(1H, m) 6.93(1H, d, J=6.8 Hz), 7.49(1H, t, J=8.3 Hz), 8.59(1H, d, J=8.3 Hz). MASS m/z: 260(M$^+$)

(4) 2-Acetylamino-8-amino-1-tetralone 245 mg of the compound prepared in (3) above was dissolved into 40 ml of 3N hydrochloric acid and heated at 60° C. for 1 hour while stirring. After cooling to 0° C., the reaction solution was neutralized with sodium carbonate and extracted with chloroform. The extract was dried over magnesium sulfate. The residue obtained after the removal of the solvent was recrystallized in ethyl acetate and hexane to obtain 150 mg of the title compound.

IRv$_{max}^{KBr}$ cm$^{-1}$: 3424, 3304, 1668, 1632, 1558, 1508. NMR(CDCl$_3$)δ: 1.6–2.0(1H, m), 2.09(3H, s), 2.6–3.2(3H, m), 4.41–4.67(1H, m), 6.47–6.71(2H, m), 7.12–7.26(1H, m). MASS m/z: 218(M$^+$)

(5) (9S)-1-Acetylamino-9-ethyl-2,3-dihydro-9-hydroxy-1H,12H-benzo[de]pyrano[3',4':6,7]indolizino[1,2-b]quinoline-10,13-(9H,15H)-dione 361 mg of (S)-4-ethyl-4-hydroxy-7,8-dihydro-1H-pyrano-[3,4-f]indolizine-3,6,10(4H)-trione (hereinafter abbreviated as "trione") was added to the solution of 300 mg of the compound prepared in (4) above in 200 ml of toluene. The mixture was heated under reflux using a Deanstark apparatus for 10 minutes. To the mixture was added 1 mg of pyridinium-p-toluenesulfonate (hereinafter abbreviated as "PPTS") and the mixture was refluxed while stirring for a further 24 hours. After cooling, the residue obtained by removing toluene by concentration was suspended into 300 ml of chloroform-methanol (10:1) solvent. Insoluble substances were removed and the residue was powdered with methanol to obtain 336 mg of the title compound.

mp: above 240° C. (decomposed). IRv$_{max}^{KBr}$ cm$^{-1}$: 3452, 1750, 1660. NMR(DMSO-d$_6$)δ: 0.89(3H, t, J=7.2 Hz), 1.83–1.92(2H, m), 1.94(3H, d, J=4 Hz), 2.09–2.17(2H, m), 3.14–3.31(2H, m), 5.21(2H, d, J=5.6 Hz), 5.42(2H, d, J=5.6 Hz), 5.58–5.61(1H, d), 6.50(1H, br s), 7.35(1H, d, J=2.4 Hz), 7.52(1H, d, J=7.2 Hz), 7.79(1H, t, J=7.2 Hz), 8.02(1H, d, J=8.7 Hz), 8.52(1H, t, J=9.5 Hz). MASS m/z: 445 (M$^+$)

Example 2

Preparation of (9S)-1-amino-9-ethyl-2,3-dihydro-9-hydroxy-1H,12H-benzo[de]pyrano[3',4':6,7]indolizino[1,2-b]quinoline-10,13(9H,15H)-dione Hydrochloride

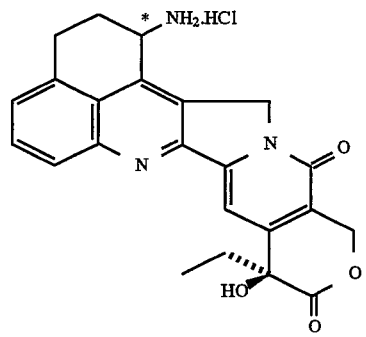

A mixture obtained by the addition of 300 mg of the compound prepared in Example 1 to 100 ml of 6N aqueous solution of hydrochloric acid was reacted under reflux for 4 hours. After having been allowed to cool, the reaction mixture was concentrated. 100 ml of water was added to the residue to remove insoluble substance by filtration using FALCON 7105 (0.22 μm). The residue obtained by concentrating the filtrate was purified with reverse HPLC (CAPCELL PAK C18: trademark, manufactured by Shiseido Co.) using a mixture of acetonitrile-water-1N hydrochloric acid (20:80:2) to separate two kinds of diasteroisomers. The residue obtained by concentrating the fraction first eluted was precipitated in methanol and acetonitrile to obtain 74 mg of the title compound (Isomer A). In the same manner, 90 mg of the title compound (Isomer B) was obtained from the fraction next eluted. In the following Examples, isomers first eluted from the reverse HPLC are designated as Isomer A and second eluted as Isomer B.

Isomer A mp: above 240° C. (decomposed). [α]$_D^{20}$=+178° (c=0.25, in H$_2$O). IRv$_{max}^{KBr}$ cm$^{-1}$: 3440, 1738, 1658. NMR(DMSO-d$_6$)δ: 0.90(3H, t, J=7.2 Hz), 1.85–194(2H, m), 2.17–2.23 (1H, m), 3.20–3.23(1H, m), 3.36–3.43(1H, m), 5.12(1H, br s), 5.42–5.46(3H, m), 5.94(1H, d, J=19 Hz), 6.53(1H, s), 7.38(1H, s), 7.61(1H, d, J=7.2 Hz), 7.85(1H, t, J=7.2 Hz), 8.09(1H, d, J=8.8 Hz), 8.77(3H, br). MASS m/z: 403(M$^+$)

Isomer B mp: above 240° C. (decomposed). [α]$_D^{20}$=−38° (c=0.25, in H$_2$O). IRv$_{max}^{KBr}$ cm$^{-1}$: 3444, 1740, 1658. NMR(DMSO-d$_6$)δ: 0.89(3H, t, J=7.2 Hz), 1.84–1.93(2H, m), 2.16–2.23 (1H, m), 3.21–3.24(1H, m), 3.38–3.45(1H, m), 5.13(1H, br s), 5.42–5.49(3H, m), 5.98(1H, d, J=19 Hz), 7.38(1H, s), 7.61(1H, d, J=7.2 Hz), 7.86(1H, t, J=7.2 Hz), 8.09(1H, d, J=8.8 Hz), 8.77(3H, br). MASS m/z: 403(M$^+$)

Example 3

Preparation of (9S)-1-acetylamino-9-ethyl-2,3-dihydro-9-hydroxy-4-methoxy-1H,12H-benzo[de]pyrano[3',4':6,7]indolizino[1,2-b]quinoline-10,13(9H,15H)-dione

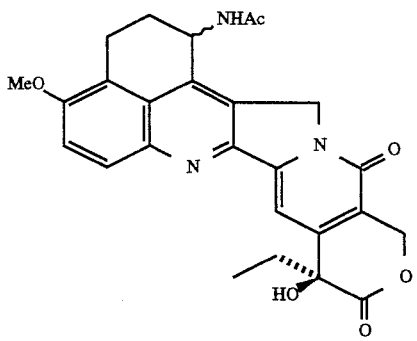

(1) 2-Hydroxyimino-5-methoxy-8-nitro-1-tetralone

The same procedure as in Example 1-(2) was carried out, except that 1.5 gm of 5-methoxy-8-nitro-1-tetralone was used instead of 8-acetylamino-1-tetralone. Upon the post-treatment in the same manner as in Example 1-(2), 740 mg of the title compound was obtained.

IR$\nu_{max}^{KBr}$ cm$^{-1}$: 3428, 3256, 1696, 1604, 1580, 1534. NMR(DMSO-d$_6$)δ: 2.95(4H, s), 3.94(3H, s), 7.32(1H, d, J=8.7 Hz), 7.78(1H, d, J=8.7 Hz). MASS m/z: 251(M$^+$)

(2) 2,8-Diacetylamino-5-methoxy-1-tetralone

The same procedure as in Example 1-(3) was carried out, except that 500 mg of the compound prepared in (1) above was used instead of 8-acetylamino-2-hydroxyimino-1-tetralone. Upon the post-treatment in the same manner as in Example 1-(3), 225 mg of the title compound was obtained.

IR$\nu_{max}^{KBr}$ cm$^{-1}$: 3432, 1696, 1642, 1532. NMR(CDCl$_3$) δ: 1.6–2.0(1H, m), 2.11(3H, s), 2.21(3H, s), 2.6–3.2(3H, m), 3.85(3H, s), 4.5–4.8(1H, m), 7.09(1H, d, J=9.2 Hz), 8.55 (1H, d, J=9.2 Hz). MASS m/z: 290(M$^+$)

(3) 2-Acetylamino-8-amino-5-methoxy-1-tetralone

The same procedure as in Example 1-(4) was carried out, except that 200 mg of the compound prepared in (2) above was used instead of 2,8-diacetylamino-1-tetralone. Upon the post-treatment in the same manner as in Example 1-(4), 130 mg of the title compound was obtained.

IR$\nu_{max}^{KBr}$ cm$^{-1}$: 3444, 2940, 1632, 1564, 1534. NMR (CDCl$_3$)δ: 1.6–2.0(1H, m), 2.08(3H, s), 2.6–3.4(3H, m), 3.77(3H, s), 4.52–4.61(1H, m), 6.52(1H, d, J=9.2 Hz), 6.98(1H, d, J=9.2 Hz). MASS m/z: 248(M$^+$)

(4) (9S)-1-Acetylamino-9-ethyl-2,3-dihydro-9-hydroxy-4-methoxy-1H,12H-benzo[de]pyrano[3',4':6,7]indolizino[1,2-b]quinoline-10,13(9H,15H)-dione 125 mg of the compound prepared in (3) above was reacted with 133 mg of trione for 24 hours in the same manner as in Example 1-(5). Upon the post-treatment in the same manner as in Example 1-(5), 207 mg of the title compound was obtained.

mp: above 240° C. (decomposed). IR$\nu_{max}^{KBr}$ cm$^{-1}$: 3448, 1748, 1660, 1600. NMR(DMSO-d$_6$)δ: 0.88(3H, dt, J=3.2, 7.2 Hz), 1.84–1.89(2H, m), 1.92(3H, d, J=4.8 Hz), 2.06–2.07(2H, m), 3.07–3.08(2H, m), 4.00(3H, s), 5.20(2H, d, J=4.8 Hz), 5.41(2H, d, J=4.8 Hz), 5.52–5.54 (1H, m), 6.48(1H, d, J=1.6 Hz), 7.28(1H, d, J=2.4 Hz), 7.77(1H, d, J=9.5 Hz), 8.08(1H, d, J=9.5 Hz), 8.44(1H, t, J=9.5 Hz). MASS m/z: 475(M$^+$)

Example 4

Preparation of (9S)-1-amino-9-ethyl-2,3-dihydro-9-hydroxy-4-methoxy-1H,12H-benzo[de]pyrano[3',4':6,7]indolizino[1,2-b]quinoline-10,13(9H,15H)-dione Hydrochloride

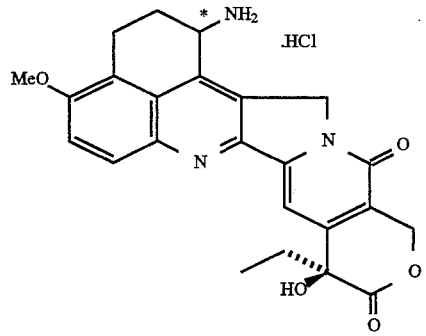

102 mg of the compound prepared in Example 3-(4) was reacted and post-treated in the same manner as in Example 2 to obtain 50 mg of Isomer A and 44 mg of Isomer B of the title compound.

Isomer A.

mp: above 240° (decomposed). $[\alpha]_D^{20}$=+78° (c=0.25, in H$_2$O). IR$\nu_{max}^{KBr}$ cm$^{-1}$: 3448, 2936, 1740, 1658, 1598. NMR(DMSO-d$_6$)δ: 0.90(3H, t, J=7.2 Hz), 1.84–1.93(2H, m), 2.07–2.12(1H, m), 2.94–3.00(1H, m), 3.25–3.33(1H, m), 4.03(3H, s), 5.07(1H, br), 5.40–5.44(3H, m), 5.91(1H, d, J=19 Hz), 7.32(1H, s), 7.83(1H, d, J=9.5 Hz), 8.15(1H, d, J=8.8 Hz), 8.75(3H, br). MASS m/z: 433(M$^+$)

Isomer B mp: above 240° C. (decomposed). $[\alpha]_D^{20}$=−34° (c=0.25, in H$_2$O). IR$\nu_{max}^{KBr}$ cm$^{-1}$: 3448, 1744, 1654. NMR(DMSO-d$_6$)δ: 0.89(3H, t, J=7.2 Hz), 1.84–1.91(2H, m), 2.06–2.12 (1H, m), 2.95–3.01(1H, m), 4.03(3H, s), 5.07(1H, br), 5.41–5.44(3H, br s), 5.93(1H, d, J=19 Hz), 7.32(1H, s), 7.84(1H, d, J=9.5 Hz), 8.16(1H, d, J=8.8 Hz), 8.78(3H, br). MASS m/z: 433(M$^+$)

Example 5

Preparation of (9S)-1-amino-9-ethyl-2,3-dihydro-4,9-dihydroxy-1H,12H-benzo[de]pyrano[3',4':6,7]indolizino[1,2-b]quinoline-10,13(9H,15H)-dione Hydrochloride

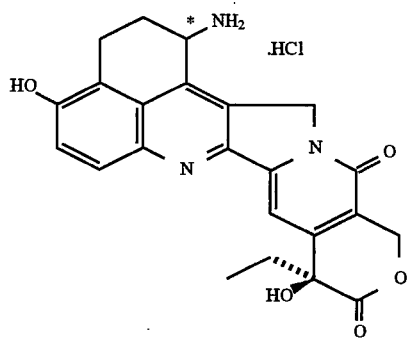

90 mg of the compound prepared in Example 3-(4) was added to 30 ml of 47% aqueous solution of hydrobromic acid and the mixture was heated under reflux for 3 hours. To the residue obtained by removing solvent under reduced pressure 30 ml of water was added. Insoluble substances were removed by filtration using FALCON 7105 (0.22 μm). The residue obtained by concentrating the filtrate was purified with reverse HPLC (CAPCELL PAK C18: trademark, manufactured by Shiseido Co.) using a mixture of acetonitrile-water-1N hydrochloric acid (20:80:2) to obtain 34 mg of Isomer A and 35 mg of Isomer B of the title compound.

Isomer A mp: above 240° C. (decomposed). $[\alpha]_D^{20}$=+135° (c=0.25, in $H_2O$). NMR(DMSO-$d_6$)δ: 0.89(3H, t, J=7.2 Hz), 1.83–1.92(2H, m), 2.04–2.09(1H, m), 2.88–2.95(1H, m), 3.20–3.24(1H, m), 5.04(1H, br), 5.43(3H, m) 5.89(1H, d, J=19 Hz), 7.29(1H, s), 7.61(1H, d, J=8.7 Hz), 7.99(1H, d, J=9.5 Hz), 8.71(3H, br), 10.5(1H, br). MASS m/z: 419($M^+$)

Isomer B mp: above 240° C. (decomposed). $[\alpha]_D^{20}$=-6.0° (c=0.2, in $H_2O$). NMR(DMSO-$d_6$)δ: 0.89(3H, t, J=7.2 Hz), 1.84–1.91(2H, m), 2.07–2.09(1H, m), 2.88–2.95(1H, m), 3.21–3.24(1H, m), 5.05(1H, br), 5.39–5.47(3H, m), 5.88 (1H, d, J=19 Hz), 7.29(1H, s), 7.61(1H, d, J=8.7 Hz), 7.98(1H, d, J=8.7 Hz), 8.68(3H, br), 10.5(1H, br). MASS m/z: 419($M^+$)

Example 6

Preparation of (9S)-9-ethyl-2,3-dihydro-9-hydroxy-4-methoxy-3-(1,3-dioxoisoindolin-2-yl)-1H,12H-benzo[de]pyrano[3',4':6,7]indolizino[1,2-b]quinoline-10,13(9H,15H)-dione

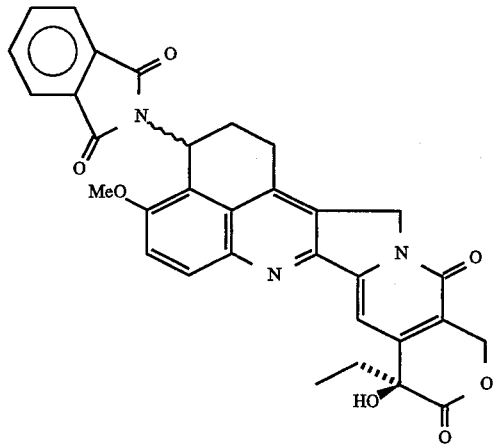

(1) 4-Hydroxy-5-methoxy-8-nitro-1-tetralone 2.0 gm of 5-methoxy-8-nitro-1-tetralone (described in Japanese Patent Laid-open (ko-kai) 279891/1989) and 2.05 gm of N-bromosuccinic imide were dissolved in 50 ml of carbon tetrachloride. After the addition of a catalytic amount of benzoyl peroxide, the mixture was heated under reflux for 4 hours and then cooled to room temperature, followed by the addition of 50 ml of chloroform. The mixture was washed with 10% aqueous solution of sodium hydroxide, water, and saturated brine in this order, and dried over anhydrous sodium sulfate. To the residue obtained by removing the solvent were added 5 ml of tetrahydrofuran, 5 ml of ethanol, 8 ml of water, and 250 mg of calcium carbonate, and the mixture was heated under reflux. A residue was obtained by removing the solvent from the reaction mixture, which, after the addition of 50 ml of water, was extracted with chloroform. The extract was washed with saturated brine, dried over anhydrous sodium sulfate, and subjected to silica gel column chromatography using chloroform-ethyl acetate. (4:1) as an eluant to obtain fractions containing the target compound. The fractions were concentrated to produce 1.49 gm of light yellow powder of the title compound.

NMR(CDCl$_3$)δ: 2.2–2.4(2H, m), 2.5–2.7(2H, m), 3.0–3.2 (1H, m), 4.00(3H, s), 5.29(1H, s), 7.09(1H, d, J=8.8 Hz), 7.52(1H, d, J=8.8 Hz)

(2) 8-Amino-5-methoxy-4-(1,3-dioxoisoindolin-2-yl)-1-tetralone 424 mg of the compound obtained in (1) above, 288 mg of phthalimide, and 517 mg of triphenylphosphine was added to 20 ml of dried THF. While cooling in an ice-water bath, a THF solution of 0.34 ml of diethylazodicarboxylate (hereinafter abbreviated as "DEAD") was slowly added to the above mixture. After stirring for 30 minutes at the same temperature and an addition of 30 ml of water, the mixture was extracted with chloroform. The chloroform layer was washed with saturated brine and dried over magnesium sulfate. To the residue obtained by the concentration of the solvent were added 50 ml of dioxane, 50 ml of ethanol, and 280 mg of 10% palladium-on-carbon to effect catalytic hydrogenation. After removal of the catalyst by filtration and concentration of the filtrate, the residue was subjected to silica gel column chromatography using an chloroform-ethyl acetate (9:1) mixed solvent as an eluant to obtain fractions containing the target compound. The fractions were concentrated to produce 306 mg of the title compound.

NMR(CDCl$_3$)δ: 2.1–3.2(4H, m), 3.36(3H, s), 5.70(1H, m), 6.56(1H, d, J=9 Hz), 6.86(1H, d, J=9 Hz), 7.6–7.8(4H, m)

(3) (9S)-9-Ethyl-2,3-dihydro-9-hydroxy-4-methoxy-3-(1,3-dioxoisoindolin-2-yl)-1H,12H-benzo[de]pyrano[3',4': 6,7]indolizino[1,2-b]-quinoline-10,13(9H,15H)-dione To 30 ml of toluene were added 306 mg of the compound prepared in (2) above and 220 mg of trione. To this was added a catalytic amount of PPTS to react the mixture in a Deanstark apparatus under heating with refluxing for 6 hours. The reaction mixture was cooled to collect the precipitate by filtration, thus obtaining 390 mg of the title compound.

NMR(CDCl$_3$)δ: 1.04(3H, t, J=7.6 Hz), 1.8–2.0(2H, m), 2.3–2.4(1H, m), 2.5–2.56(1H, m), 3.1–3.2 (1H, m), 3.3–3.41 (1H, m), 3.87(3H, s), 5.25(2H, s), 5.31,5.75(2H, ABq, J=15.9 Hz), 6.05(1H, m), 7.52(1H, d, J=9.5 Hz), 7.6–7.8(5H, m), 8.28(1H, d, J=9.5 Hz)

Example 7

Preparation of (9S)-3-amino-9-ethyl-2,3-dihydro-9-hydroxy-4-methoxy-1H,12H-benzo[de]pyrano[3',4':6,7]indolizino[1,2-b]quinoline-10,13(9H,15H)-dione Hydrochloride

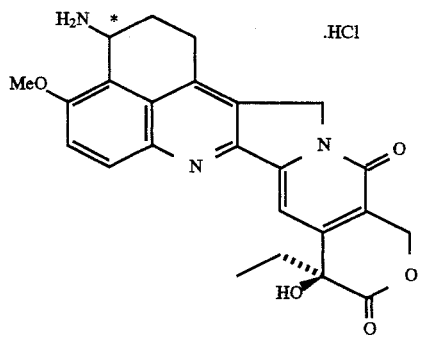

224 mg of the compound prepared in Example 6-(3) was dissolved in 14 ml of chloroform. After the addition of 10 ml of methanol, followed by 1.2 ml of hydrazine monohydrate, the mixture was stirred for 2 hours. After removing the solvent, 7 ml of 5N hydrochloric acid was added. The mixture was heated under reflux for 1 hour, followed by cooling. 10 ml of water was added to remove insoluble substances by filtration. The residue obtained by concentrating the filtrate was purified with reverse HPLC (CAPCELL PAK C18) using a mixture of acetonitrile-water-1N hydrochloric acid (20:80:2) to obtain 94 mg of Isomer A and 80 mg of Isomer B of the title compound.

Isomer A mp: above 215° C. (decomposed). NMR(CD$_3$OD)δ: 1.00 (3H, t, J=7.2 Hz), 1.95(2H, m), 2.4–2.5(1H, m), 2.5–2.6(1H, m), 3.2–3.4(2H, m), 4.12(3H, s), 5.17(1H, m), 5.23,5.32(2H, ABq, J=19.1 Hz), 5.37,5.55(2H, ABq, J=16.7 Hz), 7.62(1H, s), 7.85(1H, d, J=9.5 Hz), 8.28(1H, d, J=9.5 Hz)

Isomer B mp: above 180° C. (decomposed). NMR(CD$_3$OD)δ: 1.01 (3H, t, J=7.1 Hz), 1.97(2H, m), 2.3–2.45(1H, m), 2.5–2.6 (1H, m), 3.2–3.4(2H, m), 4.16(3H, s), 5.18(1H, m), 5.25, 5.38(2H, ABq, J=19.1 Hz), 5.39,5.57(2H, ABq, J=16.7 Hz), 7.67(1H, s), 7.89(1H, d, J=9.5 Hz), 8.31(1H, d, J=9.5 Hz)

Example 8

Preparation of (9S)-3-amino-9-ethyl-2,3-dihydro-4,9-dihydroxy-1H,12H-benzo[de]pyrano[3',4':6,7]indolizino[1,2-b]quinoline-10,13(9H,15H)-dione Hydrochloride

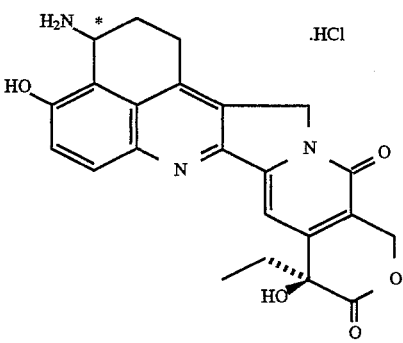

94 mg of Isomer A prepared in Example 7 was dissolved in 25 ml of acetic acid and heated under reflux for 30 hours. After removing the solvent, 10 ml of water was added to the residue to remove insoluble substances by filtratio. The filtrate was purified with reverse HPLC (CAPCELL PAK C18) using a mixture of acetonitrile-water-1N hydrochloric acid (20:80:2). The fractions containing the target compound was concentrated. 17 mg of Isomer A of the title compound was obtained by precipitation of the residue in a mithanol-ethanol-ethyl acetate mixture. Following the same procedure as above, 11 mg of Isomer B of the title compound was prepared from 68 mg of Isomer B of the compound which was prepared in Example 7.

Isomer A mp: above 170° C. (decomposed). NMR(DMSO-d$_6$)δ: 0.89(3H, t, J=7.2 Hz), 1.82(2H, m), 2.1–2.2(1H, m), 2.4–2.6 (1H, m), 3.15–3.35(2H, m), 4.93(1H, m), 5.21, 5.33(2H, ABq, J=19.1 Hz), 5.41, 5.45(2H, ASq, J=15.9 Hz), 7.28(1H, s), 7.64(1H, d, J=9.5 Hz), 8.20(1H, d, J=9.5 Hz) 8.25–8.35 (3H, m)

Isomer B mp: above 195° C. (decomposed). NMR(DMSO-d$_6$)δ: 0.89(3H, t, J=7.6 Hz), 1.8–2.0(2H, m), 2.1–2.2(1H, m), 2.4–2.6(1H, m), 3.15–3.35(2H, m), 4.94(1H, m), 5.21, 5.34 (2H, ABq, J=19.1 Hz), 5.43(2H, s), 7.28(1H, s), 7.65(1H, d, J=9.5 Hz), 8.10(1H, d, J=9.5 Hz), 8.25–8.35(3H, m)

Example 9

Preparation of (9S)-2-acetylamino-9-ethyl-2,3-dihydro-9-hydroxy-4-methoxy-1H,12H-benzo[de]pyrano[3',4': 6,7]indolizino[1,2-b]quinoline-10,13(9H,15H)-dione

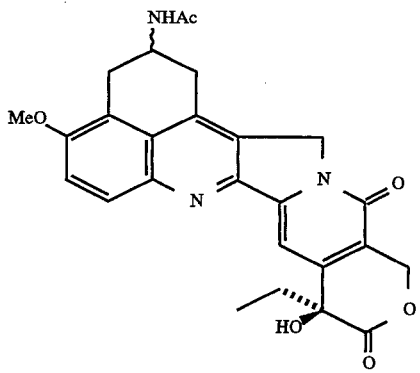

(1) 2-Acetylamino-8-methoxytetraline

To a solution of 5.18 gm of 8-methoxy-2-tetralone [described in J. Chem. Soc. 2636 (1965)] dissolved in 100 ml of methanol, were added 560 mg of sodium cyanoborohydride and 4.86 gm of ammonium acetate, and the mixture was stirred for 89 hours at room temperature. The reaction mixture was ice-cooled and adjusted to below pH 1, followed by the addition of 500 ml of water. After washing with ether, the water layer was adjusted to greater than pH 10 with potassium hydroxide and extracted with ether. The extract was dried over anhydrous magnesium sulfate, and the residue obtained by removing the solvent was dissolved in 50 ml of methylene chloride. 2 ml of pyridine and 2.4 ml of acetic anhydride were added to the solution, followed by stirring at room temparature for 1 hour. The reaction mixture was washed with 10% aqueous solution of hydrochloric acid, saturated aqueous solution of sodeum bicarbonate, and saturated brine in this order, and dried over anhydrous magnesium sulfate. After removal of the solvent, the residue was ctystallized in ethyl acetate and hexane to produce 2.47 gm of the title compound.

NMR(CDCL$_3$)δ: 1.75–2.11(2H, m), 1.98(3H, s), 2.49–2.58(1H, m), 2.79–3.32(3H, m), 3.80(3H, s), 4.21–4.37(1H, m), 6.62–6.76(2H, m), 7.12(1H, t, J=7.9 Hz)

(2) 2-Acetylamin-8-methoxy-5-nitrotetraline

To 20 ml of acetic anhydride cooled to 0° C., was slowly added 1.75 ml fuming nitric acid and further was added a drop of concentrated sulfuric acid. To this solution was added 2.2 mg of the compound obtained in (1) above, and the mixture was stirred for 20 minutes. 40 ml of 25% aqueous solution of sodium hydroxide was added to the reaction mixture, followed by stirring for a further 30 minutes. The precipitate was collected by filtration and washed with water. The organic layer was dried over magnesium sulfate. The residue obtained by rhe concentration of the solvent was subjected to silica gal column chromataghy using an chloroform-methanol (80:1) mixed solvent as an eluant to obtain fractions containing the target compound. The fractions were concentrated to produce 770 mg of the title compound.

mp: 207°–210° C. NMR(CDCL$_3$)δ: 1.6–2.2(2H, m), 2.01 (3H, s), 2.3–2.6(1H, m), 3.10–3.24(3H, m), 3.89(3H, s), 4.26(1H, m), 6.76(1H, d, J=9.1 Hz), 7.96(1H, d, J=8.9 Hz)

(3) 2.5-Diacetylamino-8-methoxytetraline 320 mg of the compound prepared in (2) above was dissolved in a mixed solvent of 5 ml of acetic anhydride and palladium-on-carbon, the mixture was catalytically hydrogenated for 5 hours. After removal of the catalyst by filtration and concentration of the filtrate, the residue was crystallized from chloroform to produce 190 mg of the title compound.

NMR(CDCL$_3$)δ: 1.6–2.2(2H, m), 1.96(3H, s), 2.16(3H, s), 2.4–2.9(4H, m), 3.80(3H, s), 4.0–4.4(1H, m), 6.68(1H, d, J=8.5 Hz), 7.18(1H, d, J=8.5 Hz)

(4) 3,8-Diacetylamino-5-methoxy-1-tetralone 190 mg of the compound prepared in (3) above was suspended into a mixture of 16 ml of acetone and 4 ml of 15% aqueous solution of magnesium sulfate, and to the solution was added 543 mg of potassium permanganate, followed by stirring for 1.5 hours at room temperature. After the addition of 150 ml of water, the reaction mixture was extracted withe chloroform. The extract was waxhed with saturated brine and dried over magnesium sulfate. After removal of the solvent, the residue was ctystallized in ethyl acetate and hexane to produce 124 mg of the title compound.

NMR(CDCL$_3$)δ: 1.96(3H, s), 2.21(3H, s), 2.6–3.4(4H, m), 3.84(3H, s), 4.4–4.7(1H, m), 7.11(1H, d, J=9.2 Hz), 8.61(1H, d, J=9.2 Hz)

(5) 3-Acetylamino-8-amino-5-methoxy-1-tetralone 102 mg of the compound prepared in (4) above was charged into 20 ml of 3N hydrochloric acid aqueous solution, and the mixture was heated at 60° C. for 2 hours while stirring. After cooling to 0° C. the reaction mixture was neutralized with sodium carbonate and extracted with chloroform. The extract was dried over magnesium sulfate, and subjected to silica gil column chromatograghy using an chloroform-methanol (40:1) mixed solvent as an eluant to obtain fractions containing the target compound. The fractions were concentrated to produce 66 mg of the title compound.

NMR(CDCL$_3$)δ: 1.94(3H, s), 2.51–3.34(4H, m), 3.76 (3H, s), 4.06–4.75(1H, m), 6.55(1H, d, J=9.0 Hz), 7.00(1H, d, J=9.0 Hz)

(6) (9S)-2-Acetylamino-9-ethyl-2,3-dihydro-9-hydroxy-4-methoxy-1H,12H-benzo[de]pyrano[3', 4':6,7]indolizino[1,2-b]qunoline-10,13(9H, 15H)-dione 126 mg of the compound prepared in (5) and 134 mg of trione were reacted for 24 hours and post-treated in the same manner as in Example 1-(5) to obtain 103 mg of the title compound.

IRv$_{max}^{KBr}$ cm$^{-1}$: 3392, 1748, 1660.

NMR(DMSO-d$_6$)δ: 0.89(3H, t, J=7.3 Hz), 1.85(3H, s), 1.87–1.93(2H, m), 2.67–2.81(1H, m), 3.02–3.09(1H, m), 3.97(3H, s), 4.22(1H, br), 5.09–5.25(2H, m), 5.37–5.46(2H, m), 6.47(1H, br, s), 7.29(1H, s), 7.71(1H, d, J=9.3 Hz), 8.03(1H, d, J=9.3 Hz), 8.13(1H, br). MASS m/z: 475(M$^+$)

Example 10

Preparation of (9S)-2-amino-9-ethyl-2,3-dihydro-9-hydroxy-4-methoxy-1H,12H-benzo[de]pyrano[3',4':6,7]indolizino[1,2-b]quinoline-10,13(9H,15H)-dione Hydrochloride

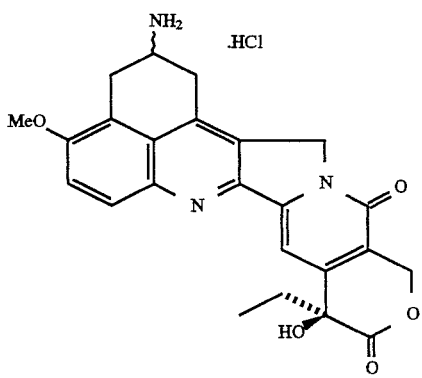

48 mg of the compound prepared in Example 9 was reacted and post-treated in the same manner as in Example 2 to obtain 42 mg of the title compound.

mp: above 240° C. (decomposed). IR$\nu_{max}^{KBr}$ cm$^{-1}$: 3440, 1744, 1658, 1592. NMR(DMSO-d$_6$)δ: 0.89(3H, t, J=7.3 Hz), 1.83–1.93(2H, m), 2.95–3.02(1H, m), 3.26–3.33(1H, m), 3.76(1H, br), 4.00(3H, s), 5.15–5.26(2H, m), 5.43(2H, s), 7.03(1H, s), 7.77(1H, d, J=9.3 Hz), 8.09(1H, d, J=9.3 Hz), 8.55(3H, br). MASS m\z: 433(M$^+$)

Example 11

Preparation of (9S)-2-amino-9-ethyl-2,3-dihydro-4,9-dihydroxy-1H,12H-benzo[de]pyrano[3',4':6,7]indolizino[1,2-b]quinoline-10,13(9H,15H)-dione Hydrochloride

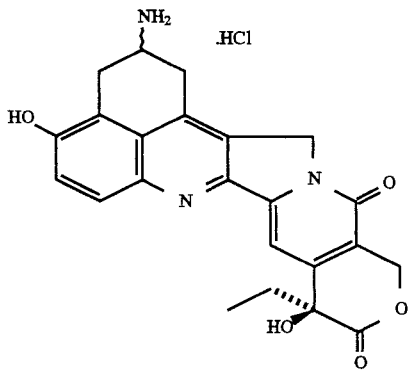

The compound prepared in Example 9 (46 mg) was reacted and post-treated in the same manner as in Example 5 to obtain 18 mg of the title compound.

mp: above 240° C. (decomposed). IR$\nu_{max}^{KBr}$ cm$^{-1}$: 3420, 1742, 1658, 1590. NMR(DMSO-d$_6$)δ: 0.89(3H, t, J=7.3 Hz), 1.85–1.92(2H, m), 2.91–2.98(1H, m), 3.24–3.31(1H, m), 3.75(1H, br), 5.23(2H, d, J=6.4 Hz), 5.42(2H, s), 7.27(1H, s), 7.55(1H, d, J=9.3 Hz), 7.93(1H, d, J=8.8 Hz), 8.48(3H, br s), 10.5(1H, br s). MASS m/z: 419(M$^+$)

Example 12

Preparation of (9S)-1-amino-9-ethyl-1,2-dihydro-9-hydroxy-4-methyl-12H-thiino[4,3,2-de]pyrano[3',4':6,7]indolizino[1,2-b]quinoline-10,13(9H,15H)-dione Hydrochloride

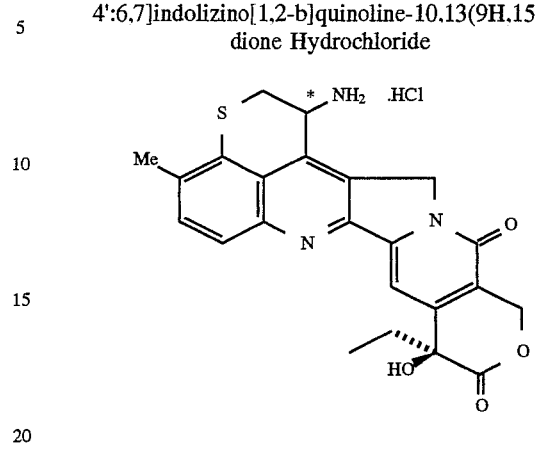

(1) 3,5-Diacetylamino-8-methyl-4-thiochromanone

To 3 ml of a THF solution containing 153 mg of potassium-t-butoxide was added 9 ml of a THF solution containing 291 mg of 5-acetylamino-8-methyl-4-thiochromanone [J. Heterocyclic Chem., 11, 515 (1974)]. After stirring for 5 minutes, 0.22 ml of n-butyl nitrite was added to the mixture, followed by further stirring for 1 hour at room temperature. After the addition of 20 ml of ether, the reaction mixture was stirred for another 1 hour. The deposited precipitate was collected by filtration, washed thoroughly with ether, and dissolved into a mixture of 20 ml of acetic acid and 20 ml of acetic anhydride. To the solution was added about 200 mg of zinc powder at room temperature while stirring. After the addition, the stirring was continued for a further 0.5 hour. Insoluble substances were removed by filtration, the solvent was evaporated, and 20 ml of chloroform was added to the residue. The residue, after washing with water, saturated aqueous solution of sodium hydroxide, and saturated brine in this order, was dried over anhydrous sodium sulfate. After evaporating the solvent, the residue was subjected to silica gel column chromatography using a hexane-ethyl acetate (4:1) mixed solvent as an eluant to obtain fractions containing the target compound. The fractions were concentrated to produce 109 mg of the title compound.

NMR(CDCl$_3$)δ: 2.12(3H, s), 2.23(3H, s), 2.26(3H, s), 3.06(1H, dd, J=12.5 Hz, 13.7 Hz), 3.60(1H, dd, J=4.4 Hz, 12.5 Hz), 4.94(1H, ddd, J=4.4 Hz, 4.9 Hz, 13.7 Hz), 6.82 (1H, m), 7.29(1H, d, J=8.8 Hz), 8.39(1H, d, J=8.8 Hz)

(2) 3-Acetylamino-5-amino-8-methyl-4-thiochromanone 109 mg of the compound prepared in (1) above was added to 10 ml of 6N hydrochloric acid, and the mixture was stirred at 90° C. for 20 minutes. After cooling, the mixture was alkalinized by the addition of sodium hydroxide and extracted with chloroform. The chloroform layer was dried over anhydrous sodium sulfate. The residue obtained after removal of the solvent was subjected to silica gel column chromatography using a chloroform-ethyl acetate (4:1) mixed solvent as an eluant to obtain fractions containing the target compound. The fractions were concentrated to produce 51 mg of the title compound.

NMR(CDCl$_3$)δ: 2.09(3H, s), 2.16(3H, s), 2.98(1H, m), 3.60(1H, m), 4.6–5.0(1H, m), 6.33(1H, d, J=9 Hz), 7.02(1H, d, J=9 Hz)

(3) (9S)-1-Amino-9-ethyl-1,2-dihydro-9-hydroxy-4-methyl-12H-thiino[4,3,2-de]pyrano[3',4':6,7]indolizino[1,2-b]quinoline-10,13(9H,15H)-dione Hydrochloride 45 mg of the compound prepared in (2) above and 47 mg of trione was added to 10 ml of toluene. To this was added a catalytic amount of PPTS to react the mixture in a Deanstark apparatus under heating with refluxing for 15 hours. The reaction mixture was cooled and the solvent was evaporated. The residue was subjected to silica gel column chromatography using a chloroform-methanol (98:2) mixed solvent as an eluant to obtain fractions containing the target compound. The fractions were concentrated by evaporating the solvent. 10 ml of hydrochloric acid was added to the residue and the mixture was stirred for 4 hours. After concentration, 10 ml of water was added to the resulting product to remove insoluble substances by filtration. The filtrate was purified with HPLC (CAPCELL PAK C18: trademark, manufactured by Shiseido Co.) using a mixture of acetonitrile-water-1N hydrochloric acid (20:80:1) to obtain 37 mg of Isomer A and 36 mg of Isomer B of the title compound.

Isomer A mp: above 210° C. (decomposed). NMR(DMSO-$d_6$)δ: 0.89(3H, t, J=7.3 Hz), 1.8–1.95(2H, m), 3.5–3.65(2H, m), 5.38(1H, m), 5.43, 5.89(2H, ABq, J=19.5 Hz), 5.44(2H, s), 6.53(1H, s), 7.34(1H, s), 7.78(1H, d, J=8.3 Hz), 7.96(1H, d, J=8.3 Hz), 8.88(3H, m)

Isomer B mp: above 224° C. (decomposed). NMR(DMSO-$d_6$)δ: 0.89(3H, t, J=7.3 Hz), 1.8–1.95(2H, m), 3.54(1H, dd, J=14.2 Hz, 1.5 Hz), 3.63(1H, dd, J=14.2 Hz, 3.4 Hz), 5.39(1H, m), 5.45(2H, m), 5.47, 5.92(2H, ABq, J=19.5 Hz), 6.54(1H, s), 7.36(1H, s), 7.79(1H, d, J=8.8 Hz), 7.97(1H, d, J=8.8 Hz), 8.94(3H, m)

Example 13

Preparation of (9S)-3-amino-4-fluoro-9-ethyl-2,3-dihydro-9-hydroxy-1H,12H-benzo[de]pyrano[3',4':6,7]indolizino[1,2-b]quinoline-10,13(9H,15H)-dione Hydrochloride

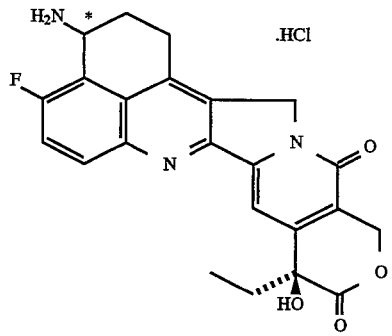

(1) Methyl 2-fluorocinnamate 15 gm of 2-fluorocinnamic acid was suspended into 100 ml of methanol. While maintaining the suspension at 0° C., 1.7 gm of thionyl chloride was added slowly. After the addition, the mixture was stirred for 30 minutes at 0° C. and for 4 hour at room temperature. The residue obtained by the removal of the solvent was subjected to silica gel column chromatography using chloroform as an eluant to obtain fractions containing the target compound. The fractions were concentrated to produce 17.8 gm of the title compound.

NMR(CDCl$_3$)δ: 3.82(3H, s), 6.54(1H, d, J=16.2 Hz), 6.97–7.63(4H, m), 7.82(1H, d, 16.2 Hz)

(2) Methyl 3-(2-fluorophenyl)propanoate 17.8 gm of the compound prepared in (1) above was dissolved in 200 ml of methanol. The mixture was catalytically hydrogenated using 6 gm of 10% palladium-on-carbon as a catalyst. After the removal of the catalyst by filtration and the solvent was evaporated to produce 14.7 gm of the title compound.

NMR(CDCl$_3$)δ: 2.53–2.72(2H, m), 2.8–3.1(2H, m), 3.67 (3H, s), 6.97–7.28(4H, m)

(3) 3-(2-Fluorophenyl)propanol 2.2 gm of lithium aluminum hydride was suspended in 110 ml of dried THF and stirred for 1 hour at room temperature. To the suspension was slowly added over 15 minutes a solution of 5 gm of the compound prepared in (2) above in 50 ml of THF. The mixture was stirred for 12 hours at room temperature, and after the addition of 20 ml of ethyl acetate, for a further 3 hours. Then, 5 ml of saturated aqueous solution of ammonium chloride was added to the mixture, followed by further stirring for 30 minutes. After removing the precipitate by filtration, the filtrate was washed with water and then with saturated brine, and dried over anhydrous sodium sulfate. The solvent was evaporated to obtain 4.27 gm of the title compound.

NMR(CDCl$_3$)δ: 1.6–2.1(2H, m), 2.75(2H, t, J=7.5 Hz), 3.68(2H, t, J=6.34 Hz), 6.8–7.6(4H, m)

(4) 3-(2-Fluorophenyl)propyl Tosylate 17.75 gm of the compound prepared in (3) above was dissolved into 200 ml of dry pyridine. To this was slowly added 24.25 gm of p-toluenesulfonyl chloride at 0° C. and the mixture was stirred for 3 hours at room temperature. After the addition of 300 ml of ether, the mixture was washed with water, followed by the addition of 6N hydrochloric acid to acidify it and washing with saturated brine. The product was dried over anhydrous sodium sulfate and the solvent was evaporated to obtain 31.3 gm of the title compound.

NMR(CDCl$_3$)δ: 1.8–2.2(2H, m), 2.45(3H, s), 2.68(2H, t, J=7.8 Hz), 4.04(2H, t, J=6.2 Hz), 6.8–7.4(4H, m), 7.33(2H, d, J=8 Hz), 7.79(2H, d, J=8 Hz)

(5) 4-(2-Fluorophenyl)butanonitrile

To a solution of 9.89 gm of sodium cyanate in 35 ml of dimethylsulfoxide (hereinafter abbreviated as DMSO) was added dropwise a solution of 31.2 gm of the compound prepared in (4) above in 70 ml of DMSO. The mixture was stirred for 12 hours at room temperature. After the addition of 500 ml of water, the mixture was extracted twice with 200 ml of ether. The extract was washed with water and saturated brine in this order, and dried over anhydrous sodium sulfate. The solvent was evaporated to obtain 15.4 gm of the title compound.

NMR(CDCl$_3$)δ: 1.8–2.2(2H, m), 2.15–2.42(2H, m), 2.81 (2H, t, J=7.65 Hz), 6.8–7.3(4H, m)

(6) 4-(2-Fluorophenyl)butanoic Acid 15.4 gm of the compound prepared in (5) above was added to a mixture of 400 ml of 5% aqueous solution of sodium hydroxide and 400 ml of diethylene glycol monoethyl ether. The mixture was heated under reflux for 3.5 hours, cooled to room temperature, and washed with ether. After the addition of concentrated hydrochloric acid to acidify, the water layer was extracted twice with 500 ml of ethyl acetate. The extract was washed with water and saturated brine in this order, and dried over anhydrous sodium sulfate. The solvent was evaporated to obtain 15.9 gm of the title compound.

NMR(CDCl$_3$)δ: 1.75–2.15(2H, m), 2.28–2.55(2H, m), 2.71(2H, t, J=7.43 Hz), 6.8–7.4(4H, m)

(7) 5-Fluoro-1-tetralone

To 200 gm of polyphosphoric acid heated at 80° C. was added 15.9 gm of the compound prepared in (6) above over 1 hour while stirring. The stirring was continued for another 1 hour at the same temperature. The resultant reaction mixture was poured into ice-cooled water and extracted with chloroform. The extract was washed with water and saturated brine in this order, and dried over anhydrous sodium sulfate. The solvent was evaporated to obtain 14.1 gm of the title compound.

NMR(CDCl$_3$)δ: 2.16(2H, m), 2.67(2H, t, J=6.3 Hz), 2.96 (2H, t, J=6.3 Hz), 7.20–7.31(2H, m), 7.84(1H, d, J=7.81 Hz)

(8) 5-Fluoro-8-nitro-1-tetralone 14 gm of the compound prepared in (7) above was dissolved into 100 ml of concentrated sulfuric acid. After cooling the solution, a solution of 9.05 gm of potassium nitrate in 80 ml of concentrated sulfuric acid was added dropwise while maintaining the internal temperature below 5° C. The stirring was continued for a further 30 minutes. The resultant reaction mixture was poured into ice-cooled water and extracted with chloroform. The extract was washed with saturated aqueous solution of sodium bicarbonate, water, and saturated brine in this order, and dried over anhydrous sodium sulfate. The solvent was evaporated and residue was recrystallized in methanol to obtain 9.15 gm of the title compound.

NMR(CDCl$_3$)δ: 2.18–2.24(2H, m), 2.74(2H, t, J=6.3 Hz), 2.99(2H, t, J=6.3 Hz), 7.29(1H, t, J=8.3 Hz), 7.38(1H, dd, J=4.4 Hz, 8.8 Hz)

(9) 5-Fluoro-8-nitro-4-(1,3-dioxoisoindoline-2-yl)-1-tetralone 323 mg of the compound prepared in (8) above, 323 mg of N-bromosuccinimide, and a catalytic amount of benzoyl peroxide were added to 20 ml of carbon tetrachloride. The mixture was heated under reflux for 4.5 hours, cooled to room temperature, and after the addition of 30 ml of chloroform, washed with cold 3% aqueous solution of sodium hydroxide, water, and saturated brine in this order, and dried over anhydrous sodium sulfate, followed by removal of the solvent by evaporation. The residue was dissolved into 15 ml of dimethylformamide (hereinafter abbreviated as DMF) and cooled to 0° C., followed by the addition of 100 mg of sodium azide, a bit at a time. The mixture was stirred for 30 minutes at 0° C. and for a further 1 hour at room temperature, and after the addition of 30 ml of water, was extracted twice with ether, washed with water and saturated brine in this order, and dried over anhydrous sodium sulfate, followed by removal of the solvent by evaporation. The residue was subjected to silica gel column chromatography using hexane-ethyl acetate (4:1) as an eluant to obtain fractions containing the target compound. The fractions were concentrated to obtain 308 mg of 4-azide isomer. To the isomer were added 10 ml of benzene, 390 mg of triphenylphosphine, and 220 mg of phthal anhydride. The mixture was heated under reflux for 7 hours, and a further 12 hours after the addition of 37 mg of tetra-n-butylammonium cyanide. The mixture was cooled to room temperature, and after the addition of 20 ml of ethyl acetate, washed with water and saturated brine in this order, and dried over anhydrous sodium sulfate, followed by removal of the solvent by evaporation. The residue was subjected to silica gel column chromatography using hexane-ethyl acetate (2:1) as an eluant to obtain fractions containing the target compound. The fractions were concentrated to produce 395 mg of the title compound.

NMR(CDCl$_3$)δ: 2.51–2.62(2H, m), 2.78–2.84(1H, m), 3.06–3.10(1H, m), 5.87(1H, t, J=5.0 Hz), 7.28(1H, t, J=8.8 Hz), 7.51(1H, dd, J=4.4 Hz, 8.8 Hz), 7.74–7.78(2H, m), 7.82–7.87(2H, m)

(10) 8-Amino-5-fluoro-4-(1,3-dioxoisoindoline-2-yl)-1-tetralone

To 320 mg of the compound prepared in (9) above were added 9 ml of dioxane and 15 ml of ethanol. The mixture was catalytically hydrogenated with 290 mg of 10% palladium-on-carbon. The catalyst was removed by filtration, the filtrate as concentrated, and the residue was subjected to silica gel column chromatography using hexane-ethyl acetate (2:1) as an eluant to obtain fractions containing the target compound. The fractions were concentrated to produce 206 mg of the title compound.

NMR(CDCl$_3$)δ: 2.3–2.55(2H, m), 2.61–2.70(1H, m), 2.85–2.30(1H, m), 5.78(1H, m), 6.59(1H, dd, J=4.4 Hz, 8.8 Hz), 6.96(1H, t, J=8.8 Hz), 7.65–7.75(2H, m), 7.75–7.85 (2H, m)

(11) (9S)-9-Ethyl-4-fluoro-2,3-dihydro-9-hydroxy-3-(1,3-dioxoisoindolin-2-yl)-1H,12H-benzo[de]pyrano[3',4':6,7]indolizino[1,2-b]quinoline-10,13(9H,15H)-dione 10 ml of toluene, 74 mg of the compound prepared in (10) above, and 66 mg of trione were reacted for 15 hours and treated in the same manner as in Example 1-(5) to obtain 120 mg of the title compound.

NMR(DMSO-d$_6$)δ: 0.90(3H, t, J=7.3 Hz), 1.89(2H, m), 2.36(1H, m), 2.45–2.5(1H, m), 3.25–3.4(2H, m), 5.34(2H, s), 5.45(2H, s), 5.99(1H, m), 7.36(0.5H, s), 7.37(0.5H, s), 7.69(1H, t, J=9.3 Hz), 7.86(4H, s), 8.18(1H, dd, J=5.4 Hz, 9.3 Hz)

(12) (9S)-3-Amino-4-fluoro-9-ethyl-2,3-dihydro-9-hydroxy-1H,12H-benzo[de]pyrano[3',4':6,7]indolizino[1,2-b]quinoline-10,13(9H,15H)-dione Hydrochloride 120 mg of the compound prepared in (11) above was dissolved in a mixed solvent of 7 ml of chloroform and 5 ml of methanol. After the addition of 0.7 ml of hydrazine monohydrate, the mixture was heated under reflux for 1 hour. The reaction mixture was concentrated to dryness and to the residue was added 7 ml of 4N hydrochloric acid, and the mixture was heated under reflux for 1 hour. After concentration to dryness, 10 ml of water to the residue to remove the insoluble substances by filtration. The filtrate was purified in the same manner as in Example 7 to obtain 32 mg of Isomer A and 20 mg of Isomer B of the title compound.

Isomer A mp: above 196° C. (decomposed) NMR(DMSO-$d_6$)δ: 0.90(3H, t, J=7.3 Hz), 1.87(2H, m), 2.15–2.30(1H, m), 2.4–2.6(1H, m), 3.3–3.4(2H, m), 5.08(1H, m), 5.26, 5.40 (2H, ABq, J=19 Hz), 5.44(2H, s), 7.35(1H, s), 7.88(1H, t, J=9.3 Hz), 8.30(1H, dd, J=5.5 Hz, 9.3 Hz), 8.70(3H, m)

Isomer B mp: above 215° C. (decomposed). NMR(DMSO-$d_6$)δ: 0.89(3H, t, J=7.3 Hz), 1.88(2H, m), 2.15–2.30(1H, m), 2.4–2.6(1H, m), 3.3–3.4(2H, m), 5.08(1H, m), 5.28, 5.40 (2H, ABq, J=19 Hz), 5.45(2H, s), 7.36(1H, s), 7.89(1H, t, J=9.3 Hz), 8.30(1H, dd, J=5.4 Hz, 9.3 Hz), 8.65(3H, m)

Example 14

Preparation of (9S)-3-amino-4-chloro-9-ethyl-2,3-dihydro-9-hydroxy-1H,12H-benzo[de]pyrano[3',4':6,7]indolizino[1,2-b]quinoline-10,13(9H,15H)-dione Hydrochloride

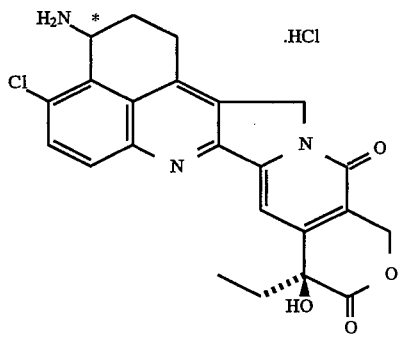

(1) 5-Chloro-8-nitro-4-(1,3-dioxoisoindoline-2-yl)-1-tetralone 403 mg of 5-chloro-8-nitro-1-tetralone, 412 mg of N-bromosuccinimide, and a catalytic amount of benzoyl peroxide were added to 20 ml of carbon tetrachloride. The mixture was heated under reflux for 6 hours, cooled to room temperature, and after the addition of 30 ml of chloroform, washed with cold 3% aqueous solution of sodium hydroxide, water, and saturated brine in this order, and dried over anhydrous sodium sulfate, followed by removal of the solvent by evaporation. The residue was dissolved into 10 ml of DMF and cooled to 0° C., followed by the addition of 140 mg of sodium azide, a bit at a time. The mixture was stirred for 30 minutes at 0° C. and for a further 1 hour at room temperature, and after the addition of 30 ml of water, was extracted twice with ether, washed with water and saturated brine in this order, and dried over anhydrous sodium sulfate, followed by removal of the solvent by evaporation. The residue was subjected to silica gel column chromatography using hexane-ethyl acetate (4:1) as an eluant to obtain fractions containing the target compound. The fractions were concentrated to obtain 450 mg of 4-azide isomer. To the isomer were added 20 ml of benzene, 487 mg of triphenylphosphine, and 275 mg of phthal anhydride. The mixture was heated under reflux for 7 hours, and a further 12 hours after the addition of 40 mg of tetra-n-butylammonium cyanide. After evaporating the solvent, the residue was subjected to silica gel column chromatography using hexane-ethyl acetate (2:1) as an eluant to obtain fractions containing the target compound. The fractions were concentrated to produce 356 mg of the title compound.

NMR(CDCl$_3$)δ: 2.40–2.48(1H, m), 2.56–2.67(1H, m), 2.75–2.83(1H, m), 2.96–3.75(1H, m), 5.83(1H, dd, J=2.9 Hz, 4.9 Hz), 7.46(1H, d, J=8.3 Hz), 7.63(1H, d, J=8.3 Hz), 7.74–7.78(2H, m), 7.82–7.84(2H, m)

(2) 8-Amino-5-chloro-4-(1,3-dioxoisoindoline-2-yl)-1-tetralone.

To 320 mg of the compound prepared in (1) above were added 9 ml of dioxane and 15 ml of ethanol. The mixture was catalytically hydrogenated with 200 mg of 10% palladium-on-carbon. The catalyst was removed by filtration, the filtrate was concentrated, and the residue was subjected to silica gel column chromatography using hexane-ethyl acetate (2:1) as an eluant to obtain fractions containing the target compound. The fractions were concentrated to produce 176 mg of the title compound.

NMR(CDCl$_3$)δ: 2.4–3.3(4H, m), 5.72(1H, m), 6.60(1H, d, J=8.3 Hz), 7.17(1H, d, J=8.3 Hz), 7.6–7.9(4H, m)

(3) (9S)-3-Amino-4-chloro-9-ethyl-2,3-dihydro-9-hydroxy-1H,12H-benzo[de]pyrano[3',4':6,7]indolizino[1,2-b]quinoline-10,13(9H,15H)-dione Hydrochloride 15 ml of toluene, 176 mg of the compound prepared in (2) above, and 135 mg of trione were reacted for 16 hours and post-treated to obtain 193 mg of (9S)-9-ethyl-4-chloro-2,3-dihydro-9-hydroxy-3-(1,3-dioxoisoindoline-2-yl)-1H,12H-benzo[de]pyrano[3',4':6,7]indolizino[1,2-b]quinoline-10,13 (9H,15H)-dione as a mixture of 3-position isomer. 171 mg of this mixture was processed in the same manner as in Example 13-(12) to obtain 63 mg of Isomer A and 59 mg of Isomer B of the title compound.

Isomer A mp: above 190° C. (decomposed). NMR(DMSO-$d_6$)δ: 0.89(3H, t, J=7.3 Hz), 1.86(2H, m), 2.24(1H, m), 2.61(1H, m), 3.2–3.5(2H, m), 5.09(1H, m), 5.23, 5.39(2H, ABq, J=19.5 Hz), 5.44(2H, s), 7.35(1H, s), 7.98(1H, d, J=9.3 Hz), 8.23(1H, d, J=9.3 Hz), 8.69(3H, m)

Isomer B mp: above 215° C. (decomposed). NMR(DMSO-$d_6$)δ: 0.88(3H, t, J=7.3 Hz), 1.88(2H, m), 2.24(1H, m), 2.54(1H, m), 3.3–3.5(2H, m), 5.12(1H, m), 5.27, 5.42(2H, ABq, J=19.0 Hz), 5.45(2H, s), 7.36(1H, s), 8.00(1H, d, J=9.3 Hz), 8.26(1H, d, J=9.3 Hz), 8.56(3H, m)

Example 15

Preparation of (9S)-1-acetylaminomethyl-4-chloro-9-ethyl-2,3-dihydro-9-hydroxy-1H,12H-benzo[de]pyrano[3',4':6,7]indolizino[1,2-b]quinoline-10,13(9H,15H)-dione

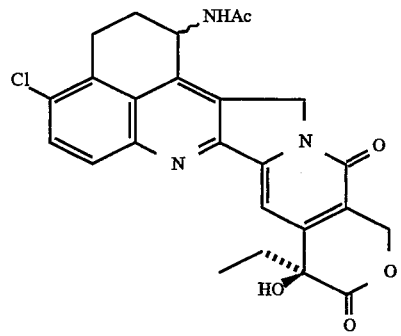

(1) 8-Acetylamino-5-chloro-2-hydroxymethylene-1-tetralone 960 mg of 60% aqueous solution of sodium hydride was added to 8 ml of ethyl formate under ice-cooling, and 5 minutes after the mixture was cooled to room temperature, a solution of 1.43 gm of 8-acetylamino-5-chloro-1-tetralone dissolved in 30 ml of dimethoxyethane was slowly added. After the addition of 0.06 ml of ethanol, the mixture was stirred for 30 minutes. The reaction mixture was poured into 300 ml of 14% aqueous solution of sodium chloride, extracted with ethyl acetate, washed with 10% aqueous solution of citric acid and saturated brine, and dried over anhydrous sodium sulfate. After concentration, ether was added to the residue to collect the precipitate of 1.30 gm of the title compound the by filtration.

IR$\nu_{max}^{KBr}$ cm$^{-1}$: 1650, 1574, 1502, 1194. NMR(CDCl$_3$) δ: 2.23(s, 3H), 2.49(t, 2H, J=7 Hz), 3.03(t, 2H, J=7 Hz), 7.50(d, 1H, J=9 Hz), 8.56(d, 1H, J=9 Hz), MASS m/z: 265(M$^+$), 267(M$^+$+2)

(2) 9-Acetylamino-6-chloro-4,5-dihydronaphtho[1,2-d]-isoxazole 1.29 gm of the compound prepared in (1) above was dissolved into 30 ml of acetic acid. After the addition of 339 mg of hydroxylamine hydrochloride, the mixture was heated for 10 minutes at 120° C. while stirring. After cooling, water was added to collect the precipitate by filtration. The precipitate was washed with water and hexane to obtain 1.1 gm of the title compound.

IR$\nu_{max}^{KBr}$ cm$^{-1}$: 1664, 1524, 1390, 1288. NMR(CDCl$_3$)δ: 2.29(s, 3H), 2.80(t, 2H, J=8 Hz), 3.18(t, 2H, J=8 Hz), 7.37(d, 1H, J=9 Hz), 8.25(s, 1H), 8.30(d, 1H, J=9 Hz), 8.80(s, 1H). MASS m/z: 262(M$^+$), 264(M$^+$+2)

(3) 8-Acetylamino-5-chloro-2-cyano-1-tetralone

To a solution obtained by dissolving 1.54 gm of the compound prepared in (1) above in 20 ml of anhydrous ethanol, was slowly added a solution of 460 mg of sodium methoxide in 50 ml of anhydrous ethanol. After stirring 3 hours at room temperature, 10 ml of 1N hydrochloric acid and water were added to the reaction mixture, followed by extraction with chloroform. The extract was washed with saturated brine, dried over anhydrous sodium sulfate, and concentrated to obtain 1.36 gm of the title compound.

IR$\nu_{max}^{KBr}$ cm$^{-1}$: 2251, 1702, 1658, 1598, 1522. NMR (CDCl$_3$)δ: 2.26(s, 3H), 2.3–2.7(m, 2H), 2.9–3.5(m, 2H), 3.83(dd, 1H, J=12 Hz,5 Hz), 7.61(d, 1H, J=9 Hz), 8.70(d, 1H, J=9 Hz), 11.56(s, 1H). MASS m/z: 262(M$^+$), 264(M$^+$+2)

(4) 8-Acetylamino-2-acetylaminomethyl-5-chloro-1-tetralone 1.36 gm of the compound prepared in (3) above was reacted in the same manner as in Example 28-(3) and post-treated to obtain 1.20 gm of the title compound.

NMR(CDCl$_3$)δ: 2.01(s, 3H), 2.25(s, 3H), 1.7–2.4(m, 2H), 2.6–3.0(m, 2H), 3.1–3.6(m, 2H), 3.6–3.8(m, 1H), 6.23(br.s, 1H), 7.52(d, 1H, J=9 Hz), 8.60(d, 1H, J=9 Hz), 11.89(s, 1H). MASS m/z: 308(M$^+$), 310(M$^+$+2)

(5) 2-Acetylaminomethyl-8-amino-5-chloro-1-tetralone

The procedure of Example 1-(4) was followed by using 1.20 gm of the compound prepared in (3) above, instead of 2,8-diacetylamino-1-tetralone. The reaction product was post-treated to obtain 1.20 gm of the title compound.

NMR(CDCl$_3$)δ: 1.98(s, 3H), 1.7–2.3(m, 2H), 2.5–3.0(m, 2H), 3.0–3.5(m, 2H), 3.7–3.9(m, 1H), 6.37(br.s, 2H), 6.48(d, 1H, J=9 Hz), 7.23(d, 1H, J=9 Hz). MASS m/z: 266(M$^+$), 268(M$^+$+2)

(6) (9S)-1-Acetylaminomethyl-4-chloro-9-ethyl-2,3-dihydro-9-hydroxy-1H,12H-benzo[de]pyrano[3',4':6,7]indolizino[1,2-b]quinoline-10,13(9H,15H)-dione 820 mg of the compound prepared in (5) above and 808 mg of trione were reacted for 24 hours in the same manner as in Example 1-(5). The reaction mixture was concentrated and the residue was subjected to silica gel column chromatography using chloroform-methanol (40:1) as an eluant to obtain fractions containing the target compound. The fractions were concentrated to produce 420 mg of the title compound.

NMR(DMSO-d$_6$)δ: 0.88(t, 3H, J=7 Hz), 1.87(s, 3H), 1.7–2.0(m, 2H), 2.2–3.6(m, 7H), 5.37(s, 2H), 5.45(s, 2H), 6.52(br.s, 2H), 7.34(s, 1H), 7.88(d, 1H, J=9 Hz), 8.04(d, 1H, J=9 Hz). MASS m/z: 493(M$^+$), 495(M$^+$+2)

Example 16

Preparation of (9S)-1-aminomethyl-4-chloro-9-ethyl-2,3-dihydro-9-hydroxy-1H,12H-benzo[de] pyrano[3',4':6,7]indolizino[1,2-b]quinoline-10,13 (9H,15H)-dione Hydrochloride

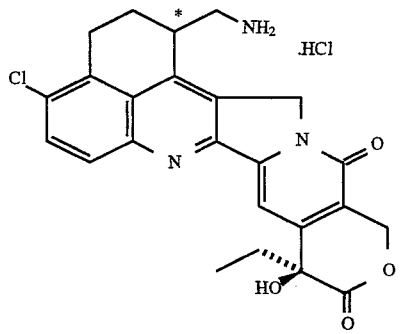

100 mg of the compound prepared in Example 15-(6) was reacted in the same manner as in Example 2 and post-treated to obtain 25 mg of Isomer A and 22 mg of Isomer B of the title compound.

Isomer A mp: 230°–240° C. (decomposed). NMR(DMSO-d$_6$)δ: 0.88(t, 3H, J=7 Hz), 1.8–2.0(m, 2H), 1.9–3.8(m, 7H), 5.32, 5.48(ABq, 2H, J=17 Hz), 5.46(s, 2H), 6.56(br.s, 1H), 7.35(s, 1H), 7.91(d, 1H, J=9 Hz), 8.07(d, 1H, J=9 Hz) 8.14(s, 3H). MASS m/z: 451(M$^+$), 453(M$^+$+2)

Isomer B mp: 250°–255° C. (decomposed). NMR(DMSO-d$_6$)δ: 0.88(t, 3H, J=7 Hz), 1.8–2.0(m, 2H), 1.9–3.8(m, 7H), 5.32, 5.48(ABq, 2H, J=19 Hz), 5.45(s, 2H), 6.57(br.s, 1H), 7.35(s, 1H), 7.90(d, 1H, J=9 Hz), 8.06(d, 1H, J=9 Hz). MASS m/z: 451(M$^+$), 453(M$^+$+2)

Example 17

Preparation of (9S)-1-acetylamino-9-ethyl-1,2-dihydro-9-hydroxy-4-methyl-3H,12H-pyrano[3',4':6,7]indolizino[1,2-c]benzo[ij][2,7]naphthyridine-10,13(9H,15H)-dione

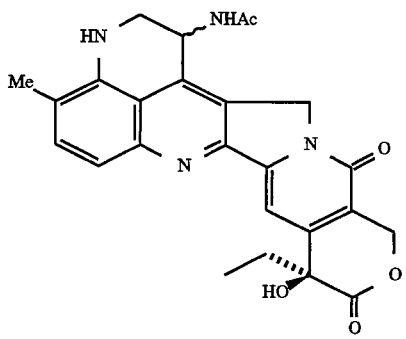

(1) 4-Acetyl-5-acetylamino-8-methyl-2,3-dihydroquinoline-4-one

To a solution of 7.0 gm of 5-amino-8-methyl-2,3-dihydroquinoline-4-one (described in Japanese Patent Laid-open (ko-kai) 279891/1989) in a mixed solvent of 30 ml of dichloromethane and 80 ml of dioxane was added 15 ml of acetyl chloride, and the mixture was heated under reflux for 2 hours. 200 ml of ethyl acetate was added to the residue obtained by removing the solvent, and mixture was washed with saturated aqueous solution of sodium bicarbonate and saturated brine, and dried over anhydrous sodium sulfate. After concentration, the residue was recrystallized from ether to obtain 7.45 gm of the title compound.

NMR(CDCl$_3$)δ: 1.95(s, 3H), 2.23(s, 3H), 2.27(s, 3H), 2.0–5.5(m, 5H), 7.45(d, 1H, J=8 Hz), 8.59(d, 1H, J=8 Hz)

(2) 1-Acetyl-5-acetylamino-3-hydroxyimino-8-methyl-2,3-dihydroquinoline-4-one The procedure of Example 1-(2) was followed by using 2.6 gm of the compound prepared in (1) above instead of 8-acetylamino-1-tetralone. The reaction product was post-treated to obtain 2.89 gm of the title compound.

mp: 195°–205° C. (decomposed). IRν$_{max}^{KBr}$ cm$^{-1}$: 1674, 1590, 1518, 1404. NMR(CDCl$_3$)δ: 2.24(s, 9H), 1.8–5.5(m, 3H), 7.54(d, 1H, J=8 Hz), 8.62(d, 1H,J=8 Hz). MASS m/z: 289(M$^+$)

(3) 1-Acetyl-3,5-diacetylamino-8-methyl-2,3-dihydroquinoline-4-one

The procedure of Example 1-(3) was followed by using 2.89 gm of the compound prepared in (2) above instead of 8-acetylamino-2-hydroxyimino-1-tetralone. The reaction product was post-treated to obtain 1.65 gm of the title compound.

mp: 216°–221° C. (decomposed). IRν$_{max}^{KBr}$ cm$^{-1}$: 1662, 1594, 1518. NMR(CDCl$_3$)δ: 2.12(s, 3H), 2.23(s, 6H), 2.54 (s, 3H), 3.3–5.0(m, 1H), 6.1–6.6(br. s, 1H), 7.44(d, 1H, J=8 Hz), 7.60(d, 1H, J=8 Hz). MASS m/z: 317(M$^+$)

(4) 3-Acetylamino-5-amino-8-methyl-2,3-dihydroquinoline-4-one

The procedure of Example 1-(4) was followed by using 1.40 gm of the compound prepared in (3) above instead of 2,8-diacetylamino-1-tetralone. The reaction product was post-treated to obtain 0.79 gm of the title compound.

NMR(CDCl$_3$)δ: 2.01(s, 3H), 2.08(s, 3H), 3.0–4.5(m, 3H), 5.89(d, 1H, J=8 Hz), 6.95(d, 1H, J=8 Hz) 5.7–6.8(br.s, 2H). MASS m/z: 233(M$^+$)

(5) (9S)-1-Acetylamino-9-ethyl-1,2-dihydro-9-hydroxy-4-methyl-3H,12H-pyrano[3',4':6,7]indolizino[1,2-c]benzo[ij][2,7]naphthyridine-10,13(9H,15H)-dione 900 mg of trione, 3 mg of PPTS, and 20 ml of acetic acid were added to 790 mg of the compound prepared in (4) above, and the mixture was heated in a nitrogen stream at 100° C. for 7 hours while stirring. The reaction mixture was concentrated, and the residue was subjected to silica gel column chromatography using chloroform-methanol (20:1) as an eluant to obtain fractions containing the target compound. The fractions were concentrated to produce 210 mg of the title compound.

mp: 225°–235° C. IRν$_{max}^{KBr}$ cm$^{-1}$: 1746, 1658, 1596, 1156. NMR(DMSO-d$_6$)δ: 0.87(t, 3H, J=7 Hz), 1.8–2.0(m, 2H), 1.90, 1.91(each s, 3H), 2.30(s, 3H), 5.16, 5.25(ABq, 2H, J=18 Hz), 5.42(s, 2H), 5.3–5.6(m, 1H), 6.17(br.s, 1H), 7.26(s, 1H), 7.36(d, 1H, J=8 Hz), 7.52(d, 1H, J=8 Hz) MASS m/z: 460(M$^+$)

Example 18

Preparation of (9S)-1-amino-9-ethyl-1,2-dihydro-9-hydroxy-4-methyl-3H,12H-pyrano[3',4':6,7]indolizino[1,2-c]benzo[ij][2,7]naphthyridine-10,13(9H,15H)-dione Hydrochloride

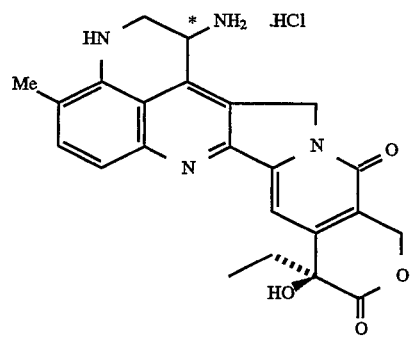

The compound obtained in Example 17-(5) (400 mg) was reacted for 4 hours in the same manner as in Example 2 and post-treated to produce 80 mg of Isomer A and 55 mg of Isomer B of the title compound.

Isomer A mp: 230°–250° C. (decomposed). IRν$_{max}^{KBr}$ cm$^{-1}$: 1756, 1658, 1614. NMR(DMSO-d$_6$)δ: 0.88(t, 3H, J=7 Hz), 1.7–2.0 (m, 2H), 2.35(s, 3H), 3.50, 3.87(each d, 1H, J=12 Hz), 5.0–5.2(m, 1H), 5.44(s, 2H), 5.37, 5.83° (ABq, 2H, J=10 Hz), 7.31(s, 1H), 7.44(d, 1H, J=8 Hz), 7.59(d, 1H, J=8 Hz), 8.77(br.s, 3H). MASS m/z: 418(M$^+$)

Isomer B mp: 220°–240° C. (decomposed). IRν$_{max}^{KBr}$ cm$^{-1}$: 1746, 1658, 1592. NMR(DMSO-d$_6$)δ: 0.88(t, 3H, J=7 Hz), 1.7–2.0 (m, 2H), 2.35(s, 3H), 3.50, 3.86(each d, 1H, J=12 Hz), 5.0–5.2(m, 1H), 5.45(s, 2H), 5.39, 5.79(ABq, 2H, J=9 Hz), 6.3–6.5(br, 1H), 6.54(s, 1H), 7.32(s, 1H), 7.45(d, 1H, J=8 Hz), 7.60(d, 1H, J=8 Hz), 8.70(br. s, 3H). MASS m/z: 418(M$^+$)

Example 19

Preparation of (9S)-1-acetylamino-4-chloro-9-ethyl-2,3-dihydro-9-hydroxy-1H,12H-benzo[de]pyrano[3',4':6,7]indolizino[1,2-b]quinoline-10,13(9H,15H)-dione

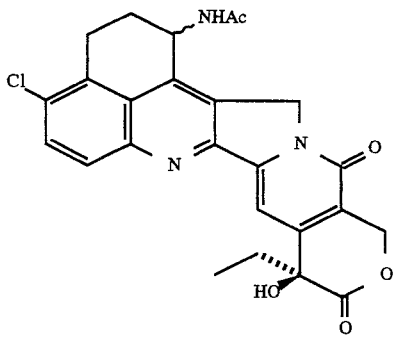

(1) 2,8-Diacetyl-5-chloro-1-tetralone

The reaction was carried out in the same manner as in Example 1-(2), except that 600 mg of 8-acetylamino-5-chloro-1-tetralone was used instead of 8-acetylamino-1-tetralone of Example 1-(2). Crude 8-acetylamino-5-chloro-2-hydroxyimino-1-tetralone which was obtained by the post-treatment was reacted in the same manner as in Example 1-(3) and post-treated to produce 304 mg of the title compound.

IR$v_{max}^{KBr}$ cm$^{-1}$: 3296, 1652, 1574, 1464. NMR(CDCl$_3$) δ: 1.75–2.04(1H, m), 2.12(3H, s), 2.23(3H, s), 2.70–3.18 (3H, m), 4.55–4.83(1H, m), 6.4(1H, br), 7.55(1H, d, J=9.0 Hz), 8.61(1H, d, 9.2 Hz). MASS m/z: 294(M$^+$)

(2) 2-Acetylamino-8-amino-5-chloro-1-tetralone

The reaction was carried out in the same manner as in Example 1-(4), except that 270 mg of the compound prepared in (1) above was used instead of 2,8-diacetylamino-1-tetralone of Example 1-(4), and post-treated to produce 160 mg of the title compound.

IR$v_{max}^{KBr}$ cm$^{-1}$: 3448, 1614, 1458. NMR(CDCl$_3$)δ: 1.73–1.87(1H, m), 2.09(3H, s), 2.66–3.15(3H, m), 4.53–4.74(1H, m), 6.50(1H, d, J=9.0 Hz), 7.26(1H, d, J=9.0 Hz). MASS m/z: 252(M$^+$)

(3) (9S)-1-Acetylamino-4-chloro-9-ethyl-2,3-dihydro-9-hydroxy-1H,12H-benzo[de]pyrano[3',4':6,7]indolizino[1,2-b]quinoline-10,13(9H,15H)-dione 130 mg of the compound prepared in (2) above and 136 mg of trione were reacted for 24 hours in the same manner as in Example 1-(5) and post-treated to produce 174 mg of the title compound.

mp: above 240° C. (decomposed). IR$v_{max}^{KBr}$ cm$^{-1}$: 3416, 1660, 1494. NMR(DMSO-d$_6$)δ: 0.86–0.90(3H, m), 1.85–1.89(2H, m), 1.91(3/2H, s), 1.92(3/2H, s), 2.16(2H, br s), 3.24(2H, br s), 5.18–5.30(2H, m), 5.43(2H, s), 5.57–5.62 (1H, m), 6.52(1H, s), 7.33(1H, s), 7.89(1H, d, J=8.8 Hz), 8.05(1H, d, J=8.8 Hz), 8.46–8.50(1H, m). MASS m/z: 479(M$^+$)

Example 20

Preparation of (9S)-1-amino-4-chloro-9-ethyl-2,3-dihydro-9-hydroxy-1H,12H-benzo[de]pyrano[3',4':6,7]indolizino[1,2-b]quinoline-10,13(9H,15H)-dione Hydrochloride

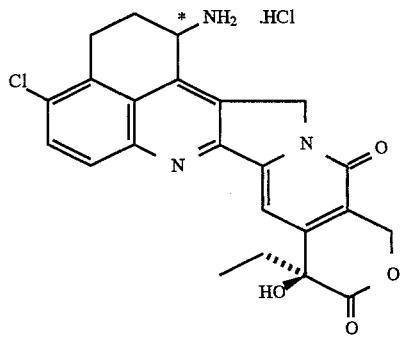

The compound prepared in Example 19-(3) (124 mg) above was reacted for 6 hours in the same manner as in Example 2 and post-treated to produce Isomer A (8.2 mg) and Isomer B (8.2 mg) of the title compound.

Isomer A mp: above 240° C. (decomposed). NMR(DMSO/d$_6$)δ: 0.89(3H, t, J=6.8 Hz), 1.81–1.92(2H, m), 2.18–2.25(1H, m), 3.16–3.25(1H, m), 5.13(1H, br), 5.45–5.49(3H, m), 5.95 (1H, d, J=19 Hz), 6.56(1H, s), 7.37(1H, s), 7.97(1H, d, J=9.3 Hz), 8.13(1H, d, J=9.3 Hz), 8.79(1H, br)

Isomer B mp: above 240° C. (decomposed). NMR(DMSO-d$_6$)δ: 0.88(3H, t, J=7.3 Hz), 1.81–1.92(2H, m), 2.18–2.25(1H, m), 3.16–3.25(1H, m), 5.14(1H, br), 5.46–5.50(3H, m), 5.90 (1H, d, J=19 Hz), 6.56(1H, s), 7.38(1H, s), 7.98(1H, d, J=9.3 Hz), 8.14(1H, d, J=9.3 Hz), 8.66(1H, br)

Example 21

Preparation of (9S)-1-acetylamino-9-ethyl-4-fluoro-2,3-dihydro-9-hydroxy-1H,12H-benzo[de]pyrano[3',4':6,7]indolizino[1,2-b]quinoline-10,13(9H,15H)-dione

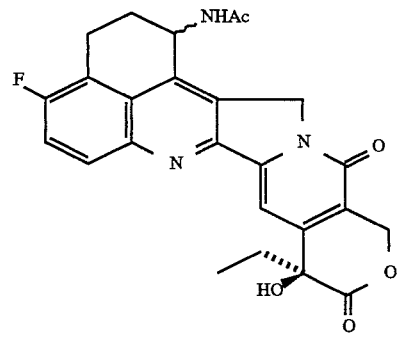

(1) 2,8-Diacetyl-5-fluoro-1-tetralone

The reaction was carried out in the same manner as in Example 1-(2), except that 600 mg of 8-acetylamino-5-fluoro-1-tetralone was used instead of 8-acetylamino-1-tetralone of Example 1-(2). Crude 8-acetylamino-5-fluoro-2-hydroxyimino-1-tetralone which was obtained by the post-treatment was reacted in the same manner as in Example 1-(3) and post-treated to produce 372 mg of the title compound.

IRv$_{max}^{KBr}$ cm$^{-1}$: 3264, 1698, 1614, 1538, 1400. NMR (CDCl$_3$)δ: 1.83–2.04(1H, m), 2.11(3H, s), 2.22(3H, s), 2.65–3.19(3H, m), 4.61–4.82(1H, m), 6.5(1H, br s), 7.26 (1H, t, J=9.2 Hz), 8.62(1H, dd, J=4.6, 9.6 Hz). MASS m/z: 278(M$^+$)

(2) 2-Acetylamino-8-amino-5-fluoro-1-tetralone

The reaction was carried out in the same manner as in Example 1-(4), except that 300 mg of the compound prepared in (1) above was used instead of 2,8-diacetylamino-1-tetralone of Example 1-(4), and post-treated to produce 182 mg of the title compound.

IRv$_{max}^{KBr}$ cm$^{-1}$: 3428, 2960, 1622, 1472. NMR(CDCl$_3$) δ: 1.73–1.88(1H, m), 2.10(3H, s), 2.69–3.08(3H, m), 4.49–4.69(1H, m), 6.43–6.54(1H, m), 7.06(1H, t, J=8.8 Hz), MASS m/z: 236(M$^+$)

(3) (9S)-1-Acetylamino-9-ethyl-4-fluoro-2,3-dihydro-9-hydroxy-1H,12H-benzo[de]pyrano[3',4':6,7]indolizino[1,2-b]quinoline-10,13(9H,15H)-dione 160 mg of the compound prepared in (2) above and 179 mg of trione were reacted for 24 hours in the same manner as in Example 1-(5) and post-treated to produce 224 mg of the title compound.

mp: above 240° C. (decomposed). IRv$_{max}^{KBr}$ cm$^{-1}$: 3292, 2944, 1750, 1660, 1598. NMR(DMSO-d$_6$)δ: 0.88(3H, t, J=8.8 Hz), 1.82–1.92(2H, m), 1.93(3H, s), 2.09–2.14(2H, m), 3.16–3.19(2H, m), 5.18–5.29(2H, m), 5.43(2H, s), 5.57–5.62(1H, m), 6.51(1H, s), 7.33(1H, s), 7.78(1H, t, J=9.3 Hz), 8.11(1H, dd, J=5.4, 9.3 Hz), 8.51(1H, d, J=8.8 Hz). MASS m/z: 463(M$^+$)

Example 22

Preparation of (9S)-1-amino-9-ethyl-4-fluoro-2,3-dihydro-9-hydroxy-1H,12H-benzo[de]pyrano[3',4':6,7]indolizino[1,2-b]quinoline-10,13(9H,15H)-dione Hydrochloride

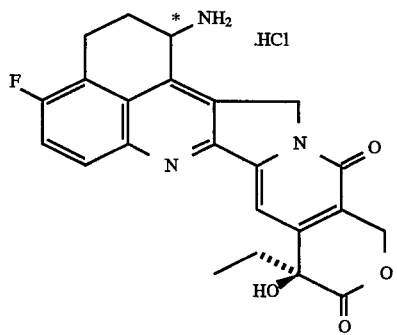

The compound prepared in Example 21-(3) (180 mg) above was reacted for 5 hours in the same manner as in Example 2 and post-treated to produce Isomer A (10 mg) and Isomer B (14 mg) of the title compound.

Isomer A mp: above 240° C. (decomposed). NMR(DMSO-d$_6$)δ: 0.89(3H, t, J=7.3 Hz), 1.81–1.94(2H, m), 2.13–2.21(1H, m), 3.14–3.22(1H, m), 5.13(1H, br), 5.43–5.48(3H, m), 5.92 (1H, d, J=19 Hz), 6.55(1H, s), 7.37(1H, s), 7.85(1H, t, J=9.3 Hz), 8.18(1H, dd, J=5.4, 9.3 Hz), 8.68(1H, br)

Isomer B mp: above 240° C. (decomposed). NMR(DMSO-d$_6$)δ: 0.89(3H, t, J=7.3 Hz), 1.83–1.93(2H, m), 2.16–2.20(1H, m), 3.15–3.25(1H, m), 5.16(1H, br), 5.45–5.50(3H, m), 5.95 (1H, d, J=19 Hz), 7.37(1H, s), 7.85(1H, t, J=9.3 Hz), 8.19(1H, dd, J=5.4, 9.3 Hz), 8.81(1H, br)

Example 23

Preparation of (9S)-1-acetylamino-4-cyano-2,3-dihydro-9-hydroxy-1H,12H-benzo[de]pyrano[3',4':6,7]indolizino[1,2-b]quinoline-10,13(9H,15H)-dione

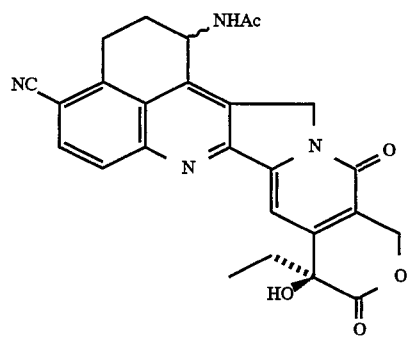

(1) 2,8-Diacetyl-5-cyano-1-tetralone

The reaction was carried out in the same manner as in Example 1-(2), except that 1 gm of 8-acetylamino-5-cyano-1-tetralone was used instead of 8-acetylamino-1-tetralone of Example 1-(2). Crude 8-acetylamino-5-cyano-2-hydroxyimino-1-tetralone which was obtained by the post-treatment was reacted in the same manner as in Example 1-(3) and post-treated to produce 270 mg of the title compound.

IRv$_{max}^{KBr}$ cm$^{-1}$: 3292, 2228, 1708, 1666, 1588, 1518. NMR(CDCl$_3$)δ: 1.71–2.05(1H, m), 2.12(3H, s), 2.27(3H, s), 2.66–3.43(3H, m), 4.60–4.87(1H, m), 6.3(1H, br), 7.77(1H, d, J=8.7 Hz), 8.78(1H, d, J=9.0 Hz). MASS m/z: 285(M$^+$)

(2) 2-Acetylamino-8-amino-5-cyano-1-tetralone

The reaction was carried out in the same manner as in Example 1-(4), except that 250 mg of the compound prepared in (1) above was used instead of 2,8-diacetylamino-1-tetralone of Example 1-(4), and post-treated to produce 182 mg of the title compound.

IRv$_{max}^{KBr}$ cm$^{-1}$: 3428, 3336, 2216, 1652, 1614, 1542. NMR(CDCl$_3$)δ: 1.6–2.0(1H, m), 2.09(3H, s), 2.56–3.39(3H, m), 4.51–4.71(1H, m), 6.59(1H, d, J=9.0 Hz), 7.40(1H, d, J=9.0 Hz). MASS m/z: 243(M$^+$)

(3) (9S)-1-Acetylamino-4-cyano-9-ethyl-2,3-dihydro-9-hydroxy-1H,12H-benzo[de]pyrano[3',4':6,7]indolizino[1,2-b]quinoline-10,13(9H,15H)-dione 165 mg of the compound prepared in (2) above and 179 mg of trione were reacted for 43 hours in the same manner as in Example 1-(5) and post-treated to produce 135 mg of the title compound.

mp: above 240° C. (decomposed). IRv$_{max}^{KBr}$ cm$^{-1}$: 3296, 2940, 2228, 1752, 1662, 1602. NMR(DMSO-d$_6$)δ: 0.86–0.90(3H, m), 1.81–1.91(2H, m), 1.93(3/2H, s), 1.94(3/2H, s), 2.16–2.34(2H, m), 3.38–3.51(2H, m), 5.20–5.31(2H, m), 5.43–5.44(2H, m), 5.61–5.66(1H, m), 6.55(1H, s), 7.37 (1/2H, s), 7.38(1/2H, s), 8.09(1H, d, J=8.8 Hz), 8.14(1H, d, J=8.8 Hz), 8.51–8.54(1H, m). MASS m/z; 470(M$^+$)

Example 24

Preparation of (9S)-1-amino-4-cyano-9-ethyl-2,3-dihydro-9-hydroxy-1H,12H-benzo[de]pyrano[3',4':6,7]indolizino[1,2-b]quinoline-10,13(9H,15H)-dione Hydrochloride

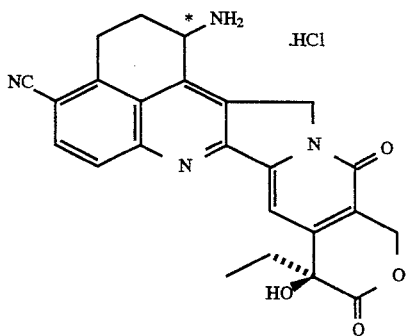

The compound prepared in Example 21-(3) (124 mg) above was reacted for 3 hours in the same manner as in Example 2 and post-treated to produce Isomer A (29 mg) and Isomer B (30 mg) of the title compound.

Isomer A mp: above 240° C. (decomposed). IR$v_{max}^{KBr}$ cm$^{-1}$: 3428, 2928, 2232, 1740, 1660, 1600. NMR(DMSO-d$_6$)δ: 0.89(3H, t, J=6.8 Hz), 1.87–1.91(2H, 2.2–2.4(1H, m), 2.6–2.7(1H, m), 3.4–3.6(2H, m), 5.18(1H, br), 5.46–5.51(3H, m), 5.96(1H, d, J=19 Hz), 6.58(1H, s), 7.42(1H, s), 8.17(1H, d, J=8.8 Hz), 8.22(1H, d, J=8.8 Hz), 8.79(1H, br). MASS m/z 428(M$^+$)

Isomer B mp: above 240° C. (decomposed). IR$v_{max}^{KBr}$ cm$^{-1}$: 2884, 2228, 1754, 1658, 1590. NMR(DMSO-d$_6$)δ: 0.88(3H, t, J=7.3 Hz), 1.83–1.94(2H, m), 2.26–2.33(1H, m), 2.54–2.68 (1H, m), 3.38–3.57(2H, m), 5.20(1H, br), 5.47–5.52(3H, m), 5.97(1H, d, J=19 Hz), 6.58(1H, s), 7.38(1H, s), 8.18(1H, d, J=8.8 Hz), 8.23(1H, d, J=8.8 Hz), 8.85(1H, br). MASS m/z: 428(M$^+$)

Example 25

Preparation of (9S)-9-ethyl-9-hydroxy2-sulfonyl-2,3-dihydro-1H,12H-benzo[de]pyrano[3',4':6,7]indolizino[1,2-b]quinoline-10,13(9H,15H)-dione

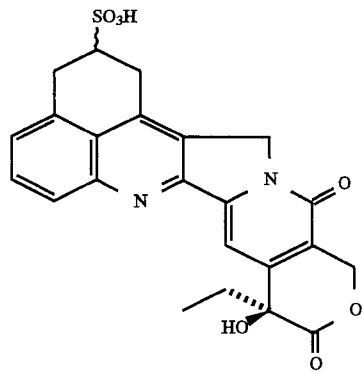

500 mg of 3-sulfonyl-8-amino-tetralone [Ann. 638, 43–56 (1960)] and 355 mg of trione was reacted for 16 hours in the same manner as in Example 17-(5). After cooling, the reaction mixture was concentrated, the residue was diluted with water to submit it to Diaion HP-20 column chromatography using 25% aqueous ethanol as an eluant to obtain fractions containing the target compound. The fractions were concentrated to produce 220 mg of the title compound.

mp: 190°–200° C. (decomposed). IR$v_{max}^{KBr}$ cm$^{-1}$: 1744, 1660, 1164, 1038. NMR(DMSO-d$_6$)δ: 0.89(t, 3H, J=7 Hz), 1.8–2.0(m, 2H), 2.9–3.6(m, 5H), 5.1–5.4(ABq, 2H), 5.43(s, 2H), 6.50(br, 1H), 7.31, 7.32(each s, 1H), 7.49(d, 1H, J=7 Hz), 7.73(t, 1H, J=7 Hz), 7.96(d, 1H, J=7 Hz). MASS m/z: 468(M$^+$)

Example 26

Preparation of (9S)-1,4-diamino-9-ethyl-1,2-dihydro-9-hydroxy-12H-thiino[4,3,2-de]pyrano[3',4':6,7]indolizino[1,2-b]quinoline-10,13(9H,15H)-dione Hydrochloride

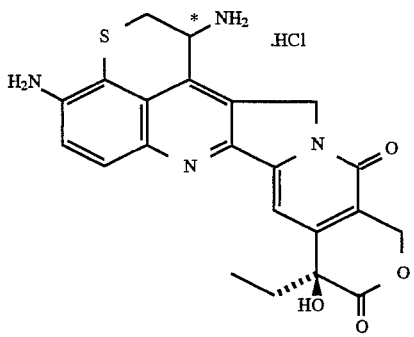

(1) 8-Acetylamino-5-benzyloxycarbonylamino-4-thiochromanone

To 40 ml of dichloromethane 570 mg of 8-acetylamino-5-amino-4-thiochromanone and 1 ml of pyridine were added. While stirring at 0° C., 0.69 ml of carbobenzoylchloride was added and the mixture was stirred for 1 hour. The reaction mixture was washed with dilute hydrochloric acid, water, and saturated brine in this order, and dried over anhydrous sodium sulfate. After evaporating the solvent, the residue was recrystallized from methanol to obtain 710 mg of the title compound.

NMR(CDCl$_3$)δ: 2.21(3H, s), 3.03(2H, m), 3.16(2H, m), 5.21(2H, s), 6.97(1H, br.s), 7.3–7.5(5H, m), 7.79(1H, d, J=8.8 Hz), 8.30(1H, d, J=8.8 Hz), 11.60(1H, br.s)

(2) 3,8-Diacetylamino-5-amino-4-thiochromanone

To 5 ml of a THF solution containing 168 mg of potassium-t-butoxide was added 5 ml of a THF solution containing 370 mg of the compound prepared in (1) above. After stirring for 5 minutes, 0.24 ml of n-butyl nitrite was added to the mixture, followed by further stirring for 1 hour at room temperature. After the addition of 20 ml of ether, the reaction mixture was stirred for another 1 hour. The deposited precipitate was collected by filtration, washed thoroughly with ether, and dissolved into a mixture of 20 ml of acetic acid and 20 ml of acetic anhydride. To the solution was slowly added about 200 mg of zinc powder at room temperature while stirring. After the addition, the stirring was continued for a further 0.5 hour. Insoluble substances were removed by filtration, the solvent was evaporated, and 20 ml of chloroform was added to the residue. The residue, after washing with water, saturated aqueous solution of sodium hydroxide, and saturated brine in this order, was dried over anhydrous sodium sulfate. After evaporating the solvent, the residue was subjected to silica gel column chromatography using a hexane-ethyl acetate (4:1) mixed solvent as an eluant to obtain fractions containing the target compound. The fractions were concentrated and the residue was dissolved in 20 ml of a mixed solvent of dioxane-methanol (1:1) and catalytically hydrogenated using 100 mg of palladium-on-carbon. After evaporating the solvent, the residue was subjected to silica gel column chromatography using a hexane-ethyl acetate (4:1) mixed solvent as an eluant to obtain fractions containing the target compound. The fractions were concentrated to produce 23 mg of the title compound.

NMR(CDCl$_3$)δ: 2.10(3H, s), 2.19(3H, s), 2.99(1H, t, J=13 Hz), 3.56(1H, dd, J=4 Hz,12 Hz), 4.79(1H, dt, J=4 Hz,13 Hz), 6.40(1H, d, J=8.8 Hz), 6.85(1H, m), 6.92(1H, d, J=4 Hz), 7.35(1H, d, J=8.8 Hz)

(3) (9S)-1,4-Diamino-9-ethyl-1,2-dihydro-9-hydroxy-12H-thiino[4,3,2-de]pyrano[3',4':6,7]indolizino[1,2-b]quinoline-10,13(9H,15H)-dione Hydrochloride 23 mg of the compound prepared in (2) above and 20 mg of trione was added to 5 ml of toluene. To this was added a catalytic amount of PPTS to react the mixture in a Deanstark apparatus under heating with refluxing for 20 hours. The reaction mixture was cooled and the solvent was evaporated. The residue was subjected to silica gel column chromatography using a chloroform-methanol (95:5) mixed solvent as an eluant to obtain fractions containing the target compound. 4 ml of 6N hydrochloric acid was added to the residue obtained by concentrating the fractions and the mixture was stirred for 1.5 hours. After concentrating the resulting mixture, 4 ml of water was added to remove insoluble substances by filtration. The filtrate was purified with HPLC (CAPCELL PAK C18) using a mixture of acetonitrile-water-1N hydrochloric acid (20:80:1) to obtain 10 mg of Isomer A and 7.4 mg of Isomer B of the title compound.

Isomer A mp: above 220° C. (decomposed). NMR(DMSO-d$_6$)δ: 0.88(3H, t, J=7.3 Hz), 1.86(2H, m), 3.34(1H, d, J=14.0 Hz), 3.50(1H, dd, J=14.0 Hz, 3.2 Hz), 5.29(1H, m), 5.36,5.76(2H, ABq, J=19.5 Hz), 5.43(2H, s), 6.11(2H, s), 6.49(1H, s), 7.22(1H, s), 7.42(1H, d, J=9.3 Hz), 7.82(1H, d, J=9.3 Hz), 8.66(3H, m)

Isomer B mp: above 220° C. (decomposed). NMR(DMSO-d$_6$)δ: 0.88(3H, t, J=7.3 Hz), 1.87(2H, m), 3.35(1H, d, J=13.7 Hz), 3.48(1H, dd, J=13.7 Hz, 3.0 Hz), 5.28(1H, m), 5.35,5.74(2H, ABq, J=19.5 Hz), 5.43(2H, s), 6.11(2H, s), 6.49(1H, s), 7.22(1H, s), 7.41(1H, d, J=9.3 Hz), 7.82(1H, d, J=9.3 Hz), 8.61(3H, m)

Example 27

Preparation of (9S)-3-(2-acetylaminoethyl)-9-ethyl-1,2-dihydro-9-hydroxy-4-methyl-3H,12H-pyrano[3',4':6,7]indolizino[1,2-c]benzo[ij][2,7]naphthylidine-10,13(9H,15H)-dione

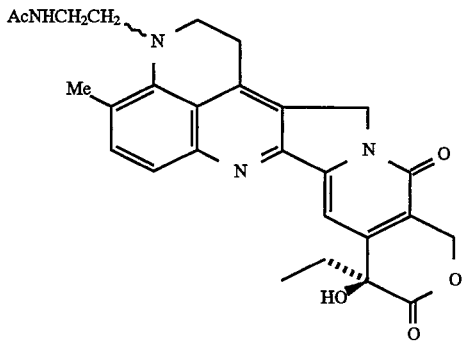

(1) 5-Acetylamino-8-methyl-2,3-dihydroquinoline-4-one

In a mixed solvent of 20 ml of dichloromethane and 1.3 ml of pyridine was dissolved 2.0 gm of 5-amino-8-methyl-2,3-dihydroquinoline-4-one. 1.2 ml of acetyl chloride was added to the solution under ice-cooling while stirring, followed by further stirring for 4 hours. After the addition of water, the reaction mixture was extracted with chloroform, washed with saturated brine, and dried over anhydrous sodium sulfate. After evaporating the solvent, the residue was crystallized in ether to obtain 1.24 gm of the title compound.

NMR(CDCl$_3$)δ: 2.01(s, 3H), 2.20(s, 3H), 2.72(t, 2H, J=7 Hz), 3.61(t, 2H, J=7 Hz), 7.19(d, 1H, J=8 Hz), 7.94(d, 1H, J=8 Hz)

(2) 5-Acetylamino-1-cyanomethyl-8-methyl-2,3-dihydroquinoline-4-one

The compound prepared in (1) above (1.95 gm) was dissolved into 40 ml of DMF, and 6 ml of bromoacetonitrile was added to the solution. After heating under reflux for 3 hours, the reaction mixture was concentrated, and chloroform was added to the residue. The residue, after washing with saturated brine, was dried over anhydrous sodium sulfate. After evaporating the solvent, the residue was subjected to silica gel column chromatography using a chloroform-methanol (100:1) mixed solvent as an eluant to obtain fractions containing the target compound. The fractions were concentrated to produce 605 mg of the title compound.

mp: 190°–193° C. IRv$_{max}^{KBr}$ cm$^{-1}$: 1696, 1644, 1506, 1392, 1248. NMR(CDCl$_3$)δ: 2.22(s, 3H), 2.29(s, 3H), 2.93(t, 2H, J=6.5 Hz), 3.68(t, 2H, J=6.5 Hz), 4.01(s, 2H), 7.38(d, 1H, J=8 Hz), 8.43(d, 1H, J=8 Hz). MASS m/z: 257(M$^+$)

(3) 5-Acetylamino-1-(2-aminoethyl)-8-methyl-2,3-dihydroquinoline-4-one

The compound prepared in (2) above (650 mg) was dissolved into a mixed solvent of 10 ml of acetic acid and 30 ml of acetic anhydride. The mixture was catalytically hydrogenated with the addition of 2 ml of Raney nickel. After removing the catalyst by filtration, the reaction mixture was concentrated and chloroform was added to the residue, which was washed with saturated aqueous solution of sodium bicarbonate and saturated brine, and dried over anhydrous sodium sulfate. After evaporating the solvent, the residue was recrystallized from chloroform and ether to obtain 510 mg of the title compound.

mp: 151°–153° C. (decomposed). IRv$_{max}^{KBr}$ cm$^{-1}$: 1690, 1646, 1520. NMR(CDCl$_3$)δ: 2.00(s, 3H), 2.21(s, 3H), 2.26 (s, 3H), 2.76(t, 2H, J=7 Hz), 3.14(t, 2H, J=7 Hz), 3.4–3.7(m, 4H), 5.98(br, 1H), 7.30(d, 1H, J=8 Hz), 8.27(d, 1H, J=8 Hz). MASS m/z: 303(M$^+$)

(4) 5-Amino-1-(2-aminoethyl)-8-methyl-2,3-dihydroquinoline-4-one

The reaction was carried out in the same manner as in Example 1-(4), except that 510 mg of the compound prepared in (1) above was used instead of 2,8-diacetylamino-1-tetralone of Example 1-(4), and post-treated to produce 220 mg of the title compound.

NMR(CDCl$_3$)δ: 1.99(s, 3H), 2.16(s, 3H), 2.6–2.9(m, 4H), 3.3–3.7(m, 4H), 5.8–6.8(br, 1H), 6.20(d, 1H, J=8 Hz), 7.04(d, 1H, J=8 Hz). MASS m/z: 261(M$^+$)

(5) (9S)-3-(2-Acetylaminoethyl)-9-ethyl-1,2-dihydro-9-hydroxy-4-methyl-3H,12H-pyrano[3',4':6,7]indolizino[1,2-c]benzo[ij][2,7]naphthyridine-10,13(9H,15H)-dione 210 mg of the compound prepared in (2) above and 230 mg of trione were reacted for 7 hours in the same manner as in Example 17-(5) and post-treated to produce 195 mg of the title compound.

mp: 155°–165° C. (decomposed). NMR(DMSO-d$_6$)δ: 0.88(t, 3H, J=7 Hz), 1.7–2.0(m, 2H), 1.82(s, 3H), 2.47(s, 3H), 2.9–3.1(m, 2H), 3.2–3.3(m, 2H), 3.4–3.7(m, 4H), 5.26 (s, 2H), 5.3–5.5(m, 2H), 7.34(s, 1H), 7.67(d, 1H, J=7 Hz), 7.74(d, 1H, J=7 Hz) 8.0–8.1(br.s, 1H). MASS m/z: 488(M$^+$)

Example 28

Preparation of (9S)-3-(2-aminoethyl)-9-ethyl-1,2-dihydro-9-hydroxy-4-methyl-3H,12H-pyrano[3',4':6,7]indolizino[1,2-c]benzo[ij][2,7]naphthyridine-10,13(9H,15H)dione

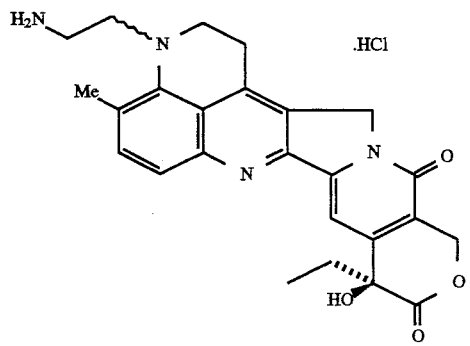

The compound prepared in Example 27-(5) (190 mg) was reacted in the same manner as in Example 2 and post-treated to produce 120 mg of the title compound.

mp: 210°–230° C. (decomposed). IRv$_{max}^{KBr}$ cm$^{-1}$: 1746, 1660 1594. NMR(DMSO-d$_6$)δ: 0.88(t, 3H, J=7.5 Hz), 1.8–1.9(m, 2H), 2.49(s, 3H), 3.1–3.5(m, 8H), 5.26(s, 2H), 5.43(s, 2H), 7.32(s, 1H), 7.69(d, 1H, J=9 Hz), 7.78(d, 1H, J=9 Hz), 8.1–8.3(br.s, 3H). MASS m/z: 446(M$^+$)

Example 29

Preparation of (9S)-4-chloro-9-ethyl-2,3-dihydro-9-hydroxy-3-dimethylamino-1H,12H-benzo[de]pyrano [3',4':6,7]indolizino[1,2-b]quinoline-10,13(9H,15H) dione Hydrochloride

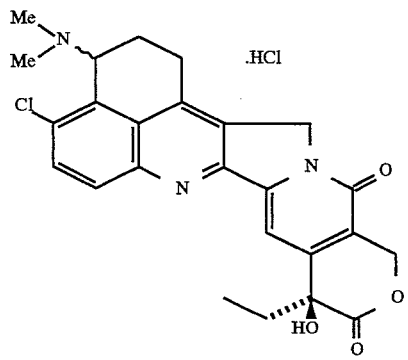

To a solution of 44 mg of Isomer B prepared in Example 14 dissolved in 5 ml of 50% aqueous methanol were added 0.5 ml of 35% aqueous solution of formalin and 50 mg of 10% palladium-on-carbon to effect catalytic hydrogenation. After the reaction, the catalyst was removed by filtration, and the solvent was evaporated. 4 ml of water was added to remove insoluble substance by filtration. The filtrate was purified with HPLC (CAPCELL PAK C18) using a mixture of acetonitrile-water-1N hydrochloric acid (20:80:1) to obtain 8 mg of the title compound.

NMR(DMSO-d$_6$)δ: 0.89(3H, t, J=7.3 Hz), 1.88(2H, m), 2.2–2.4(1H, m), 2.4–2.6(1H, m), 2.67(3H, m), 3.06(3H, m), 3.3–3.5(2H, m), 5.19(1H, m), 5.21, 5.43(2H, ABq, J=18.6 Hz), 5.45(2H, s), 6.56(1H, s), 7.37(1H, s), 8.03(1H, d, J=9.3 Hz), 8.31(1H, d, J=9.3 Hz)

Example 30

Preparation of (9S)-1-acetylamino-4-amino-9-ethyl-2,3-dihydro-9-hydroxy-1H,12H-benzo[de]pyrano[3', 4':6,7]indolizino[1,2-b]quinoline-10,13(9H,15H)-dione

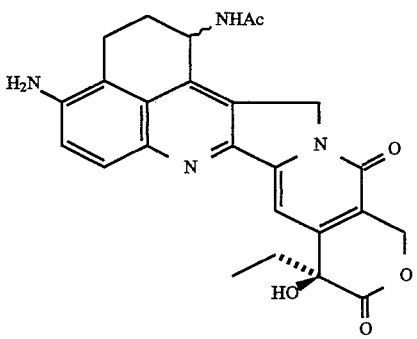

(1) 2,5,8-Triacetylamino-1-tetralone

The reaction was carried out in the same manner as in Example 1-(2), except that 1.65 gm of 5,8-diacetylamino-1-tetralone was used instead of 8-acetylamino-1-tetralone of Example 1-(2). Crude 5,8-diacetylamino-2-hydroxyimino-1-tetralone which was obtained by the post-treatment was reacted in the same manner as in Example 1-(3) and post-treated to produce 950 mg of the title compound.

IRv$_{max}^{KBr}$ cm$^{-1}$: 3280, 1660, 1596, 1516. NMR(CDCl$_3$) δ: 1.79–2.02(1H, m), 2.11(3H, s), 2.18(3H, s), 2.23(3H, s), 2.4–3.0(3H, m), 4.54–4.69(1H, m), 7.60(1H, d, J=9.0 Hz), 8.55(1H, d, J=9.0 Hz). MASS m/z: 317(M$^+$)

(2) 2-Acetylamino-5,8-diamino-1-tetralone

The reaction was carried out in the same manner as in Example 1-(4), except that 500 mg of the compound prepared in (1) above was used instead of 2,8-diacetylamino-1-tetralone of Example 1-(4), and post-treated to produce 290 mg of the title compound.

IRv$_{max}^{KBr}$ cm$^{-1}$: 3436, 3352, 3296, 2444, 1626, 1556. NMR(DMSO-d$_6$)δ: 1.74–1.87(1H, m), 1.90(3H, s), 2.14–2.16(1H, m), 2.54–2.77(2H, m), 4.41–4.47(1H, m), 6.48(1H, d, J=8.3 Hz), 6.83(1H, d, J=8.3 Hz), 8.04(1H, d, J=7.8 Hz). MASS m/z: 233 (M$^+$)

(3) (9S)-1-Acetylamino-4-amino-9-ethyl-2,3-dihydro-9-hydroxy-1H,12H-benzo[de]pyrano[3',4':6,7]indolizino[1,2-b]quinoline-10,13(9H,15H)-dione 234 mg of the compound prepared in (2) above and 261 mg of trione were dissolved in 30 ml of acetic acid and heated under reflux for 14 hours in a nitrogen atmosphere. The reaction product was post-treated in the same manner as in Example 1-(5) to produce 134 mg of the title compound.

mp: above 240° C. (decomposed). IRv$_{max}^{KBr}$ cm$^{-1}$: 3380, 2984, 2940, 1748, 1662, 1602. NMR(DMSO-d$_6$)δ: 0.89(3H, t, J=7.2 Hz), 1.82–1.92(2H, m), 1.93(3/2H, s), 1.94(3/2H, s), 2.08–2.09(2H, m), 3.08(2H, br), 5.16–5.26(2H, m), 5.39–5.46(2H, m), 5.53–5.56(1H, m), 6.51(1H, s), 7.32(2H, s), 7.96(1H, d, J=9.5 Hz), 7.99(1H, d, J=8.7 Hz), 8.54(1H, t, J=8.7 Hz). MASS m/z: 458(M$^+$)

Example 31

Preparation of (9S)-1,4-diamino-9-ethyl-2,3-dihydro-9-hydroxy-1H,12H-benzo[de]pyrano[3',4':6,7]indolizino[1,2-b]quinoline-10,13(9H,15H)-dione Hydrochloride

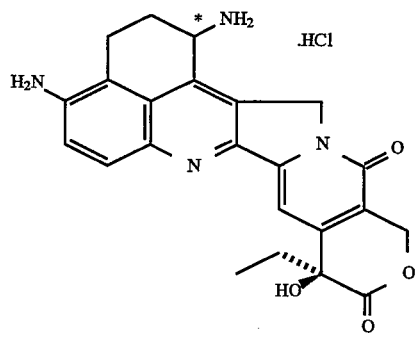

The compound prepared in Example 21-(3) (113 mg) was reacted for 6 hours in the same manner as in Example 2 and post-treated to produce Isomer A (28 mg) and Isomer (B) (28 mg) of the title compound.

Isomer A mp: above 240° C. (decomposed). IRv$_{max}^{KBr}$ cm$^{-1}$: 3392, 3232, 2936, 1742, 1652, 1590. NMR(DMSO-d$_6$)δ: 0.89(3H, t, J=6.8 Hz), 1.82–1.92(2H, m), 2.03–2.09(1H, m), 2.67–2.93(2H, m), 4.97(1H, br), 5.32–5.46(3H, m), 5.74–5.81(1H, m), 6.47(1H, s), 7.21(1H, s), 7.39(1H, d, J=8.8 Hz), 7.83(1H, d, J=8.8 Hz), 8.60(1H, br). MASS m/z: 418(M$^+$)

Isomer B mp: above 240° C. (decomposed). IRv$_{max}^{KBr}$ cm$^{-1}$: 3436, 3232, 1746, 1658, 1592. NMR(DMSO-d$_6$)δ: 0.89(3H, t, J=6.8 Hz), 1.81–1.92(2H, m), 2.03–2.09(1H, m), 2.68–2.95 (2H, m), 4.99(1H, br), 5.37–5.47(3H, m), 5.81(1H, d, J=19 Hz), 7.23(1H, s), 7.43(1H, d, J=8.8 Hz), 7.85(1H, d, J=8.8 Hz), 8.64(1H, br). MASS m/z: 418(M$^+$)

Example 32

Preparation of (9S)-1-acetylamino-9-ethyl-2,3-dihydro-9-hydroxy-4-methyl-1H,12H-benzo[de]pyrano[3',4':6,7]indolizino[1,2-b]quinoline-10,13(9H,15H)-dione

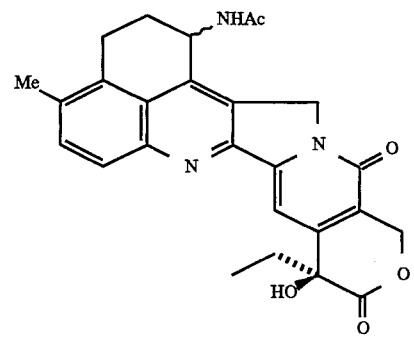

(1) Methyl (2'-tolyl)acetate

To a solution of 25 gm of o-tolylacetic acid in 350 ml of methanol 1 ml of concentrated hydrochloric acid was added. The mixture was heated under reflux overnight. 200 ml of water was added to the residue obtained by removing the solvent. The precipitate was extracted with chloroform and the extract was washed with saturated brine, and dried over anhydrous magnesium sulfate. The solvent was removed to obtain 27.2 gm of the title compound.

NMR(CDCl$_3$)δ: 2.30(3H, s), 3.64(2H, s), 3.68(3H, s), 7.17(4H, s)

(2) Methyl 4-(2'-tolyl)-3-butenate

The solution of 13.1 gm of the compound prepared in (1) above in 100 ml of toluene was cooled to −65° C., and to this was dropwise added over 1 hour 80 ml of 1M diisobutylaluminum hydride in toluene and the mixture was stirred for 1 hour at the same temperature, following which the reaction was terminated by the addition of methanol. The reaction mixture was diluted with ethyl acetate, washed with 10% aqueous solution of hydrochloric acid, water, and saturated brine in this order, and dried over anhydrous magnesium sulfate. After removing the solvent, the residue was dissolved into 100 ml of benzene. To this solution was added 26.5 gm of methyl(triphenylphosphoranilidene)acetate, and the mixture was stirred overnight at room temperature. The solvent was evaporated, and a mixed solvent of ethyl acetate-n-hexane (1:9) was added to the residue to remove insoluble substance by filtration. The filtrate was concentrated and the residue was subjected to silica gel column chromatography using an ethyl acetate-n-hexane (1:9) mixed solvent as an eluant to obtain fractions containing the target compound. The fractions were concentrated to produce 12.7 mg of the title compound.

NMR(CDCl$_3$)δ: 2.27(3H, s), 3.46–3.54(2H, m), 3.70(3H, s), 5.70(1H, d, 15.5 Hz), 6.95–7.24(5H, m)

(3) 4-(2'-Tolyl)butyric Acid

A solution of 12.6 gm of the compound prepared in (2) above in 200 ml of methanol was catalytically hydrogenated for 20 minutes with 10% palladium-on-carbon. After the catalyst was removed by filtration, the reaction liquid was concentrated to a volume of 150 ml. 70 ml of 1N sodium hydroxide solution was added to the concentrate, followed by heating at 50° C. for 1 hour while stirring. After cooling to room temperature, the reaction product was adjusted below pH 1 with hydrochloric acid while ice-cooling. The precipitate was extracted with chloroform, washed with saturated brine, and dried over anhydrous magnesium sulfate. The solvent was removed to obtain 11.4 gm of the title compound.

mp: 54°–56° C. (decomposed) $IRv_{max}^{KBr}$ cm$^{-1}$: 3416, 2944, 1748, 1660, 1602. NMR(CDCl$_3$)δ: 1.83–1.99(2H, m), 2.31(3H, s), 2.34–2.75(4H, m), 7.12(4H, m). MASS m/z: 178(M$^+$)

(4) 5-Methyl-1-tetralone

To 120 gm of polyphosphoric acid heated at 70° C. 10.0 gm of the powder prepared in (3) above was added over 30 minutes, and the mixture was stirred for 20 minutes at the same temperature. The reaction mixture was added to 600 ml of ice water to collect the precipitate by filtration, followed by washing with water. The powder thus obtained was dissolved into ethyl acetate, washed with brine, and dried over anhydrous magnesium sulfate. The solvent was removed to obtain 8.19 gm of the title compound.

mp: 43°–47° C. (decomposed). $IR_{max}^{KBr}$ cm$^{-1}$: 3452, 2952, 1676, 1592, 1464. NMR(CDCl$_3$)δ: 2.07–2.27(2H, m), 2.31(3H, s), 2.57–2.93(4H, m), 7.11–7.33(2H, m), 7.89–7.98(1H, m). MASS m/z: 160(M$^+$)

(5) 5-Methyl-8-nitro-1-tetralone

A solution of 8.1 gm of the compound obtained in (4) above in 70 ml of concentrated sulfuric acid was cooled to −5° C. To this solution was dropwise added a solution of 5.37 gm of potassium nitrate in 50 ml of concentrated sulfuric acid while controlling the temperature below 5° C., followed by stirring for 30 minutes at the same temperature. The reaction mixture was poured to 600 ml of ice-cold water and extracted with chloroform, washed with saturated aqueous sodium bicarbonate and saturated brine, and dried over anhydrous magnesium sulfate. After evaporating the solvent, the residue was subjected to silica gel column chromatography using an ethyl acetate-n-hexane (1:15) mixed solvent as an eluant to obtain fractions containing the target compound. The fractions were concentrated to produce 5.82 gm of the title compound.

mp: 104°–107° C. $IRv_{max}^{KBr}$ cm$^{-1}$: 3452, 2964, 1690, 1596. NMR(CDCl$_3$)δ: 2.17–2.22(2H, m), 2.37(3H, s), 2.69–2.72(2H, m), 2.89(2H, t, J=5.9 Hz), 7.25(1H, d, J=8.3 Hz), 7.40(1H, d, J=7.8 Hz). MASS m/z: 205(M$^+$)

(6) 8-Acetylamino-5-methyl-1-tetralone

The compound prepared in (5) above (2.5 gm) was dissolved into a mixed-solvent of 50 ml of acetic acid and 50 ml of acetic anhydride. The mixture was catalytically hydrogenated for 1 hour in a hydrogen stream with the addition of 800 mg of 10% palladium-on-carbon. After removing the catalyst by filtration, the reaction mixture was concentrated. The residue was subjected to silica gel column chromatography using chloroform as an eluant to obtain fractions containing the target compound. The fractions were concentrated to produce 2.22 gm of the title compound.

mp: 92°–94° C. $IRv_{max}^{KBr}$ cm$^{-1}$: 3512, 3176, 2940, 1690, 1660, 1604. NMR(CDCl$_3$)δ: 1.95–2.18(2H, m), 2.22(3H, s), 2.25(3H, s), 2.61–2.93(4H, m), 7.33(1H, d, J=8.5 Hz), 8.51(1H, d, J=8.5 Hz). MASS m/z: 217(M$^+$)

(7) 2,8-Diacetylamino-5-methyl-1-tetralone

The reaction was carried out in the same manner as in Example 1-(2), except that 1 gm of 8-acetylamino-5-methyl-1-tetralone was used instead of 8-acetylamino-1-tetralone of Example 1-(2). Crude 8-acetylamino-2-hydroxyimino-5-methyl-1-tetralone which was obtained by the post-treatment was reacted in the same manner as in Example 1-(3) and post-treated to produce 476 mg of the title compound.

mp: 195°–198° C. (decomposed). $IRv_{max}^{KBr}$ cm$^{-1}$: 3312, 2928, 1712, 1638, 1596, 1520. NMR(CDCl$_3$)δ: 1.74–1.98 (1H, m), 2.11(3H, s), 2.22(3H, s), 2.24(3H, s), 2.66–3.03 (3H, m), 4.52–4.79(1H, m), 6.5(1H, br), 7.36(1H, d, J=8.5 Hz), 8.50(1H, d, 8.5 Hz). MASS m/z: 274(M$^+$)

(8) 2-Acetylamino-8-amino-5-methyl-1-tetralone

The reaction was carried out in the same manner as in Example 1-(4), except that 400 mg of the compound prepared in (7) above was used instead of 2,8-diacetylamino-1-tetralone of Example 1-(4), and post-treated to produce 265 mg of the title compound.

mp: 192°–194° C. (decomposed). $IRv_{max}^{KBr}$ cm$^{-1}$: 3460, 3360, 2924, 1618, 1566, 1536. NMR(CDCl$_3$)δ: 1.76–1.87 (1H, m), 2.10(3H, s), 2.16(3H, s), 2.63–2.69(1H, m), 2.91–2.97(2H, m), 4.55–4.56(1H, m), 6.55(1H, d, J=8.3 Hz), 7.13(1H, d, J=8.3 Hz). MASS m/z: 232(M$^+$)

(9) (9S)-1-Acetylamino-9-ethyl-2,3-dihydro-9-hydroxy-4-methyl-1H,12H-benzo[de]pyrano[3',4':6,7]indolizino[1,2-b]quinoline-10,13(9H,15H)-dione 200 mg of the compound prepared in (8) above and 227 mg of trione were reacted for 23 hours in the same manner as in Example 1-(5) and the reaction product was post-treated to produce 287 mg of the title compound.

mp: above 270° C. (decomposed). $IRv_{max}^{KBr}$ cm$^{-1}$: 3428, 2944 1754 1660, 1608, 1556. NMR(DMSO-d$_6$)δ: 0.86–0.90 (3H, m), 1.75–1.89(2H, m), 1.91(3/2H, s), 1.92(3/2H, s), 2.11–2.14(2H, m), 2.47(3/2H, s), 2.48(3/2H, s), 3.08–3.11 (2H, m), 5.19–5.21(2H, m), 5.43(2H, s), 5.52–5.57(1H, m), 6.50(1/2H, s), 6.51(1/2H, s), 7.31(1H, s), 7.71(1H, d, J=8.3 Hz), 7.94(1H, d, J=8.3 Hz), 8.47(1H, t, J=8.3 Hz). MASS m/z: 459(M$^+$)

Example 33

Preparation of (9S)-1-amino-9-ethyl-2,3-dihydro-9-hydroxy-4-methyl-1H,12H-benzo[de]pyrano[3',4':6,7]indolizino[1,2-b]quinoline-10,13(9H,15H)-dione Hydrochloride

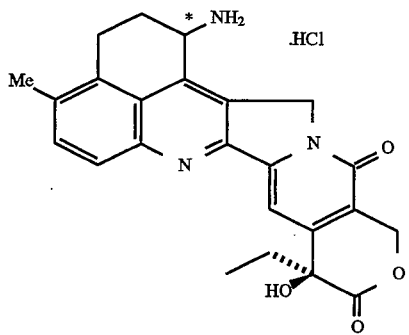

The compound prepared in Example 32-(9) (150 mg) was reacted for 7 hours in the same manner as in Example 2 and post-treated to produce Isomer A (58 mg) and Isomer B (62 mg) of the title compound.

Isomer A mp: above 250° C. (decomposed). IR$v_{max}^{KBr}$ cm$^{-1}$: 3432, 2936, 1746, 1658, 1594. NMR(DMSO-d$_6$)δ: 0.90(3H, t, J=6.8 Hz), 1.83–1.91(2H, m), 2.15–2.22(1H, m), 2.56–2.59 (1H, m), 3.12–3.28(2H, m), 5.09(1H, br), 5.40–5.45(3H, m), 5.90(1H, d, J=19 Hz), 6.52(1H, s), 7.34(1H, s), 7.76(1H, d, J=8.8 Hz), 8.01(1H, d, J=8.8 Hz), 8.73(3H, br). MASS m/z: 417(M$^+$)

Isomer B mp: above 250° C. (decomposed). IR$v_{max}^{KBr}$ cm$^{-1}$: 3448, 2936, 1746, 1658, 1596. NMR(DMSO-d$_6$)δ: 0.89(3H, t, J=6.8 Hz), 1.83–1.93(2H, m), 2.17(1H, br), 2.61–2.68(1H, m), 3.10–3.21(2H, m), 5.10(1H, br), 5.43–5.48(3H, m), 5.93(1H, d, J=19 Hz), 7.35(1H, s), 7.78(1H, d, J=8.8 Hz), 8.02(1H, d, J=8.8 Hz), 8.80(3H, br). MASS m/z: 417(M$^+$)

Example 34

Preparation of (10S)-1-acetylamino-10-ethyl-1,2,3,4-tetrahydro-10-hydroxy-13H-cyclohepto[de]pyrano[3',4':6,7]indolizino[1,2-b]quinoline-11,14 (10H;16H)-dione

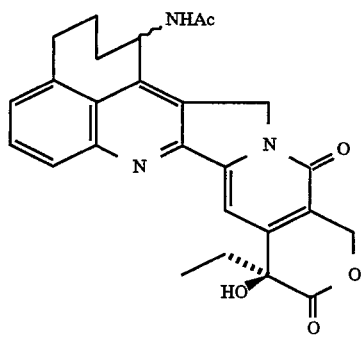

(1) 1-Acetylamino-6,7,8,9-tetrahydro-5H-benzocycloheptene 8.7 gm of 1-nitro-6,7,8,9-tetrahydro-5H-benzocycloheptene [J. Am. Chem. Soc., 5820 (9169)] was dissolved into a mixed solvent of 150 ml of acetic anhydride and 50 ml of acetic acid. The mixture was catalytically hydrogenated with the addition of 10 ml of raney nickel. After removing the catalyst by filtration, the reaction mixture was concentrated, the residue was washed with saturated aqueous solution of sodium bicarbonate and saturated brine, and dried over anhydrous sodium sulfate. The product was concentrated to produce 6.17.gm of the title compound.

NMR(CDCl$_3$)δ: 1.5–1.9(m, 6H), 2.15, 2.20(each s, 3H), 2.6–2.9(m, 4H), 6.9–7.4(m, 3H). MASS m/z: 203(M$^+$)

(2) 1-Acetylamino-6,7,8,9-tetrahydro-5H-benzocycloheptene-9-one

The reaction was carried out in the same manner as in Example 1-(1), except that 200 mg of the compound prepared in (1) above was used instead of 1-acetylaminotetraline of Example 1-(1). The reaction product was post-treated to produce 55 mg of the title compound.

mp: 155°–162° C. NMR(CDCl$_3$)δ: 1.5–2.0(m, 6H), 2.17 (s, 3H), 2.6–2.9(m, 4H), 6.93(d, 1H, J=8 Hz), 7.38(t, 1H, J=8 Hz), 8.30(d, 1H, J=8 Hz). MASS m/z: 217(M$^+$)

(3) 1,8-Diacetylamino-6,7,8,9-tetrahydro-5H-benzocycloheptene-9-one

The reaction was carried out in the same manner as in Example 1-(2), except that 270 mg of the compound prepared in (2) above was used instead of 8-acetylamino-1-tetralone of Example 1-(2). The reaction mixture obtained by the post-treatment was further reacted in the same manner as in Example 1-(3) and post-treated to produce 126 mg of the title compound.

mp: 220°–223° C. (decomposed). IR$v_{max}^{KBr}$ cm$^{-1}$: 1722, 1682, 1616, 1548. NMR(CDCl$_3$)δ: 2.08(s, 3H), 2.19(s, 3H), 1.5–2.4(m, 4H) 2.7–3.1(m, 2H), 4.7–4.9(m, 1H), 6.1–6.3 (br.s, 1H), 6.94(d, 1H, J=8 Hz), 7.34(t, 1H, J=8 Hz), 8.32(d, 1H, J=8 Hz), 9.01(br.s, 1H). MASS m/z: 274(M$^+$)

(4) 8-Acetylamino-1-amino-6,7,8,9-tetrahydro-5H-benzocycloheptene-9-one

The reaction was carried out in the same manner as in Example 1-(4), except that 115 mg of the compound prepared in (3) above was used instead of 2,8-diacetylamino-1-tetralone of Example 1-(4). The product was post-treated to produce 90 mg of the title compound.

NMR(CDCl$_3$)δ: 2.04(s, 3H), 1.5–1.7(m, 2H), 2.0–3.2(m, 4H), 4.9–5.1(m, 1H), 5.98(br.s, 1H), 6.53(d, 1H, J=8 Hz), 6.54(d, 1H, J=8 Hz), 6.72(br.s, 1H), 7.23(t, 1H, J=8 Hz)

(5) (10S)-1-Acetylamino-10-ethyl-1,2,3,4-tetrahydro-10-hydroxy-13H-cyclohepto[de]pyrano[3',4':6,7]indolizino[1,2-b]quinoline-11,14(10H,16H)-dione The compound prepared in (4) above (90 mg) and 105 mg of trione were reacted for 21 hours in the same manner as in Example 1-(5) and the product was post-treated to obtain 72 mg of the title compound.

mp: 203°–206° C. (decomposed). IR$v_{max}^{KBr}$ cm$^{-1}$: 1748, 1660, 1600, 1160. NMR(CDCl$_3$)δ: 0.96, 1.03(each t, 3H, J=7 Hz), 1.5–4.0(m, 6H), 2.15, 2.27(each s, 3H), 5.0–6.0(m, 2H), 7.3–8.2 (m, 4H). MASS m/z: 459(M$^+$)

Example 35

Preparation of (10S)-1-amino-10-ethyl-1,2,3,4-tetrahydro-10-hydroxy-13H-cyclohepto[de]pyrano[3',4':6,7]indolizino-[1,2-b]quinoline-11,14(10H,16H)-dione Hydrochloride

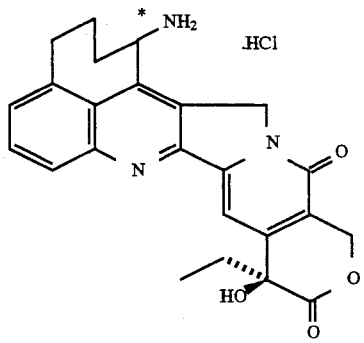

The compound prepared in Example 34-(5) (65 mg) was reacted for 4 hours in the same manner as in Example 2 and the product was post-treated to obtain Isomer A (17 mg) and Isomer B (21 mg) of the title compound.

Isomer A mp: 200°–220° C. (decomposed). IR$\nu_{max}^{KBr}$ cm$^{-1}$: 1746, 1660, 1600, 1164. NMR(DMSO-d$_6$)δ: 0.88(t, 3H, J=7 Hz), 1.7–2.0(m, 2H), 2.0–3.5(m, 6H), 5.15(s, 1H), 5.46(s, 2H), 5.53, 5.73(ABq, 2H, J=19 Hz), 6.56(s, 1H), 7.35(s, 7.63(d, 1H, J=8 Hz), 7.79(t, 1H, J=8 Hz), 8.09(d, 1H, J=8 Hz), 8.79(br.s, 3H). MASS m/z: 417(M$^+$)

Isomer B mp: 210°–230° C. (decomposed). IR$\nu_{max}^{KBr}$ cm$^{-1}$: 1744, 1664, 1600, 1160. NMR(DMSO-d$_6$)δ: 0.88(t, 3H, J=7 Hz), 1.7–2.0(m, 2H), 2.0–3.5(m, 6H), 5.0–5.2(m, 1H), 5.46(s, 2H), 5.54, 5.72(ABq, 2H, J=19 Hz), 6.56(s, 1H), 7.35(s, 1H), 7.62(d, 1H, J=8 Hz), 7.77(t, 1H, J=8 Hz), 8.09(d, 1H, J=8 Hz), 8.61(br.s, 3H). MASS m/z: 417(M$^+$)

Example 36

Preparation of (9S)-9-ethyl-2,3-dihydro-3-(1,3-dioxoisoindoline-2-yl)-9-hydroxy-4-methyl-1H,12H-benzo[de]pyrano[3',4':6,7]indolizino[1,2-b]quinoline-10,13(9H,15H)-dione

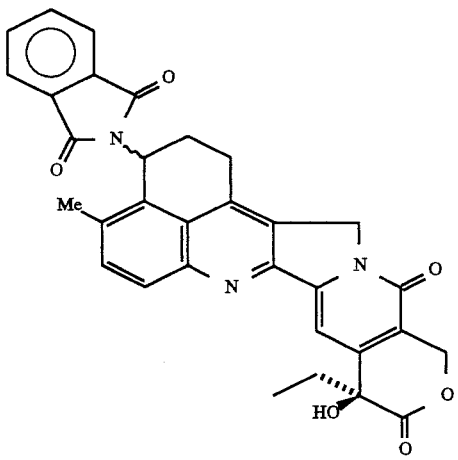

(1) 4-Azide-5-methyl-8-nitro-1-tetralone

The reaction was carried out in the same manner as in Example 13-(9), except that 410 mg of 5-methyl-8-nitro-1-tetralone was used instead of 5-fluoro-8-nitro-1-tetralone of Example 13-(9). The product was post-treated to produce 490 mg of the title compound.

NMR(CDCl$_3$)δ: 2.33–2.50(2H, m), 2.55(3H, s), 2.69–2.75(1H, m), 2.98–3.07(1H, m), 5.07(1H, t, J=2.9 Hz), 7.42(1H, d, J=7.8 Hz), 7.54(1H, d, J=8.8 Hz)

(2) 5-Methyl-8-nitro-4-(1,3-dioxoisoindoline-2-yl)-1-tetralone

The reaction was carried out in the same manner as in Example 13-(9), except that 490 mg of the compound prepared in (1) above was used instead of 4-azide-5-fluoro-8-nitro-1-tetralone of Example 13-(9). The reaction product was post-treated to produce 366 mg of the title compound.

mp: 220°–230° C. IR$\nu_{max}^{KBr}$ cm$^{-1}$: 3456, 3084, 2940, 1770, 1712, 1596. NMR(CDCl$_3$)δ: 2.26(3H, s), 2.38–2.44 (1H, m), 2.55–2.65(1H, m), 2.72–2.79(1H, m), 2.93–3.02 (1H, m), 5.70–5.72(1H, m), 7.39(1H, d, J=8.3 Hz), 7.42(1H, d, J=8.3 Hz), 7.74–7.84(4H, m). MASS m/z: 350(M$^+$)

(3) 8-Amino-5-methyl-4-(1,3-dioxoisoindoline-2-yl)-1-tetralone

The reaction was carried out in the same manner as in Example 13-(10), except that 145 mg of the compound prepared in (2) above was used instead of 5-fluoro-8-nitro-4-(1,3-dioxoisoindoline-2-yl)-1-tetralone of Example 13-(10). The reaction product was post-treated to produce 75 mg of the title compound.

IR$\nu_{max}^{KBr}$ cm$^{-1}$: 3456, 3344, 2952, 1770, 1710, 1622. NMR(CDCl$_3$)δ: 2.02(3H, s), 2.25–2.32(1H, m), 2.41–2.50 (1H, m), 2.58–2.64(1H, m), 2.88–2.98(1H, m), 5.60–5.62 (1H, m), 6.58(1H, d, J=8.3 Hz), 7.05(1H, d, J=8.3 Hz), 7.70–7.81(4H, m). MASS m/z: 320(M$^+$)

(4) (9S)-9-Ethyl-2,3-dihydro-9-hydroxy-4-methyl-3-(1,3-dioxyindoline-2-yl)-1H,12H-benzo[de]pyrano[3',4':6,7]indolizino[1,2-b]quinoline-10,13(9H,15H)-dione The compound prepared in (3) above (62 mg) and 51 mg of trione was reacted for 18 hours in the same manner as in Example 6-(3) to obtain 86 mg of the title compound.

mp: 285°–290° C. (decomposed). IR$\nu_{max}^{KBr}$ cm$^{-1}$: 3448, 2944, 1748, 1714, 1660, 1600. NMR(DMSO-d$_6$)δ: 0.89–0.93(3H, m), 1.82–1.93(2H, m), 2.32(3H, s), 2.46(1H, br), 3.18–3.22(2H, m), 5.22–5.48(4H, m), 5.85(1H, br), 6.49(1/2H, s), 6.51(1/2H, s), 7.36(1H, s), 7.65(1H, d, J=8.3 Hz), 7.79–7.84(4H, m), 8.04(1H, d, J=8.3 Hz).

MASS m/z: 547(M$^+$)

Example 37

Preparation of (9S)-3-amino-9-ethyl-2,3-dihydro-9-hydroxy-4-methyl-1H,12H-benzo[de]pyrano[3',4':6,7]indolizino[1,2-b]quinoline-10,13(9H,15H)-dione Hydrochloride

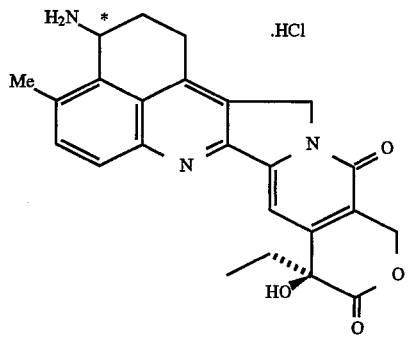

The compound prepared in Example 36-(4) (74 mg) was reacted in the same manner as in Example 7 and post-treated to produce Isomer A (14 mg) and Isomer B (15 mg) of the title compound.

Isomer A mp: above 250° C. (decomposed). IRv$_{max}^{KBr}$ cm$^{-1}$: 3448, 2936, 1742, 1656, 1592. NMR(DMSO-d$_6$)δ: 0.90(3H, t, J=7.3 Hz), 1.84–1.91(2H, m), 2.13–2.20(1H, m), 2.54–2.58 (1H, m), 2.68(3H, s), 5.05(1H, br), 5.19–5.44(4H, m), 6.50(1H, s), 7.33(1H, s), 7.76(1H, d, J=8.8 Hz), 8.10(1H, d, J=8.8 Hz), 8.27(3H, br). MASS m/z: 417 (M$^+$)

Isomer B mp: above 250° C. (decomposed). IRv$_{max}^{KBr}$ cm$^{-1}$: 3400, 3236, 2976, 1746, 1662, 1614. NMR(DMSO-d$_6$)δ: 0.89(3H, t, J=7.3 Hz), 1.83–1.94(2H, m), 2.13–2.20(1H, m), 2.59–2.62(1H, m), 2.69(3H, s), 3.27–3.42(2H, m), 5.07(1H, br), 5.19–5.44(4H, m), 7.34(1H, s), 7.78(1H, d, J=8.8 Hz), 8.12(1H, d, J=8.8 Hz), 8.53(3H, br). MASS m/z: 417(M$^+$)

Example 38

Preparation of (9S)-1-amino-4-chloro-9-ethyl-1,2-dihydro-9-hydroxy-12H-thiino[4,3,2-de]pyrano[3',4':6,7]indolizino[1,2-b]quinoline-10,13(9H,15H)-dione Hydrochloride

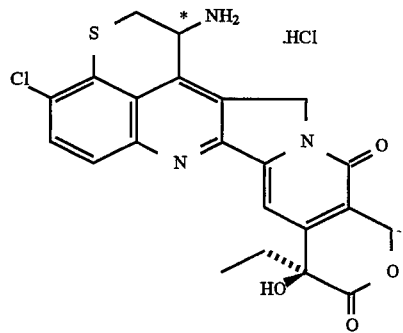

(1) 5-Acetylamino-8-chloro-4-thiochromanone

Into a solution of 500 mg of 5-acetylamino-8-amino-4-thiochromanone (described in Japanese Patent Laid-open (ko-kai) 279891/1989) suspended in a mixed solvent of 12 ml of concentrated hydrochloric acid and 3 ml of water cooled to 0° C. was slowly dropped a solution of 153 mg of sodium nitrite in 2 ml of water. The mixture was stirred for 5 minutes, whereupon a solution of copper (I) chloride in 3 ml of concentrated hydrochloric acid was added to it at 0° C. The mixture was allowed to stand at room temperature overnight and stirred for 20 minutes at 70° C. The reaction mixture was extracted with chloroform, the extract was dried over anhydrous magnesium sulfate. After concentration, the residue was subjected to silica gel column chromatography using chloroform as an eluant to obtain fractions containing the target compound. The fractions were concentrated to produce 478 mg of the title compound.

NMR(CDCl$_3$)δ: 2.22(3H, s), 2.45–3.42(4H, m), 7.43(1H, d, J=9 Hz), 8.50(1H, d, J=9 Hz)

(2) 3,5-Diacetylamino-8-chloro-4-thiochromanone

The reaction was carried out in the same manner as in Example 12-(1), except that 477 mg of the compound prepared in (1) above was used instead of 5-acetylamino-8-methyl-4-thiochromanone of Example 12-(1). The reaction product was post-treated to produce 171 mg of the title compound. NMR(CDCl$_3$)δ: 2.08(3H, s), 2.20(3H, s), 3.20 (1H, d, J=13 Hz), 3.51(1H, dd, J=13.9 Hz), 4.7–4.9(1H, m), 7.50(1H, d, J=9.2 Hz), 8.54(1H, d, J=9.2 Hz)

(3) 3-Acetylamino-5-amino-8-chloro-4-thiochromanone

The compound obtained in (2) above (171 mg) was reacted in the same manner as in Example 12-(2) and the reaction product was post-treated to produce 22 mg of the title compound.

NMR(CDCl$_3$)δ: 2.09(3H, s), 3.07(1H, d, J=13 Hz), 3.60 (1H, dd, J=12.5 Hz, 4.5 Hz), 4.7–4.9(1H, m), 6.36(1H, d, J=9 Hz), 7.00(1H, d, J=9 Hz)

(4) (9S)-1-Amino-4-chloro-9-ethyl-1,2-dihydro-9-hydroxy-12H-thiino[4,3,2-de]pyrano[3',4':6,7]indolizino[1,2-b]quinoline-10,13(9H,15H)-dione Hydrochloride The compound prepared in (3) above (22 mg) and 23 mg of trione was reacted in the same manner as in Example 12-(3) and post-treated to produce Isomer A (12 mg) and Isomer B (11 mg) of the title compound.

Isomer A

IRv$_{max}^{KBr}$ cm$^{-1}$: 3444, 1744, 1660, 1596, 1556. NMR (DMSO-d$_6$)δ: 0.90(3H, t, J=7.3 Hz), 1.89(2H, m), 3.62(2H, d, J=1.95 Hz), 5.46(2H, s), 5.47,5.85(1H, ABq, J=19.5 Hz), 6.54–6.58(1H, br.s), 7.39(1H, s), 7.97(1H, d, J=8.8 Hz), 8.06(1H, d, J=8.8 Hz), 8.80–8.87(3H, m). MASS m/z: 456(M$^+$+1)

Isomer B

IRv$_{max}^{KBr}$ cm$^{-1}$: 3452, 1746, 1662, 1596, 1556. NMR (DMSO-d$_6$)δ: 0.89(3H, t, J=7.3 Hz), 1.88(2H, m), 3.60–3.63 (2H, m), 5.46(2H, s), 5.48,5.81(2H, ABq, J=19.5 Hz), 6.54–6.57(1H, br.s), 7.40(1H, s), 7.97(1H, d, J=8.8 Hz), 8.06(1H, d, J=8.8 Hz), 8.75–8.82(3H, m). MASS m/z: 456(M$^+$+1)

Example 39

Preparation of (9S)-1-amino-9-ethyl-1,2-dihydro-9-hydroxy-12H-thiino[4,3,2-de]pyrano[3',4':6,7]indolizino[1,2-b]quinoline-10,13(9H,15H)-dione Hydrochloride

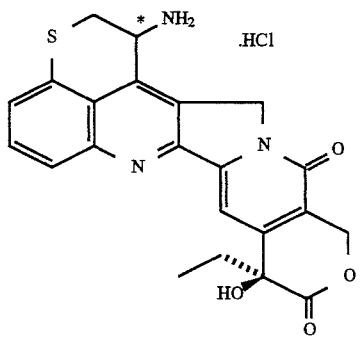

(1) 3,5-Diacetylamino-4-thiochromanone

The reaction was carried out in the same manner as in Example 12-(1), except that 360 mg of 5-acetylamino-4-thiochromanone was used instead of 5-acetylamino-8-methyl-4-thiochromanone of Example 12-(1). The reaction product was post-treated to produce 133 mg of the title compound.

NMR(CDCl$_3$)δ: 2.11(3H, s), 2.23(3H, s), 3.06(1H, d, J=12.7 Hz), 3.52(1H, dd, J=12.5 Hz, 4.8 Hz), 4.83–5.09(1H, m), 6.7–6.9(1H, br), 6.93(1H, dd, J=7.9 Hz, 1.3 Hz), 7.2–7.4 (1H, br), 7.27–7.46(1H, m), 8.46(1H, dd, J=8.4 Hz, 1.2 Hz)

(2) 3-Acetylamino-5-amino-4-thiochromanone

The compound obtained in (1) above (132 mg) was reacted in the same manner as in Example 12-(2) and the reaction product was post-treated to produce 62 mg of the title compound.

NMR(CDCl$_3$)δ: 2.09(3H, s), 3.13(1H, d, J=13 Hz), 3.52 (1H, dd, J=13 Hz, 9 Hz), 4.72–4.97(1H, m), 6.36(1H, dd, J=8.3 Hz, 1 Hz), 6.50(1H, dd, J=7.66 Hz, 1.09 Hz), 6.75–7.1 (1H, br), 7.09(1H, t, J=8 Hz)

(3) (9S)-1-Amino-9-ethyl-1,2-dihydro-9-hydroxy-12H-thiino[4,3,2-de]pyrano[3',4':6,7]indolizino[1,2-b]quinoline-10,13(9H,15H)-dione Hydrochloride The compound prepared in (2) above (62 mg) and 76 mg of trione was reacted in the same manner as in Example 12-(3) and post-treated to produce Isomer A (19 mg) and Isomer B (11 mg) of the title compound.

Isomer A

IRv$_{max}$$^{KBr}$ cm$^{-1}$: 3444, 1746, 1660, 1596, 1502. NMR (DMSO-d$_6$)δ: 0.94(3H, t, J=7.3 Hz), 1.89(2H, 3.58(2H, ABq, J=15 Hz,14 Hz), 5.43(2H, s), 5.49(1H, d, J=16.1 Hz), 5.91(1H, d, J=19.5 Hz), 6.47–6.55(1H, br.s), 7.43(1H, s), 7.69(1H, d, J=6.84 Hz), 7.78–7.82(1H, m), 8.04(1H, d, J=8.3 Hz), 8.86–8.95(3H, br). MASS m/z: 422(M$^+$+1)

Isomer B IRv$_{max}$$^{KBr}$ cm$^{-1}$: 3420, 1746, 1660, 1598, 1504. NMR(DMSO-d$_6$)δ: 0.89(3H, t, J=7.3 Hz), 1.89(2H, m), 3.51–3.63(1H, m), 5.39–5.52(4H, m), 5.91(1H, d, J=19.5 Hz), 6.49–6.60(1H, br), 7.40(1H, s), 7.71(1H, d, J=7.33 Hz), 7.79–7.83(1H, m), 8.04(1H, d, J=8.3 Hz), 8.87–9.0(3H, br). MASS m/z: 422(M$^+$+1)

Example 40

Preparation of (9S)-1-acetylamino-9-ethyl-4-chloro-1,2-dihydro-9-hydroxy-3H,12H-pyrano[3',4':6,7]indolizino[1,2-c]benzo[ij][2,7]naphthyridine-10,13 (9H,15H)-dione

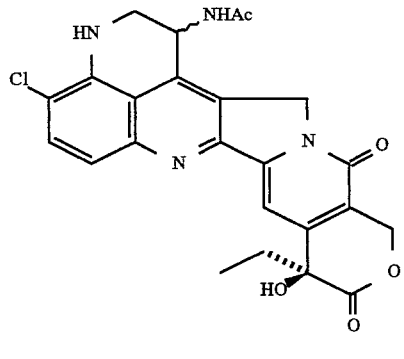

(1) 1-Acetyl-5-acetylamino-8-chloro-2,3-dihydroquinoline-4-one

The reaction was carried out in the same manner as in Example 17-(1), except that 3.8 gm of 5-amino-8-chloro-2,3-dihydroquinoline-4-one (described in Japanese Patent Laid-open (ko-kai) 279891/1989) was used instead of 5-amino-8-methyl-2,3-dihydroquinoline-4-one of Example 17-(1). The reaction product was post-treated to obtain 2.8 gm of the title compound.

mp: 175°–177° C. NMR(CDCl$_3$)δ: 2.14(s, 3H), 2.26(s, 3H), 2.0–6.2(m, 5H), 7.60(d, 1H, J=9 Hz), 8.66(d, 1H, J=9 Hz)

(2) 1-Acetyl-3,5-diacetylamino-8-chloro-2,3-dihydroquinoline-4-one

The reaction was carried out in the same manner as in Example 1-(2), except that 1.4 gm of the compound prepared in (1) above was used instead of 8-acetylamino-1-tetralone of Example 1-(2). The reaction mixture obtained by the post-treatment was further reacted in the same manner as in Example 1-(3) and post-treated to produce 0.62 gm of the title compound.

mp: 206°–210° C. IRv$_{max}$$^{KBr}$ cm$^{-1}$: 1680, 1662, 1576, 1512, 1284. NMR(CDCl$_3$)δ: 2.06(s, 3H), 2.12(s, 3H), 2.25 (s, 3H), 3.5–6.5(m, 3H), 7.5–8.7(m, 2H), 11.44(br.s, 1H). MASS m/z: 337(M$^+$), 339(M$^+$+2)

(3) 3,5-Diamino-8-chloro-2,3-dihydro-quinoline-4-one 8 ml of 6N hydrochloric acid was added to 514 mg of the compound prepared in (2) above, and the mixture was heated at 110° C. for 1.5 hours while stirring. After cooling chloroform was added to it, followed by the addition of 50 ml of 1N aqueous solution of sodium hydroxide while stirring. The chloroform layer was extracted, the extract was washed with saturated brine and dried over anhydrous sodium sulfate. The product was concentrated to produce 260 mg of the title compound.

NMR(CDCl$_3$)δ: 3.2–3.5(m, 1H), 3.6–3.8(m, 2H), 5.00 (br.s, 2H), 5.89(d, 1H, J=9 Hz), 6.37(br.s, 2H), 7.09(d, 1H, J=9 Hz)

(4) 3-Acetylamino-5-amino-8-chloro-2,3-dihydroquinoline-4-one 260 mg of the compound prepared in (3) above was dissolved into a mixed solvent of 5 ml of dichloromethane and 5 ml of THF. To this solution were added 0.16 ml of pyridine and 0.13 ml of acetic anhydride while stirring under ice cooling, and the mixture was stirred for 20 minutes. The reaction product was concentrated, and after the addition of chloroform, the residue was washed with saturated sodium bicarbonate and saturated brine, and dried over anhydrous sodium sulfate. The product was concentrated and the residue was charged into ether and petroleum ether in to produce 287 mg powder of the title compound.

IR$\nu_{max}^{KBr}$ cm$^{-1}$: 3428, 1614, 1498, 1316, 1146. NMR (CDCl$_3$)$\delta$: 2.09(s, 3H), 3.0–4.7(m, 3H), 5.10(br.s, 1H), 5.89 (d, 1H, J=9 Hz), 6.51(br.s, 1H), 7.11(d, 1H, J=9 Hz). MASS m/z: 253(M$^+$), 255(M$^+$+2)

(5) (9S)-1-Acetylamino-9-ethyl-4-chloro-1,2-dihydro-9-hydroxy-3H,12H-pyrano[3',4':6,7] indolizino[1,2-c]benzo[ij][2,7]naphthyridine-10,13 (9H,15H)-dione The compound prepared in (4) above (267 mg) and 277 mg of trione werte reacted for 7 hours in the same manner as in Example 17-(5) and post-treated to obtain 202 mg of the title compound.

mp: 250°–270° C. IR$\nu_{max}^{KBr}$ cm$^{-1}$: 1748, 1662, 1608, 1158. NMR(DMSO-d$_6$)$\delta$: 0.87(t, 3H, J=7 Hz), 1.7–2.0(m, 2H), 2.50(s, 3H), 3.4–3.6(m, 2H), 5.19,5.27(ABq, 2H, J=19 Hz), 5.43(s, 2H), 5.4–5.6(m, 1H), 6.52(s, 1H), 7.29,7.30 (each s, 1H), 7.40(d, 1H, J=9 Hz), 7.71(d, 1H, J=9 Hz), 8.52(t, 1H, J=8 Hz). MASS m/z: 480(M$^+$), 482(M$^+$+2)

Example 41

Preparation of (9S)-1-amino-9-ethyl-4-chloro-1,2-dihydro-9-hydroxy-3H,12H-pyrano[3',4':6,7] indolizino[1,2-c]benzo[ij][2,7]naphthyridine-10,13 (9H,15H)-dione Hydrochloride

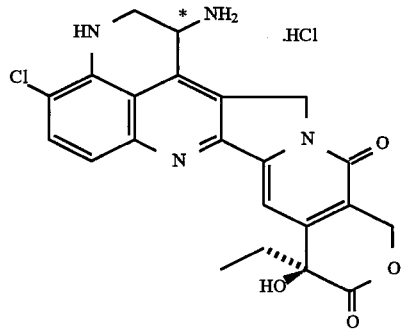

The compound prepared in Example 40-(5) (190 mg) was reacted for 3 hours in the same manner as in Example 2 and post-treated to produce Isomer A (67 mg) and Isomer B (40 mg) of the title compound.

Isomer A mp: 130°–150° C. IR$\nu_{max}^{KBr}$ cm$^{-1}$: 1744, 1658, 1606, 1162. NMR(DMSO-d$_6$)$\delta$: 0.88(t, 3H, J=7 Hz), 1.7–2.0(m, 2H), 3.45(q, 1H, J=7 Hz), 3.57,3.89(each d, 1H, J=12 Hz), 4.2–4.5(br, 1H), 5.15(s, 1H), 5.39,5.79(ABq, 2H, J=19 Hz), 5.45(s, 2H), 6.55(s, 1H), 6.85(s, 1H), 7.34(s, 1H), 7.49(d, 1H, J=9 Hz), 7.78(d, 1H, J=9 Hz), 8.68(br.s, 3H). MASS m/z: 438(M$^+$), 440(M$^+$+2)

Isomer B mp: 250°–270° C. IR$\nu_{max}^{KBr}$ cm$^{-1}$: 1750, 1600, 1608, 1160. NMR(DMSO-d$_6$)$\delta$: 0.88(t, 3H, J=7 Hz), 1.7–1.9(m, 2H), 3.56,3.89(ABq, 1H, J=12 Hz), 5.16(s, 1H), 5.41,5.78 (ABq, 2H, J=19 Hz), 5.45(s, 2H), 6.56(s, 1H), 6.86(s, 1H), 7.34(s, 1H), 7.49(d, 1H, J=9 Hz), 7.79(d, 1H, J=9 Hz), 8.67(br.s, 3H). MASS m/z: 438(M$^+$), 440(M$^+$+2)

Example 42

Preparation of (9S)-3-amino-9-ethyl-2,3-dihydro-9-hydroxy-1H,12H-benzo[de]pyrano[3',4':6,7] indolizino[1,2-b]quinoline-10,13(9H,15H)-dione Hydrochloride

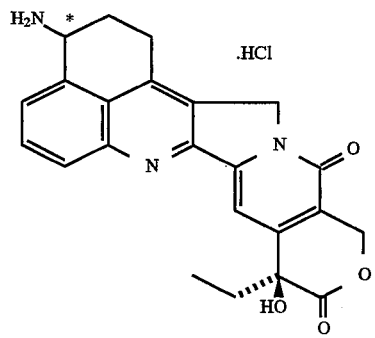

(1) 8-Acetylamino-4-(1,3-dioxoisoindoline-2-yl)-1-tetralone 1.07 gm of 8-acetylamino-1-tetralone, 1.28 gm of N-bromosuccinimide, and a catalytic amount of benzoyl peroxide were added to 60 ml of carbon tetrachloride. The mixture was heated under reflux for 1 hour, and cooled to room temperature. The precipitate was removed by filtration and the solvent was evaporated. The residue was subjected to silica gel column chromatography using chloroform as an eluant to obtain fractions containing bromine isomer of the target compound. The bromine isomer was dissolved in 20 ml of DMF and cooled to 0° C., followed by the addition 440 ml of sodium azide, a bit at a time. After stirring for 30 minutes at 0° C. and for 1 hour at room temperature, and an addition of 30 ml of water, the mixture was extracted twice with ether. The extract was washed with water and saturated brine in this order, and dried over anhydrous sodium sulfate. The solvent was evaporated and the residue was subjected to silica gel column chromatography using hexane-ethyl acetate (4:1) as an eluant to obtain fractions containing the target compound. The fractions were concentrated to obtain 1.17 mg of 4-azide isomer. To the azide isomer were added 50 ml of benzene, 1.38 gm of triphenylphosphine, and 781 mg of phthalic anhydride. The mixture was heated under reflux for 12 hours, and a further 4 hours after the addition of 40 mg of tetra-n-butylammonium cyanide. After evaporating the solvent, the residue was subjected to silica gel column chromatography using hexane-ethyl acetate (2:1) as an eluant to obtain fractions containing the target compound. The fractions were concentrated to produce 1.25 mg of the title compound.

NMR(CDCl$_3$)$\delta$: 2.26(3H, s), 2.2–2.3(1H, m), 2.75–3.0 (3H, m), 5.69(1H, dd, J=5.4 Hz, 10.8 Hz), 6.74(1H, d, J=7.8 Hz), 7.44(1H, t, J=7.8 Hz), 7.75–7.80(2H, m), 7.85–7.82 (2H, m), 8.71(1H, d, J=7.8 Hz), 12.18(1H, s), (2) 8-Amino-4-(1,3-dioxoisoindoline-2-yl)-1-tetralone The compound prepared in (1) above (339 mg) was added to 10 ml of 1N hydrochloric acid and heated under reflux for 1 hour. The mixture was cooled to room temperature, alkalinized with the addition of sodium bicarbonate, and extracted with chloroform. The extract was washed with water and saturated brine in this order, and dried over anhydrous sodium sulfate. The solvent was evaporated and the residue was subjected to silica gel column chromatography using hexane-ethyl acetate (4:1) as an eluant to obtain fractions containing the target compound. The fractions were concentrated to produce 190 mg of the title compound.

NMR(CDCl$_3$)δ: 2.15–2.21(1H, m), 2.7–3.0(3H, m), 5.60 (1H, dd, J=4.6 Hz,11.5 Hz), 6.22(1H, d, J=7.8 Hz), 6.55(1H, d, J=7.8 Hz), 7.12(1H, t, J=7.8 Hz), 7.74–7.79(2H, m), 7.86–7.90(2H, m)

(3) (9S)-3-Amino-9-ethyl-2,3-dihydro-9-hydroxy-1H,12 H-benzo[de]pyrano[3',4':6,7]indolizino[1,2-b]quinoline-10,13(9H,15H)-dione Hydrochloride 20 ml of toluene, 190 mg of the compound prepared in (2) above, and 163 mg of trione were reacted for 15 hours in the same manner as in Example 1-(5) and post-treated to obtain 263 mg of (9S)-9-ethyl2,3-dihydro-9-hydroxy-3-(1,3-dioxoisoindoline-2-yl)-1H,12H-benzo[de]pyrano[3',4':6,7]indolizino[1,2-b]quinoline-10,13(9H,15H)-dione as a mixture of 3-position isomer. 223 mg of this compound was processed in the same manner as in Example 13-(12) to obtain 73 mg of Isomer A and 58 mg of Isomer B of the title compound.

Isomer A mp: above 190° C. (decomposed). NMR(DMSO-d$_6$)δ: 0.90(3H, t, J=7.3 Hz), 1.87(2H, m), 2.2–2.5(2H, m), 3.2–3.45(2H, m), 4.98(1H, m), 5.30(2H, s), 5.44(2H, s), 7.36(1H, s), 7.85–7.93(2H, m), 8.17(1H, d, J=8.3 Hz), 8.88(3H, m)

Isomer B mp: above 218° C. (decomposed). NMR(DMSO-d$_6$)δ: 0.90(3H, t, J=7.3 Hz), 1.88(2H, m), 2.3–2.5(2H, m), 3.3–3.4 (2H, m), 4.91(1H, m), 5.32(2H, s), 5.45(2H, s), 7.37(1H, s), 7.85(1H, d, J=6.8 Hz), 7.92(1H, dd, J=6.8 Hz, 7.7 Hz), 8.19(1H, d, J=7.7 Hz), 8.80(3H, m)

Example 43

Preparation of (9S)-1-amino-9-ethyl-1,2-dihydro-9-hydroxy-4-methyl-12H-pyrano[4,3,2-de]pyrano[3',4':6,7]indolizino[1,2-b]quinoline-10,13(9H,15H)-dione Hydrochloride

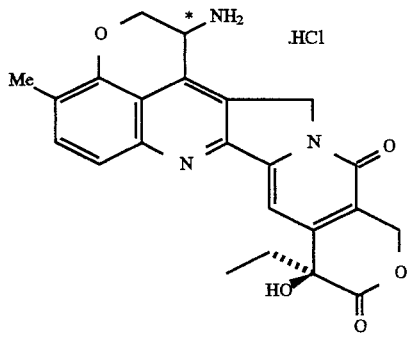

(1) 3,5-Diacetylamino-8-methyl-4-chromanone

The reaction was carried out in the same manner as in Example 12-(1), except that 1 gm of 5-acetylamino-8-methyl-4-chromanone was used instead of 5-acetylamino-8-methyl-4-thiochromanone of Example 12-(1). The reaction product was post-treated to produce 105 mg of the title compound.

NMR(CDCl$_3$)δ: 2.11(3H, s), 2.17(3H, s), 2.22(3H, s), 3.98(1H, dd, J=12.1 Hz, 15.1 Hz), 4.70–5.05(2H, m), 6.26 (1H, m), 7.34(1H, d, J=8.3 Hz), 8.18(1H, d, J=8.3 Hz)

(2) 3-Acetylamino-5-amino-8-methyl-4-chromanone

The compound prepared in (1) above (100 mg) was added to 3 ml of concentrated hydrochloric acid and heated at 80° C. with stirring for 1 hour. The mixture was cooled, alkalinized with the addition of sodium bicarbonate, and extracted with chloroform. The chloroform layer was dried over anhydrous sodium sulfate. The solvent was evaporated and the residue was subjected to silica gel column chromatography using chloroform-ethyl acetate (4:1) as an eluant to obtain fractions containing the target compound. The fractions were concentrated to produce 48 mg of the title compound.

mp: 178°–180° C. IRv$_{max}^{KBr}$ cm$^{-1}$: 3448, 3328, 1650, 1628, 1484. NMR(CDCl$_3$)δ: 2.06(3H, s), 2.08(3H, s), 3.7–4.1(1H, m), 4.65–5.05(2H, m), 6.14(1H, d, J=8.3 Hz), 7.06(1H, d, J=8.3 Hz)

(3) (9S)-1-Amino-9-ethyl-1,2-dihydro-9-hydroxy-4-methyl-12H-pyrano[4,3,2-de]pyrano[3',4':6,7]indolizino[1,2-b]quinoline-10,13(9H,15H)-dione Hydrochloride The compound prepared in (2) above (139 mg) and 156 mg of trione was added to 12 ml of acetic acid and heated under reflux for 6 hours. The reaction mixture was cooled, solvent was evaporated, and the residue was subjected to silica gel column chromatography using chloroform-methanol (98:2) as an eluant to obtain fractions containing the target compound. The fractions were concentrated and the residue, after the addition of 5 ml of concentrated hydrochloric acid, was stirred for 2 hours. The reaction mixture was concentrated and 20 ml of water was added to the residue to remove insoluble substances. The filtrate was purified with HPLC (CAPCELL PAK C18) using a mixture of acetonitrile-water-1N hydrochloric acid (18:82:1) to obtain 77 mg of Isomer A and 93 mg of Isomer B of the title compound.

Isomer A mp: above 200° C. (decomposed). IRv$_{max}^{KBr}$ cm$^{-1}$: 3432, 1756, 1658, 1602. NMR(DMSO-d$_6$)δ: 0.89(3H, t, J=6.8 Hz), 1.83–1.92(2H, m), 2.44(3H, s), 4.44(1H, d, J=12.2 Hz), 4.91(1H, d, J=12.2 Hz), 5.20(1H, brs), 5.39,5.78(2H, ABq, J=19 Hz), 5.44(2H, s), 7.37(1H, s), 7.78(1H, d, J=8.8 Hz), 7.80(1H, d, J=8.8 Hz), 8.88(3H, br). MASS m/z: 420(M$^{++1}$)

Isomer B mp: above 200° C. (decomposed). IRv$_{max}^{KBr}$ cm$^{-1}$: 3444, 1746, 1658, 1596. NMR(DMSO-d$_6$)δ: 0.90(3H, t, J=7.3 Hz), 1.83–1.92(2H, m), 2.45(3H, s), 4.44(1H, d, J=11.7 Hz), 4.91(1H, d, J=11.7 Hz), 5.20(1H, brs), 5.41,5.78(2H, ABq, J=19.5 Hz), 5.44(2H, s), 5.44,5.48(2H, ABq, J=16.6 Hz), 7.40(1H, s), 7.78(1H, d, J=8.8 Hz), 7.82(1H, d, J=8.8 Hz), 8.97(3H, br). MASS m/z: 420(M$^{++1}$)

Example 44

Preparation of (9S)-3-amino-9-ethyl-5-fluoro-2,3-dihydro-9-hydroxy-1H,12H-benzo[de]pyrano[3',4':6,7]indolizino[1,2-b]quinoline-10,13(9H,15H)-dione

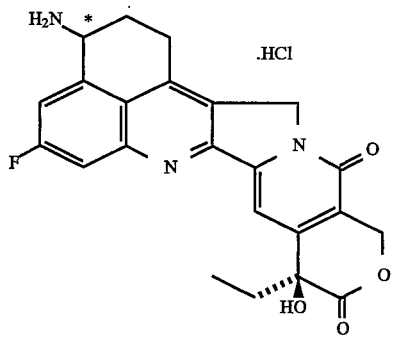

(1) 4-(4-Fluorophenyl)-4-oxobutanoic Acid 50 gm of succinic anhydride and 133.3 gm of aluminum chloride was added to 79.6 gm of fluorobenzene, and the mixture was heated under reflux for 6 hours. After evaporating the surplus fluorobenzene, the residue was added to 2 l of 1% hydrochloric acid aqueous solution. The precipitate was collected by filtration, washed with water, and dried to obtain 73 gm of the title compound.

NMR(CDCl$_3$)δ: 2.82(2H, t, J=6.6 Hz), 3.29(2H, t, J=6.6 Hz), 7.1–7.2(2H, m), 7.9–8.1(2H, m)

(2) Methyl 4-(4-fluorophenyl)butanoate

The compound obtained in (1) above 73 gm was dissolved into 600 ml of acetic acid. To the solution were added 20 ml of 40% perchloric acid and 10% palladium-on-carbon to effect catalytic hydrogenation under 5 atm. After the evaporation of acetic acid and the addition of 100 ml of water, the residue was extracted with ethyl acetate. The extract was washed with saturated sodium bicarbonate and saturated brine in this order, and dried over anhydrous sodium sulfate. The solvent was evaporated and 100 ml of dichloromethane, 74 gm of sodium carbonate, and 30 ml of thionyl chloride were added to the residue. The mixture was heated under reflux for 3 hours and then cooled to 0° C., and 150 ml of methanol was slowly added, followed by stirring for 12 hours at room temperature. After the addition of 300 ml of ethyl acetate, the resulting product was washed with water and saturated brine in this order, and dried over anhydrous sodium sulfate. The solvent was evaporated to obtain 66.7 gm of the title compound.

NMR(CDCl$_3$)δ: 1.93(2H, quintet, J=7.8 Hz), 2.32(2H, t, J=7.8 Hz), 2.62(2H, t, J=7.8 Hz), 3.66(3H, s), 6.96(2H, m), 7.13(2H, m)

(3) Methyl 4-(4-fluoro-2-nitrophenyl)butanoate

The compound obtained in (2) above (66.7 gm) was added to 600 ml of cold concentrated sulfuric acid, and to the mixture was dropwise added a solution of 50 gm of potassium sulfate in 300 ml concentrated sulfuric acid while maintaining the internal temperature below 5° C. After the addition, the mixture was stirred for a further 30 minutes. The reaction product was poured into ice-coled water and extracted with ethyl acetate. The ethyl acetate layer was washed with water, saturated sodium bicarbonate, and saturated brine in this order, and dried over anhydrous sodium sulfate. The solvent was evaporated, and the residue was subjected to silica gel column chromatography using hexane-ethyl acetate (40:3) as an eluant to obtain fractions containing the target compound. The fractions were concentrated to obtain 39.3 gm of the title compound.

NMR(CDCl$_3$)δ: 1.98(2H, m), 2.40(2H, t, 7.3 Hz), 2.91(2H, t, J=7.8 Hz), 3.69(3H, s), 7.27(1H, ddd, J=2.9 Hz, 7.8 Hz, 8.3 Hz), 7.37(1H, dd, J=5.3 Hz,8.3 Hz), 7.66(1H, dd, J=2.9 Hz,8.8 Hz)

(4) Methyl 4-(2-acetylamino-4-fluorophenyl)butanoate

The compound obtained in (3) above (39.3 gm) and 3 gm of 10% palladium-on-carbon were added to 200 ml of methanol, and the mixture was catalytically hydrogenated for 6 hours. The catalyst was removed by filtration and the solvent was evaporated. To the reside were added 50 ml of chloroform and, while stirring at room temperature, 50 ml of acetic anhydride. After further stirring for 3 hours, the reaction mixture was concentrated to dryness to obtain 42.0 gm of the title compound.

NMR(CDCl$_3$)δ: 1.72–1.85(2H, m), 2.31(3H, s), 2.45(2H, m), 2.56(2H, m), 3.76(3H, s), 6.71(1H, dt, J=2.5 Hz,8.3 Hz), 7.04(1H, dd, J=6.3 Hz,8.3 Hz), 8.08(1H, dd, J=2.5 Hz,10.8 Hz)

(5) 5-Acetylamino-7-fluoro-1-tetralone

The compound obtained in (4) above (42 gm) was dissolved into 100 ml of methanol. After the addition of 200 ml of 1N hydrochloric acid, the mixture was stirred for 3 hours at room temperature. The reaction mixture was concentrated to 200 ml and, after acidifying with the addition of concentrated hydrochloric acid, extracted three times with ethyl acetate. The ethyl acetate layer was washed with water and saturated brine in this order, and dried over anhydrous sodium sulfate. The solvent was evaporated, and to the residue were added 100 ml of dichloromethane, then 17 gm of sodium carbonate and 12 ml of thionyl chloride. The mixture was heated under reflux for 2 hours, and then cooled to room temperature to remove insoluble substances by filtration. The filtrate was concentrated and 200 ml of 1,2-dichloromethane and 40 gm of aluminum chloride were added to the residue. The mixture was stirred for 3 hours at 70° C. then for 1 hour at 90° C. The reaction product was poured into ice-coled water and extracted with chloroform. The extract was washed with water, saturated sodium bicarbonate, and saturated brine in this order, and dried over anhydrous sodium sulfate. The solvent was evaporated, and the residue was subjected to silica gel column chromatography using chloroform-ethyl acetate (7:3) as an eluant to obtain fractions containing the target compound. The fractions were concentrated to obtain 17 gm of the title compound.

NMR(CDCl$_3$)δ: 2.16(2H, m), 2.24(3H, s), 2.66(2H, t, J=6.83 Hz), 2.78(2H, t, J=6.0 Hz), 7.08(1H, br.s), 7.59(1H, dd, J=2.4 Hz, 8.3 Hz), 7.84(1H, dd, J=2.4 Hz, 7.8 Hz) (6)

(6) 5-Acetylamino-7-fluoro-1,2,3,4-tetrahydronaphthalene

The compound obtained in (5) above (10.5 gm), 5 gm of 10% palladium-on-carbon, and 5 ml of perchloric acid were added to 300 ml of acetic acid, and the mixture was catalytically hydrogenated at 5 atm. for 6 hours. The catalyst was removed by filtration and the filtrate was concentrated to 50 ml. Upon addition of 100 ml of water, the concentrate was extracted 3 times with chloroform. The chloroform layer was washed with water and saturated brine in this order, and dried over anhydrous sodium sulfate. The solvent was evaporated to obtain 9.5 gm of the title compound.

NMR(CDCl$_3$)δ: 1.7–1.9(4H, m), 2.20(3H, s), 2.52(2H, m), 2.75(2H, m), 6.61(1H, d, J=8.8 Hz), 6.94(1H, m), 7.59(1H, d, J=9.8 Hz)

(7) 8-Acetylamino-6-fluoro-1-tetralone

To a solution of the compound obtained in (6) above (9.46 gm) in 420 ml of acetone was added 42 ml of 15% aqueous solution of magnesium sulfate. After cooling to 0° C., 21.7 gm of potassium permanganate was added to the mixture, a bit at a time. The mixture was stirred for 50 minutes at 0° C. and for 1 hour at room temperature. Upon addition of 1 l of water, the reaction product was extracted 3 times with chloroform. The chloroform layer was washed with water and saturated brine in this order, and dried over anhydrous sodium sulfate. The solvent was evaporated and the residue was subjected to silica gel column chromatography using hexane-ethyl acetate (3:1) as an eluant to obtain fractions containing the target compound. The fractions were concentrated to obtain 7.98 gm of the title compound.

NMR(CDCl$_3$)δ: 2.08(2H, m), 2.24(3H, s), 2.69(2H, t, J=6.4 Hz), 2.96(2H, t, J=6.1 Hz), 6.64(1H, dd, J=2.4 Hz,8.3 Hz), 8.42(1H, dd, J=2.4 Hz,12.0 Hz), 12.35(1H, br.s)

(8) 6-Fluoro-4-triphenylmethylamino-1-tetralone 10 ml of 4N hydrochloric acid was added to 287 mg of the compound obtained in (7) above, and the mixture was heated under reflux for 1 hour. The reaction mixture was poured into ice-cooled water extracted with ethyl acetate. The ethyl acetate layer was washed with water, saturated aqueous solution of sodium bicarbonate, and saturated brine in this order, and dried over anhydrous sodium sulfate. The solvent was evaporated and the residue was subjected to silica gel column chromatography using hexane-ethyl acetate (7:3) as an eluant to obtain fractions containing the target compound. 5 ml of dichloromethane, 0.8 ml of triethylamine, and 1.5 gm of triphenylmethyl chloride were added to the residue, and the mixture was heated under reflux for 4 hour, then cooled to room temperature. Upon addition of 20 ml of dichloromethane, the reaction mixture was washed with water, saturated aqueous solution of sodium bicarbonate, and saturated brine in this order, and dried over anhydrous sodium sulfate. The solvent was evaporated and the residue was subjected to silica gel column chromatography using hexane-ethyl acetate (3:1) as an eluant to obtain fractions containing the target compound. The fractions were concentrated to obtain 706 mg of the title compound.

NMR(CDCl$_3$)δ: 2.03(2H, m), 2.66(2H, t, J=6.4 Hz), 2.84 (2H, t, J=6.1 Hz), 5.67(1H, dd, J=2.4 Hz,12.7 Hz), 6.02(1H, dd, J=2.4 Hz,8.8 Hz), 7.2–7.4(15H, m), 11.29(1H, s)

(9) 6-Fluoro-8-triphenylmethylamino-4-(1,3-dioxoisoindolin-2-yl)-1-tetralone 706 mg of the compound obtained in (8) above, 231 mg of N-bromosuccinimide, and a catalytic amount of benzoyl peroxide were added to 30 ml of carbon tetrachloride. The mixture was heated under reflux for 30 minutes, and cooled to room temperature. After the addition of 30 ml of chloroform, the reaction product was washed with 1N sodium hydroxide, water, and saturated brine in this order, and dried over anhydrous sodium sulfate. The solvent was evaporated and the residue was dissolved into 5 ml of DMF and cooled to 0° C. 160 mg of sodium azide was added to the solution, a bit at a time, followed by stirring for 1 hour at room temperature. After the addition of 30 ml of water, the reaction mixture was extracted with ether and washed with water and saturated brine in this order, and dried over anhydrous sodium sulfate. The solvent was evaporated and the residue was subjected to silica gel column chromatography using hexane-ethyl acetate (9:1) as an eluant to obtain fractions containing the target compound. The fractions were concentrated to obtain 344 mg of 4-azide isomer. To the azide isomer were added 20 ml of benzene, 205 mg of triphenylphosphine, and 116 mg of phthalic anhydride. The mixture was heated under reflux for 12 hours, after the addition of 40 mg of tetra-n-butylammonium cyanide for a further 8 hours. After heating under reflux for a further 8 hours, the solvent was evaporated, and the residue was subjected to silica gel column chromatography using chloroform-hexane (1:1) as an eluant to obtain fractions containing the target compound. The fractions were concentrated to produce 440 mg of the title compound.

NMR(CDCl$_3$)δ: 2.15(1H, m), 2.7–3.1(3H, m), 5.55(1H, dd, J=4.40 Hz, 12.2 Hz), 5.75(1H, dd, J=2.4 Hz,7.8 Hz), 5.77(1H, dd, J=2.4 Hz,10.2 Hz), 7.2–7.4(15H, m), 7.67(2H, m), 7.88(2H, m), 11.41(1H, s)

(10) 8-Amino-6-fluoro-(1,3-dioxoisoindolin-2-yl)-1-tetralone

The compound obtained in (1) above (423 mg) was added to 8 ml of formic acid which were cooled to 0° C., and while stirring, one drop of concentrated hydrochloric acid was added to the mixture. After stirring for 1 hour at room temperature the solvent was evaporated. The residue was dissolved into chloroform and concentrated. A mixed solvent of ether and hexane was added to the concentrate to obtain crystals, which were collected by filtration to obtain 132 mg of the title compound.

NMR(CDCl$_3$)δ: 2.16(1H, m), 2.7–3.05(3H, m), 5.56(1H, dd, J=4.4 Hz,11.7 Hz), 5.95(1H, dm, J=9.8 Hz), 6.21(1H, dd, J=2.0 Hz, 10.8 Hz), 7.78(2H, m), 7.90(2H, m)

(11) (9S)-3-Amino-9-ethyl-5-fluoro-2,3-dihydro-9-hydroxy-1H,12H-benzo[de]pyrano[3',4':6,7] indolizino[1,2-b]quinoline-10,13(9H,15H)-dione Hydrochloride 10 ml of toluene, 125 mg of the compound obtained in (10) above, and 104 mg of trione were reacted for 22 hours in the same manner as in Example 1-(5) and post-treated to obtain 119 mg of (9S)-9-ethyl-5-fluoro-2,3-dihydro-9-hydroxy-3-(1,3-dioxoisoindolin-2-yl)-1H,12H-benzo [de] pyrano[3',4':6,7]indolizino[1,2-b]quinoline-10,13(9H, 15H) -dione as a mixture of 3-position isomers. 119 mg of this compound was treated in the same manner as in Example 13-(12) to obtain 31 mg of Isomer A and 35 mg of Isomer B of the title compound.

Isomer A mp: gradually colored from 206° C. (decomposed). NMR (DMSO-d$_6$)δ: 0.88(3H, t, J=7.3 Hz), 1.87(2H, m), 2.21–2.33 (1H, m), 2.40–2.55(1H, m), 3.25–3.40(2H, m), 4.92(1H, m), 5.31(2H, s), 5.45(2H, s), 6.54(1H, s), 7.35(1H, s), 7.81(1H, dd, J=2.4 Hz, 9.3 Hz), 7.97(1H, dd, J=2.4 Hz, 10.3 Hz), 8.70(3H, br.s)

Isomer B mp: gradually colored from 194° C. (decomposed). NMR (DMSO-d$_6$)δ: 0.88(3H, t, J=7.3 Hz), 1.88(2H, m), 2.2–2.3 (1H, m), 2.4–2.5(1H, m), 3.3–3.4(2H, m), 4.94(1H, m), 5.31(2H, s), 5.45(2H, s), 7.36(1H, s), 7.82(1H, dd, J=2.4 Hz, 9.3 Hz), 7.98(1H, dd, J=2.4 Hz, 10.2 Hz), 8.81(3H, br.s)

Example 45

Preparation of (9S)-9-ethyl-5-fluoro-2,3-dihydro-9-hydroxy-3-dimethylamino-1H,12H-benzo[de]pyrano[3',4':6,7]indolizino[1,2-b]quinoline-10,13(9H,15H)-dione Hydrochloride

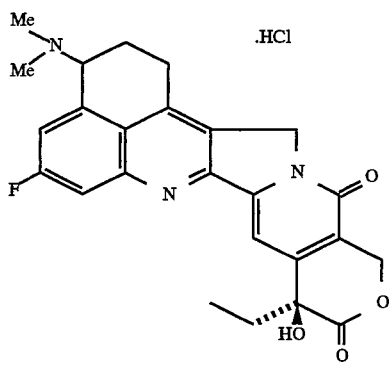

To 15 mg of Isomer A prepared in Example 44 were added 1 ml of 35% aqueous solution of formaline, 0.08 ml of formic acid and 0.03 ml of 1N sodium hydroxide aqueous solution, and the mixture was heated under reflux for 1 hour. After evaporating the solvent, 2 ml of 1N hydrochloric acid aqueous solution was added to the residue. The solvent was evaporated and 4 ml of water was added to remove insoluble substances by filtration. The filtrate was purified with HPLC (CAPCELL PAK C18) using a mixture of acetonitrile-water-1N hydrochloric acid (17:83:1) to obtain 9 mg of the title compound.

mp: above 182° C. (decomposed). NMR(DMSO-$d_6$)δ: 0.88(3H, t, J=7.3 Hz), 1.87(2H, m), 2.3–2.7(2H, m), 2.85 (3H, d, J=4.4 Hz), 2.87(3H, d, J=4.4 Hz), 3.2–3.6(2H, m), 4.99(1H, m), 5.25,5.36(2H, ABq, J=19 Hz), 5.45(2H, s), 6.55(1H, m), 7.36(1H, s), 8.0–8.1(2H, m), 10.42(1H, m)

Example 46

Preparation of (9S)-9-ethyl-5-fluoro-2,3-dihydro-9-hydroxy-3-dimethylamino-1H,12H-benzo[de]pyrano[3',4':6,7]indolizino[1,2-b]quinoline-10,13(9H,15H)-dione Hydrochloride

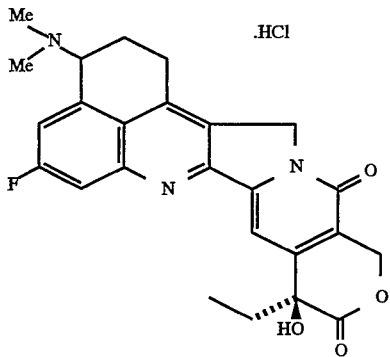

Isomer B prepared in Example 44 (20 mg) was treated in the same manner as in Example 45 and purified with HPLC (CAPCELL PAK C18) using a mixture of acetonitrile-water-1N hydrochloric acid (21:79:1) to obtain 9 mg of the title compound.

mp: above 230° C. (decomposed). NMR(DMSO-$d_6$)δ: 0.88(3H, t, J=7.3 Hz), 1.88(2H, m), 2.3–2.7(2H, m), 2.86 (3H, d, J=4.4 Hz), 2.89(3H, d, J=4.9 Hz), 3.3–3.5(2H, m), 4.99(1H, m), 5.26,5.37(2H, ABq, J=19 Hz), 5.45(2H, s), 6.55(1H, m), 7.36(1H, s), 8.01(1H, dm, J=9.3 Hz), 8.05(1H, dm, J=9.8 Hz), 10.25(1H, m)

Example 47

Preparation of (9S)-9-ethyl-5-fluoro-2,3-dihydro-9-hydroxy-3-methylamino-1H,12H-benzo[de]pyrano[3',4':6,7]indolizino[1,2-b]quinoline-10,13(9H,15H)-dione Hydrochloride

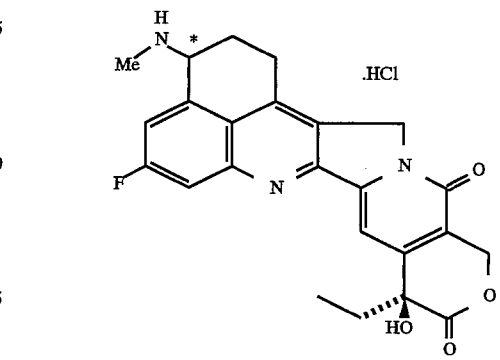

(1) 5-Acetoamino-7-fluoro-1-methyltrifluoroacetylaminotetralone

The compound obtained in Example 44-(5) (1.02 gm), 11 ml of 40% aqueous solution of methylamine, and 1.2 gm of 10% palladium-on-carbon were added to 20 ml of ethanol and catalytically hydrogenated for 9.5 hours. The catalyst was removed by filtration and the filtrate was concentrated to dryness. The residue was dissolved into 20 ml of chloroform. 2 ml of triethylamine was added to the solution. Then, 4 ml of trifluoroacetic anhydride was added at 0° C. while stirring. After stirring for a further 1 hour at room temperature, the resulting reaction mixture was washed with dilute hydrochloric acid, water, and saturated brine in this order, and dried over anhydrous sodium sulfate. The solvent was evaporated and the residue was subjected to silica gel column chromatography using chloroform-ethyl acetate (40:3) as an eluant to obtain fractions containing the target compound. The fractions were concentrated to obtain 1.33 gm of the title compound.

NMR(CDCl$_3$)δ: 1.7–2.0(1.6H, m), 2.0–2.3(2.4H, m), 2.22(3H, s), 2.5–2.7(2H, m), 2.71,2.84(3H, each s), 5.15 (0.4H, m), 5.79(0.6H, m), 6.54(0.6H, d, J=8.3 Hz), 6.65 (0.4H, d, J=8.3 Hz), 6.97(1H, m), 7.65–7.75(1H, m)

(2) 8-Acetoamino-6-fluoro-4-methyltrifluoroacetylamino-1-tetralone

To a solution of the compound obtained in (1) above (1.32 gm) in 60 ml of acetone was added 6 ml of 15% aqueous solution of magnesium sulfate. 1.9 gm of potassium permanganate was slowly added to the mixture at 0° C. while stirring. After the addition, the mixture was stirred for 30 minutes at the same temperature and another 30 minutes at room temperature. Upon addition of 60 ml of water, the reaction product was extracted 3 times with chloroform. The chloroform layer was washed with water and saturated brine in this order, and dried over anhydrous sodium sulfate. The solvent was evaporated and the residue was subjected to silica gel column chromatography using chloroform-ethyl acetate (9:1) as an eluant to obtain fractions containing the target compound. The fractions were concentrated to obtain 748 mg of the title compound.

NMR(CDCl₃)δ: 2.0–2.4(2H, m), 2.26(3H, s), 2.7–3.0(2H, m), 2.84,2.97(3H, each small m), 5.30(0.3H, dd, J=4.9 Hz,11.7 Hz), 5.96(0.7H, dd, J=4.4 Hz,11.7 Hz), 6.43(0.7H, dm, J=7.3 Hz), 6.56(0.3H, dm, J=7.3 Hz), 8.57(0.7H, dd, J=2.4 Hz,11.2 Hz), 8.60(0.3H, dd, J=2.9 Hz,11.7 Hz), 12.3 (1H, br.s)

(3) 8-Amino-6-fluoro-4-methyltrifluoroacetylamino-1-tetralone 20 ml of 4N hydrochloric acid was added to 722 mg of the compound obtained in (2) above, and the mixture was heated under reflux for 5 hours. After cooling to room temperature, the mixture was weakly alkalinized by the addition of saturated sodium carbonate and extracted three times with chloroform. The extract was washed with saturated brine, and dried over anhydrous sodium sulfate. The solvent was evaporated, and to the residue were added 50 ml of dichloromethane and 0.29 ml of triethylamine. Then, 15 ml of a dichloromethane solution containing 0.29 ml of trifluoroacetic anhydride was added dropwise to the mixture while stirring and cooling in an ice-salt bath. After stirring for 1 hour at the same temperature, the mixture was washed with water, saturated aqueous solution of citric acid, water, and saturated brine in this order, and dried over anhydrous sodium sulfate. The solvent was evaporated and the residue was subjected to silica gel column chromatography using chloroform-ethyl acetate (19:1) as an eluant to obtain fractions containing the target compound. The fractions were concentrated to obtain 421 mg of the title compound.

NMR(CDCl₃)δ: 2.0–2.4(2H, m), 2.6–2.9(2H, m), 2.86, 2.98(3H, each s), 5.20(0.35H, dd, J=4.4 Hz,11.7 Hz), 5.87 (0.65H, dd, J=4.4 Hz,11.7 Hz), 5.97(0.65H, dm, J=9.3 Hz), 6.09(0.35H, dm, J=9.3 Hz), 6.26(0.65H, dd, J=2.4 Hz, 8.7 Hz), 6.28(0.35H, dd, J=2.0 Hz, 8.8 Hz)

(4) (9S)-9-Ethyl-5-fluoro-2,3-dihydro-9-hydroxy-3-methylamino-1H,12H-benzo[de]pyrano[3',4':6,7] indolizino [1,2-b]quinoline-10,13(9H,15H)-dione Hydrochloride To 24 ml of toluene were added 378 mg of the compound obtained in (3) above and 330 mg of trione, and the mixture was reacted in the same manner as in Example 1-(5) and post-treated to obtain 340 mg of (9S)-9-ethyl-5-fluoro-2,3-dihydro-9-hydroxy-3-methyltrifluoroacetylamino-1H,12H-benzo[de]pyrano[3',4':6,7]indolizino[1,2-b]quinoline-10,13 (9H,15H)-dione as a mixture of 3-position isomers. 30 ml of concentrated hydrochloric acid was added to 300 mg of this compound, and the mixture was heated at 80° C. for 2.5 hours while stirring. The solvent was evaporated, 15 ml of water was added to the residue to remove insoluble substances by filtration. The filtrate was purified with HPLC (CAPCELL PAK C18) using a mixture of acetonitrile-water-1N hydrochloric acid (20:80:1) to obtain 83 mg of Isomer A and 103 mg of Isomer B of the title compound.

Isomer A mp: above 230° C. (decomposed). NMR(DMSO-d₆)δ: 0.89(3H, t, J=7.3 Hz), 1.87(2H, m), 2.3–2.6(2H, m), 2.70 (3H, br.s), 3.3–3.5(2H, m), 4.81(1H, m), 5.26,5.37(2H, ABq, J=19.1 Hz), 5.45(2H, s), 6.55(1H, s), 7.36(1H, s), 7.90(1H, dd, J=2.4 Hz,9.3 Hz), 8.03(1H, dd, 2.4 Hz, J=9.8 Hz), 9.2–9.4(2H, m)

Isomer B mp: above 230° C. (decomposed). NMR(DMSO-d₆)δ: 0.88(3H, t, J=7.3 Hz), 1.88(2H, m), 2.3–2.6(2H, m), 2.70 (3H, br.s), 3.3–3.5(2H, m), 4.82(1H, m), 5.26,5.37(2H, ABq, J=19 Hz), 5.45(2H, s), 6.54(1H, s), 7.36(1H, s), 7.91(1H, dd, J=2.4 Hz,9.3 Hz), 8.03(1H, dd, 2.4 Hz, J=10.3 Hz), 9.2–9.5 (2H, m)

Example 48

Preparation of (9S)-1-amino-9-ethyl-5-fluoro-2,3-dihydro-9-hydroxy-1H,12H-benzo[de]pyrano[3',4':6, 7]indolizino[1,2-b]quinoline-10,13(9H,15H)-dione Hydrochloride

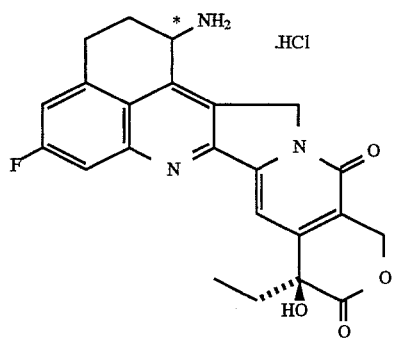

(1) 2,8-Diacetylamino-6-fluoro-1-tetralone

To 60 ml of a THF solution containing 2.28 gm of potassium-t-butoxide was slowly added 90 ml of a THF solution containing 3 gm of the compound obtained in Example 44-(7). After stirring for 10 minutes, 2.44 ml of n-butyl nitrite was added to the mixture, followed by further stirring for 1 hour at room temperature. The reaction mixture was poured into a dilute hydrochloric acid solution and extracted 3 times with chloroform. The extract was washed with water and saturated brine and dried over anhydrous sodium sulfate. The solvent was evaporated, and to the residue were added 87 ml of acetic acid and 87 ml of acetic anhydride, followed by adding thereto 11 gm of zinc powder at room temperature while stirring. After the addition, the stirring was continued for a further 10 minutes. Insoluble substances were removed by filtration, the solvent was evaporated, and the residue was dissolved into 100 ml of chloroform. This solution was washed with water, saturated aqueous solution of sodium hydroxide, and saturated brine in this order, was dried over anhydrous sodium sulfate. After evaporating the solvent, the residue was subjected to silica gel column chromatography using a hexane-ethyl acetate (2:3) mixed solvent as an eluant to obtain fractions containing the target compound. The fractions were concentrated to produce 2.82 gm of the title compound.

NMR(CDCl₃)δ: 1.8–2.0(1H, m), 2.11(3H, s), 2.14(3H, s), 2.67(1H, m), 3.02(1H, m), 3.25(1H, m), 4.65(1H, ddd, J=4.9 Hz,5.4 Hz,13.2 Hz), 6.48(1H, br.s), 6.64(1H, dd, J=8.3 Hz, 2.4 Hz), 8.43(1H, dd, J=8.2 Hz, 2.4 Hz)

(2) 8-Amino-6-fluoro-2-trifluoroacetylamino-1-tetralone 20 ml of concentrated hydrochloric acid was added to 1.23 gm of the compound prepared in (1) above, and the mixture was stirred at 100° C. for 12 hours. After cooling to the room temperature, 200 ml of water was added and the mixture washed twice with chloroform. The water layer was alkalinized by the addition of sodium hydroxide and extracted 4 times with chloroform. The extract was washed with saturated brine and dried over anhydrous sodium sulfate. The solvent was evaporated, and the residue was dissolved into 50 ml of dried THF. To the solution was added 0.59 ml of triethylamine. Then, 10 ml of THF solution containing 0.6 ml of trifluoroacetic anhydride was added dropwise to the mixture while stirring and cooling in an ice-salt bath. After stirring for 1 hour at the same temperature, 5 ml of water was added and the solvent was evaporated. 30 ml of water was added to the residue and the mixture was extracted 3 times with chloroform. The extract was dried over anhydrous sodium sulfate. After removal of the solvent by evaporation, the residue was subjected to silica gel column chromatography using chloroform as an eluant to obtain fractions containing the target compound. The fractions were concentrated to obtain 1.1 gm of the title compound.

NMR(CDCl$_3$)δ: 1.88(1H, ddd, J=4.4 Hz, 13.2 Hz,25.4 Hz), 2.79(1H, m), 2.97(1H, m), 3.15(1H, m), 4.50(1H, ddd, J=4.4 Hz,4.9 Hz,13.2 Hz), 6.21(2H, m)

(3) (9S)-1-Amino-9-ethyl-5-fluoro-2,3-dihydro-9-hydroxy-12 H-benzo[de]pyrano[3',4':6,7]indolizino [1,2-b]quinoline-10, 13(9H,15H)-dione Hydrochloride 144 mg of the compound prepared in (2) above and 130 mg of trione were added to 30 ml of toluene. To this was added a catalytic amount of PPTS to react the mixture in a Deanstark apparatus under heating with refluxing for 41 hours. The reaction mixture was cooled and the solvent was evaporated. The residue was subjected to silica gel column chromatography using a chloroform-methanol (99:1) mixed solvent as an eluant to obtain fractions containing the target compound. The fractions were concentrated, and 5 ml of methanol, 5 ml of water, and 4 ml of 4N hydrochloric acid were added to the concentrate, followed by the stirring at 80° C. for 5 hours. After concentration, 4 ml of water was added to the resulting product to remove insoluble substances by filtration. The filtrate was purified with HPLC (CAPCELL PAK C18) using a mixture of acetonitrile-water-1N hydrochloric acid (22:78:1) to obtain 19 mg of Isomer A and 16 mg of Isomer B of the title compound.

Isomer A mp: above 200° C. (decomposed). NMR(DMSO-d$_6$)δ: 0.89(3H, t, J=7.3 Hz), 1.89(2H, m), 2.15–2.27(1H, m), 2.40–2.55(1H, m), 3.20–3.45(2H, m), 5.07(1H, m), 5.42, 5.84(2H, ABq, J=19.5 Hz), 5.46(2H, s), 6.55(1H, s), 7.38 (1H, s), 5.46(2H, s), 6.55(1H, s), 7.38(1H, 7.60(1H, dd, J=2.4 Hz,9.3 Hz), 7.86(1H, dd, 2.4 Hz, J=10.3 Hz), 8.2–8.6 (3H, m)

Isomer B mp: above 210° C. (decomposed). NMR(DMSO-d$_6$)δ: 0.88(3H, t, J=7.3 Hz), 1.88(2H, m), 2.15–2.27(1H, m), 2.45–2.60(1H, m), 3.20–3.45(2H, m), 5.12(1H, m), 5.42, 5.83(2H, ABq, J=19.1 Hz), 5.46(2H, s), 6.55(1H, s), 7.38 (1H, s), 7.62(1H, dd, J=2.4 Hz,8.8 Hz), 7.86(1H, dd, 2.4 Hz, J=10.2 Hz), 8.4–8.6(3H, m), 7.86(1H, dd, 2.4 Hz, J=10.2 Hz), 8.4–8.6(3H, m)

Example 49

Preparation of (9S)-1-amino-9-ethyl-4,5-difluoro-9-hydroxy-2,3-dihydro-1H,12H-benzo[de]pyrano[3', 4':6,7]indolizino[1,2-b]quinoline-10,13(9H,15H)-dione Hydrochloride

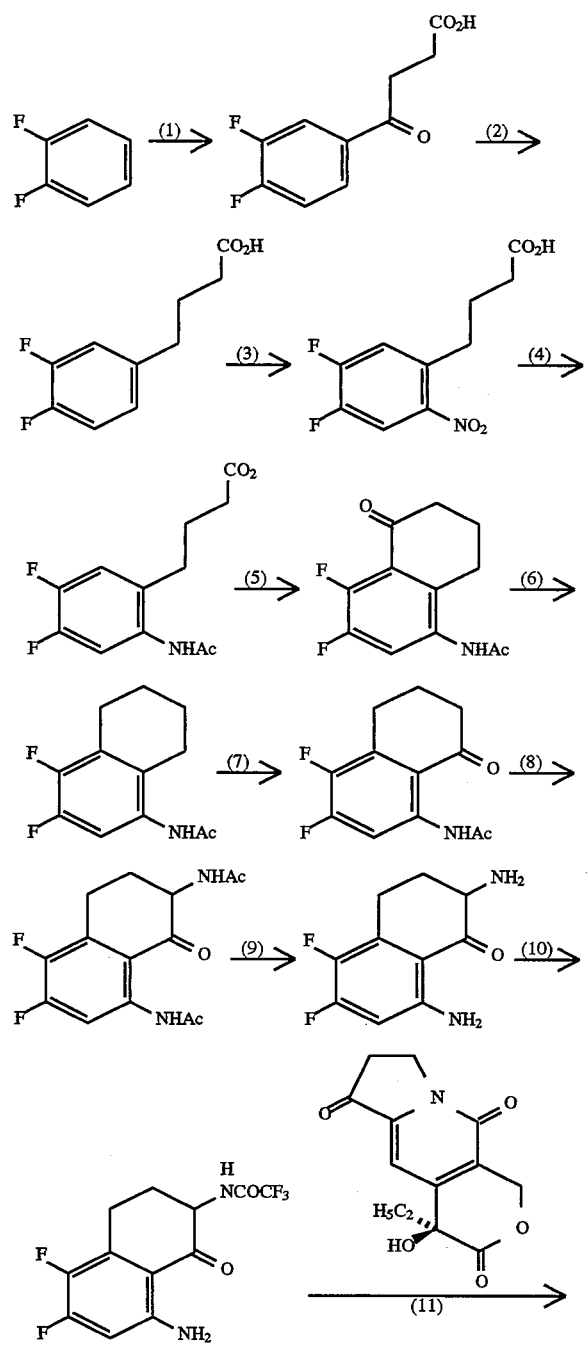

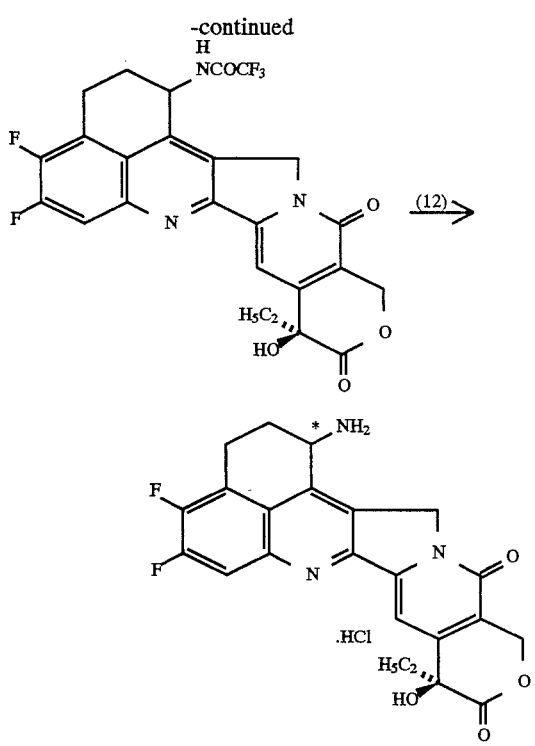

(1) 4-(3,4-Difluorophenyl)-4-oxobutanoic Acid 45 gm of succinic anhydride and 130.7 gm of aluminum chloride were added to 57 gm of difluorobenzene, and the mixture was heated under reflux for 4 hours. Upon the addition of 200 ml of 1% hydrochloric acid aqueous solution, the reaction mixture was extracted with chloroform, washed with water, and dried over anhydrous sodium sulfate. The solvent was evaporated and the residue was subjected to silica gel column chromatography using a chloroform-methanol (30:1) mixed solvent as an eluant to obtain fractions containing the target compound. The fractions were concentrated to produce 30 gm of the title compound.

NMR(CDCl$_3$)δ: 2.82(2H, t, J=7 Hz), 3.26(2H, t, J=7 Hz), 7.0–7.9(3H, m)

(2) 4-(3,4-Difluorophenyl)-4-butanoic Acid

The compound obtained in (1) above (30 gm) was dissolved into 200 ml of acetic acid. To the solution were added 8 ml of 60% perchloric acid and 10% palladium-on-carbon to effect catalytic hydrogenation under 6.5 atm. The catalyst was removed by filtration and acetic acid was evaporated. Upon the addition of 600 ml of ethyl acetate, the residue was washed with water and dried over anhydrous sodium sulfate. The solvent was evaporated to obtain 26 gm of the title compound.

NMR(CDCl$_3$)δ: 1.8–2.1(2H, m), 2.37(2H, t, J=7 Hz), 2.64(2H, t, J=7 Hz), 6.9–7.1(3H, m)

(3) 4-(4,5-Difluoro-2-nitrophenyl)butanoic Acid

The compound obtained in (2) above (500 mg) was added to 4 ml of cold concentrated sulfuric acid, and to the mixture was dropwise added 2.5 ml concentrated sulfuric acid solution containing 371 mg of potassium sulfate while maintaining the internal temperature below 5° C. After the addition, the mixture was stirred for a further 30 minutes. The reaction product was poured into ice-cold water and extracted with 100 ml of chloroform. The chloroform layer was dried over anhydrous sodium sulfate and the solvent was evaporated to obtain 480 mg of the title compound.

NMR(CDCl$_3$)δ: 1.8–2.1(2H, m), 2.48(2H, t, J=7 Hz), 2.9–3.0(2H, m), 7.21(1H, dd, J=7 Hz,10 Hz), 7.90(1H, dd, J=7 Hz,10 Hz)

(4) 4-(2-Acetylamino-4,5-difluorophenyl)butanoic Acid

The compound obtained in (3) above (380 mg) was dissolved in a mixed solvent of 5 ml of acetic acid and 10 ml of acetic anhydride. Upon the addition of 60 mg of 10% palladium-on-carbon, the mixture was catalytically hydrogenated. The catalyst was removed by filtration, the solvent was evaporated, and the residue was subjected to silica gel column chromatography using a chloroform-methanol (10:1) mixed solvent as an eluant to obtain fractions containing the target compound. The fractions were concentrated to produce 90 mg of the title compound.

NMR(CDCl$_3$)δ: 1.7–1.9(2H, m), 2.29(3H, s), 2.4–2.6(4H, m), 6.93(1H, dd, J=8 Hz,12 Hz), 8.09(1H, dd, J=8 Hz,12 Hz), 8.53(1H, br s)

(5) 5-Acetylamino-7,8-difluoro-1-tetralone

The compound obtained in (4) above (9.07 gm) was dissolved into 450 ml of dichloromethane. To the mixture was added 7.71 gm of phosphorous pentachloride while stirring at room temperature. After stirring for a further 1 hour, the reaction mixture was concentrated and dichloromethane was added to the residue. Dichloromethane was evaporated again and 500 ml of 1,2-dichloroethane and 9.88 gm of anhydrous aluminum chloride were added to the residue. The mixture was stirred for 1 hour at 70° C. and gently heated under reflux for 15 hours. The reaction product was poured into ice-cold water, extracted with chloroform, washed with saturated brine, and dried over anhydrous sodium sulfate. The solvent was evaporated and the residue was subjected to silica gel column chromatography using chloroform-methanol (50:1) as an eluant to obtain fractions containing the target compound. The fractions were concentrated to obtain 2.31 gm of the title compound.

NMR(CDCl$_3$)δ: 2.1–2.2(2H, m), 2.23(3H, s), 2.5–2.7(2H, m), 2.7–2.9(2H, m), 6.93(1H, br s), 7.84(1H, dd, J=7 Hz,11 Hz)

(6) 5-Acetylamino-7,8-difluoro-1,2,3,4-tetrahydronaphthalene

The compound obtained in (5) above (1 gm) was dissolved into 20 ml of ethanol. To the solution was added 166 mg of sodium borohydride while stirring at room temperature. After stirring for 20 minutes, chloroform and 10% citric acid were added to the reaction mixture. The chloroform layer was extracted and concentrated. To the concentrate were added 20 ml of toluene and a small amount of p-TsOH, followed by heating under reflux for 1 hour. Upon addition of 100 ml of ethyl acetate, the reaction product was washed with saturated brine and dried over anhydrous sodium sulfate. The solvent was evaporated and the residue was dissolved into a mixed solvent of 20 ml of ethanol, 20 ml of dioxane, and 0.2 ml of acetic acid. The mixture was catalytically hydrogenated with the addition of 200 mg of platinum oxide. The catalyst was removed, the filtrate was concentrated, and ether was added to the concentrate. 0.8 gm of the title compound was obtained by collecting the precipitate by filtration.

NMR(CDCl$_3$)δ: 1.79(4H, br s), 2.18(3H, s), 2.52(2H, br s) 2.73(2H, br s), 6.91(1H, br s), 7.4–7.6(1H, m)

(7) 8-Acetylamino-5,6-difluoro-1-tetralone

To a solution of the compound obtained in (6) above (810 mg) in 30 ml of acetone was added 3 ml of 15% aqueous solution of magnesium sulfate. 1.17 gm of potassium permanganate was slowly added to the mixture while stirring. After 1 hour, the reaction product was extracted with chloroform, the extract was washed with water and saturated brine, and dried over anhydrous sodium sulfate. The solvent was evaporated to obtain 806 mg of the title compound.

NMR(CDCl$_3$)δ: 2.05–2.17(2H, m), 2.23(3H, s), 2.68(2H, t, J=5.85 Hz), 3.00(2H, t, J=5.85 Hz), 8.61(1H, dd, J=7.8 Hz,13.2 Hz), 12.1–12.23(1H, br s)

(8) 2,8-Diacetylamino-5,6-difluoro-1-tetralone

To a mixed solution of 15 ml of a THF solution and 1.5 ml of tert-butanol containing 309 mg of potassium-butoxide was added slowly in a nitrogen stream at 0° C. 300 mg of the compound prepared in (7) above dissolved in 7.5 ml of THF. After stirring for 10 minutes at the same temperature, 0.22 ml of n-butyl nitrite was dropwise added to the mixture, followed by further stirring for 1.5 hours, during which the temperature was slowly raised to 20° C. The reaction mixture was adjusted to pH 1 with the addition of 1N hydrochloric acid, extracted with chloroform, washed with saturated brine, and dried over anhydrous sodium sulfate. To the residue obtained by evaporating the solvent was added a mixture of 15 ml of acetic acid and 15 ml of acetic anhydride, and was added about 1 gm of zinc powder, followed by stirring at 20° C. for 18 hours. Insoluble substances were removed by filtration, the solvent was evaporated, and the residue was extracted with chloroform. The extract was washed with saturated brine and dried over anhydrous sodium sulfate. After evaporating the solvent, the residue was subjected to silica gel column chromatography using a chloroform-methanol (97:3) mixed solvent as an eluant to obtain fractions containing the target compound. The fractions were concentrated to produce 311 mg of the title compound.

NMR(CDCl$_3$)δ: 1.83–1.94(1H, m), 2.10(3H, s), 2.21(3H, s), 2.59–2.67(1H, m), 2.92–3.01(1H, m), 3.18–3.26(1H, m), 4.62–4.68(1H, m), 6.70(1H, d, J=5.9 Hz), 8.56(1H, dd, J=7.3 Hz,13.2 Hz), 11.64–11.67(1H, br s)

(9) 2,8-Diamino-5,6-difluoro-1-tetralone 50 ml of 3N hydrochloric acid was added to 300 mg of the compound obtained in (8) above, and the mixture was stirred at 60° C. for 3.5 hours. After the addition of 15 ml of concentrated hydrochloric acid, the mixture was stirred at 90° C. for 30 minutes, cooled, and neutralized with sodium bicarbonate. The product was extracted with 300 ml of chloroform, washed with saturated brine, and dried over anhydrous sodium sulfate. The solvent was evaporated to obtain 140 mg of the title compound.

NMR(CDCl$_3$)δ: 1.79–1.93(1H, m), 2.68–2.81(2H, m), 3.16–3.20(1H, m), 3.53–3.56(1H, m), 6.26–6.29(2H, m), 6.34–6.45(2H, m), 7.28(1H, s)

(10) 8-Amino-5,6-difluoro-2-trifluoroacetylamino-1-tetralone

The compound obtained in (8) above (140 mg) was dissolved into 10 ml of THF and cooled to 0° C. To the solution were added 75 mg of triethylamine, and then 155 mg trifluoroacetic anhydride slowly, followed by stirring for 1.5 hour. After the addition of saturated aqueous solution of sodium bicarbonate, the mixture was extracted with chloroform, washed with saturated brine and dried over anhydrous sodium sulfate. After removal of the solvent by evaporation, the residue was subjected to silica gel column chromatography using chloroform-methanol (97:3) as an eluant to obtain fractions containing the target compound. The fractions were concentrated to obtain 93 mg of the title compound.

NMR(CDCl$_3$)δ: 1.85(1H, ddd, J=4.4 Hz, 13 Hz, 26.1 Hz), 2.75–2.84(2H, m), 3.20–3.26(1H, m), 4.5(1H, dd, J=4.9 Hz, 13.7 Hz), 6.31(1H, dd, J=6.3 Hz, 11.7 Hz), 6.35–6.44(2H, br s), 7.54–7.6(1H, br s)

(11) (9S)-9-Ethyl-4,5-difluoro-2,3-dihydro-9-hydroxy-1-trifluoroacetylamino-1H,12H-benzo[de]pyrano[3',4':6,7]indolizino[1,2-b]quinoline-10,13 (9H,15H)-dione The compound obtained in (10) above (90 mg) was dissolved into 20 ml of toluene, and, after the addition of 81 mg of trione, the mixture was heated under reflux for 111 hours in a nitrogen stream. The reaction product was concentrated and the residue was subjected to silica gel column chromatography using chloroform-methanol (30:1) as an eluant to obtain fractions containing the target compound. The fractions were concentrated to obtain 98 mg of the title compound.

NMR(CDCl$_3$)δ: 1.01(3H, t, J=7 Hz), 1.80–1.83(2H, m), 2.01(1H, s), 2.33(1H, s), 2.96(1H, dd, J=6.35 Hz, 7.32 Hz), 4.32–4.36(1H, m), 5.23(3H, dd, J=6.35 Hz, 17.1 Hz), 5.67 (1H, d, J=17.1 Hz), 7.55(1H, s)

(12) (9S)-1-Amino-9-ethyl-4,5-difluoro-2,3-dihydro-9-hydroxy-1H,12H-benzo[de]pyrano[3',4':6,7]indolizino[1,2-b]quinoline-10,13(9H,15H)-dione Hydrochloride 30 ml of 1N hydrochloric acid was added to 95 mg of the compound prepared in (11) above, and the mixture was heated under reflux for 1 hour. The solvent was evaporated and 30 ml of water was added to remove insoluble substances by filtration. The filtrate was purified with HPLC (CAPCELL PAK C18) using a mixture of acetonitrile-water-1N hydrochloric acid (20:80:1) to obtain 6.2 mg of Isomer A and 5.9 mg Isomer B of the title compound.

Isomer A

IRν$_{max}^{KBr}$ cm$^{-1}$: 3416, 1746, 1660, 1602, 1512. NMR (DMSO-d$_6$)δ: 0.87(3H, t, J=7.3 Hz), 1.82–1.91(2H, m), 2.15–2.26(1H, m), 5.11–5.18(1H, br s), 5.44,5.84(2H, ABq, J=19 Hz), 5.45(2H, s), 7.35(1H, s), 8.18(1H, dd, J=7.8 Hz, 11.5 Hz), 8.55–8.64(3H, br). MASS m/z: 439(M$^+$)

Isomer B

IRν$_{max}^{KBr}$ cm$^{-1}$: 2932, 1750, 1658, 1596, 1508. NMR (DMSO-d$_6$)δ: 0.86(3H, t, J=7.3 Hz), 1.83–1.9(2H, m), 2.15–2.24(1H, m), 5.12–5.16(1H, br s), 5.44,5.82(2H, ABq, J=19 Hz), 5.45(2H, s), 6.55(1H, s), 7.35(1H, s), 8.19(1H, dd, J=7.8 Hz, 11.5 Hz), 8.53–8.66(3H, br). MASS m/z: 439(M$^+$)

Example 50

Preparation of (9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione Hydrochloride

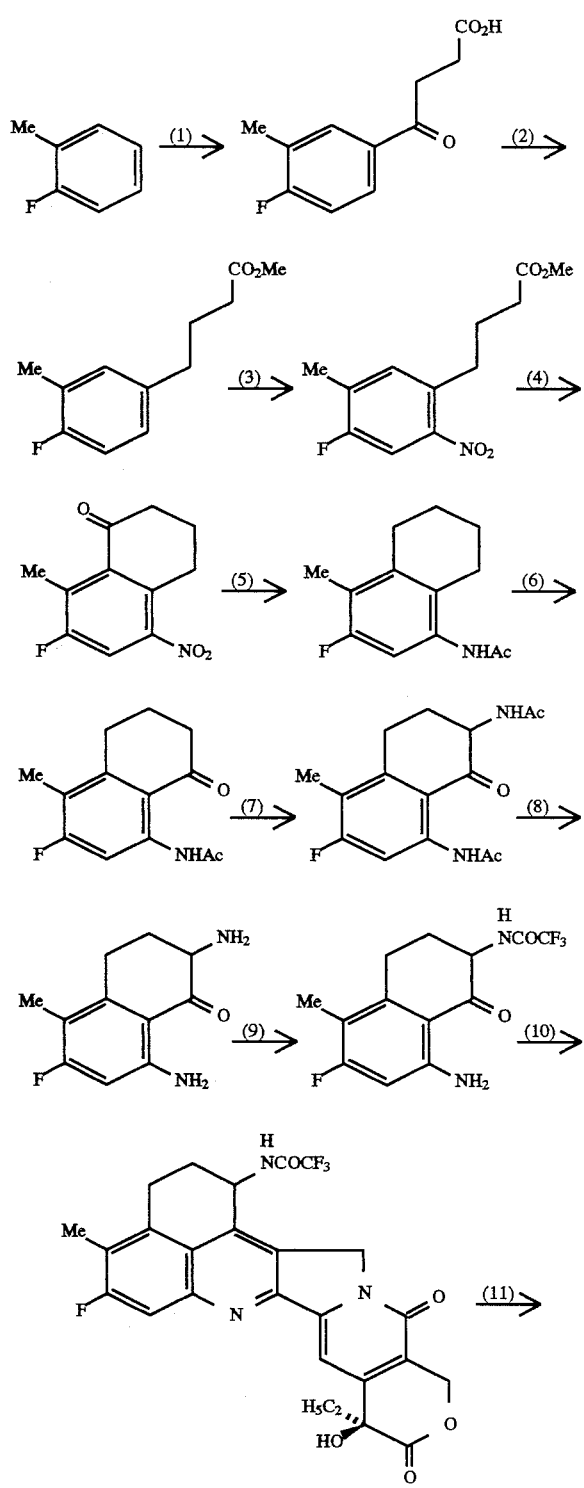

(1) 4-(4-Fluoro-3-methylphenyl)-4-oxobutanoic Acid 200 gm of succinic anhydride and 800 gm of aluminum chloride were added to 250 ml of 2-fluorotoluene, and the mixture was heated at 80° C. for 1 hour. Upon the addition of 5 l of 1% cold hydrochloric acid aqueous solution, the reaction mixture was extracted with ethyl acetate, washed with 1N hydrochloric acid and water, and dried over anhydrous sodium sulfate. The solvent was evaporated to obtain 345 gm of the title compound.

NMR(CDCl$_3$)δ: 1.89–1.97(2H, m), 2.24(3H, s), 2.36(2H, t, J=7.3 Hz), 2.60(2H, t, J=7.3 Hz), 6.84–6.99(3H, m)

(2) Methyl 4-(4-fluoro-3-methylphenyl)butanoate

The compound obtained in (1) above (172 gm) was dissolved into 700 ml of acetic acid. To the solution were added 10 ml of 40% perchloric acid and 30 gm of 10% palladium-on-carbon to effect catalytic hydrogenation under 6 atm. The catalyst was removed by filtration and acetic acid was evaporated. Upon the addition of 2 l of water, the residue was extracted with chloroform, washed with saturated brine, and dried over anhydrous sodium sulfate. The solvent was evaporated and 1 l of methanol was added to the residue. After cooling to 0° C. 269 gm of thionyl chloride was slowly dropped to the solution, followed by the addition of 10 ml of dimethylformamide. The mixture was stirred for 12 hours at room temperature, the reaction product was concentrated, and extracted with chloroform. The extract was washed with water and saturated brine, and dried over anhydrous magnesium sulfate. The solvent was evaporated to obtain 153 gm of the title compound.

NMR(CDCl$_3$)δ: 1.91(2H, quintet, J=7.5 Hz), 2.24(3H, d, J=2 Hz), 2.31(2H, t, J=7.5 Hz), 2.57(2H, t, J=7.5 Hz), 3.66(3H, s), 6.89(1H, t, J=9 Hz), 6.93(1H, ddd, J=9 Hz, 5 Hz, 3 Hz), 6.97(1H, dd, J=7 Hz, 3 Hz)

(3) Methyl 4-(4-fluoro-3-methyl-6-nitrophenyl)butanoate

The compound obtained in (2) above (10.9 gm) was added to 6 ml of cold concentrated sulfuric acid, and to the mixture was dropwise added 5.8 gm of potassium nitrate in 15 ml of concentrated sulfuric acid, while maintaining the internal temperature below 5° C. After the addition, the mixture was stirred for a further 20 minutes. The reaction product was poured into ice-cooled water and extracted with ethyl acetate. The ethyl acetate layer was dried over anhydrous sodium sulfate and the solvent was evaporated. The residue was subjected to silica gel column chromatography using a hexane-ethyl acetate (90:7) mixed solvent as an eluant to obtain fractions containing the target compound. The fractions were concentrated to produce 7.1 gm of the title compound.

NMR(CDCl$_3$)δ: 1.97(2H, quintet, J=8 Hz), 2.34(3H, d, J=2 Hz), 2.41(2H, t, J=8 Hz), 2.90(2H, t, J=8 Hz), 3.69(3H, s), 7.18(1H, d, J=7 Hz), 7.66(1H, d, J=9 Hz)

(4) 7-Fluoro-8-methyl-5-nitro-1-tetralone

The compound obtained in (3) above (7.1 gm) was dissolved in 20 ml of methanol. To the solution was added 10 ml of 15% aqueous solution of sodium hydroxide and the mixture was stirred for 3 hours at room temperature. The reaction mixture was concentrated, acidified with concentrated hydrochloric acid, and extracted with chloroform. The chloroform layer was washed with water and saturated brine in this order and dried over anhydrous sodium sulfate. The solvent was evaporated, and the residue was slowly added to 50 ml of polyphosphoric acid heated to 110° C. and stirred for 4.5 hours. After the addition of 100 ml of ice-water, the reaction product was extracted with ethyl acetate, washed with water, saturated sodium bicarbonate and saturated brine in this order, and dried over anhydrous sodium sulfate. The solvent was evaporated, and the residue was subjected to silica gel column chromatography using a hexane-ethyl acetate (1:1) mixed solvent as an eluant to obtain fractions containing the target compound. The fractions were concentrated to produce 1.7 gm of the title compound.

NMR(CDCl$_3$)δ: 2.11(2H, quintet, J=7 Hz), 2.60(3H, d, J=2 Hz), 2.72(2H, t, J=7 Hz), 3.14(2H, t, J=6.0 Hz), 7.74 (1H, d, J=9 Hz)

(5) 5-Acetylamino-7-fluoro-8-methyl-1,2,3,4-tetrahydronaphthalene

The compound obtained in (4) above (1.35 gm) was dissolved into 5 ml of ethanol and 15 ml of THF. To the solution was added 114 mg of sodium borohydride while stirring at room temperature. After stirring for 20 minutes, the reaction mixture was concentrated. To the concentrate were added 25 ml of toluene and 840 mg of p-TsOH, followed by heating under reflux for 30 minutes. Upon the addition of 100 ml of ethyl acetate, the reaction product was washed with saturated brine and dried over anhydrous sodium sulfate. The solvent was evaporated and the residue was dissolved into 20 ml of ethyl acetate and catalytically hydrogenated with the addition of 400 mg of platinum oxide for 4 hours. The catalyst was removed, the fitrate was concentrated, and 10 ml of dichloromethane was added to the concentrate. After the further addition of 1.2 ml of triethylamine and 0.81 ml of acetic anhydride, the mixture was stirred for 40 minutes. The reaction product was diluted with 50 ml of chloroform, washed with dilute hydrochloric acid, saturated sodium bicarbonate and saturated brine in this order, and dried over anhydrous sodium sulfate. The solvent was evaporated to obtain 1.23 gm of the title compound.

NMR(CDCl$_3$)δ: 1.79(4H, s), 2.10(3H, s), 2.19(3H, s), 2.53(2H, s), 2.62(2H, s), 7.46(1H, d, J=9 Hz)

(6) 8-Acetylamino-6-fluoro-5-methyl-1-tetralone 1.2 gm of the compound obtained in (5) above was reacted in the same manner as in Example 49-(7) and post-treated to obtain 825 mg of the title compound.

NMR(CDCl$_3$)δ: 2.08(2H, quintet, J=7 Hz), 2.15(3H, d, J=2 Hz), 2.22(3H, s) 2.66(2H, t, J=7 Hz), 2.88(2H, t, J=6 Hz), 8.42(1H, d, J=13 Hz)

(7) 2,8-Diacetylamino-6-fluoro-5-methyl-1-tetralone 4.7 gm of the compound obtained in (6) above was reacted in the same manner as in Example 49-(8) and post-treated to obtain 3.85 gm of the title compound.

NMR(CDCl$_3$)δ: 1.7–1.9(1H, m), 2.11(3H, s), 2.15(3H, s), 2.23(3H, s), 2.7–2.8(1H, m), 2.9–3.1(2H, m), 4.5–4.7(1H, m), 6.53(1H, br s), 8.43(1H, dq, J=13 Hz), 11.76(1H, s)

(8) 2,8-Diamino-6-fluoro-5-methyl-1-tetralone 3.85 gm of the compound obtained in (7) above was added to 100 ml of 6N hydrochloric acid, and the mixture was stirred at 80° C. for 6 hours. The reaction mixture was poured into 100 ml of water, adjusted to pH 10 with the addition of 15% aqueous solution of sodium hydroxide, and extracted with chloroform. The extract was washed with water and saturated brine in this order and dried over anhydrous sodium sulfate. The solvent was evaporated to obtain 1.66 gm of the title compound.

NMR(CDCl$_3$)δ: 1.83(1H, dq,. J=13 Hz, 4 Hz), 2.04(3H, s), 2.25–2.4(1H, m), 2.75(1H, ddd, J=14 Hz, 13HZ, 4 Hz), 2.98(1H, ddd, J=14 Hz, 4 Hz, 3 Hz), 3.53(1H, dd, J=13HZ, 4 Hz), 6.20(1H, d, J=12 Hz), 6.42(1H, br s)

(9) 8-Amino-6-fluoro-5-methyl-2-trifluoroacetylamino-1-tetralone

The compound obtained in (8) above (1.66 gm) was dissolved into a mixed solvent of 70 ml of ethanol and 10 ml of THF. To the solution were added 2 ml of triethylamine and 1.5 ml of ethyltrifluoroacetate, followed by stirring for 20 hours at 20° C. The reaction product was added to dilute aqueous solution of hydrochloric acid and extracted with chloroform. The extract was washed with water, saturated sodium bicarbonate and saturated brine in this order, and dried over anhydrous sodium sulfate. After removal of the solvent by evaporation, the residue was subjected to silica gel column chromatography using chloroform as an eluant to obtain fractions containing the target compound. The fractions were concentrated to obtain 1.79 gm of the title compound.

NMR(CDCl$_3$)δ: 1.81(1H, dq, J=13 Hz, 5 Hz), 2.06(3H, d, J=0.5 Hz), 2.8–3.1(3H, m), 4.48(1H, dt, 13 Hz, 4 Hz), 6.26(1H, d, J=13 Hz), 7.64(1H, br s)

(10) (9S)-9-Ethyl-5-fluoro-2,3-dihydro-9-hydroxy-4-methyl-1-trifluoroacetylamino-1H,12H-benzo[de]pyrano [3',4':6,7]indolizino[1,2-b]quinoline-10,13 (9H,15H)-dione The compound obtained in (9) above (4 gm) and trione (4.57 gm) were reacted for 47 hours in the same manner as Example 49-(11) and post-treated to obtain 4.21 gm of the title compound.

NMR(MeOH-d$_4$+CDCl$_3$)δ: 0.94, 0.96(3H, each t, J=7 Hz), 1.75–1.95(2H, m), 2.36(3H, s), 2.3–2.5(2H, m), 3.05–3.35(2H, m), 5.05–5.75(5H, m), 7.30(0.5H, d, J=11 Hz), 7.45(0.5H, s), 7.56(0.5H, d, J=11 Hz), 7.57(0.5H, s)

(11) (9S)-1-Amino-9-ethyl-5-fluoro-2,3-dihydro-9-hydroxy-4-methyl-1H,12H-benzo[de]pyrano[3',4':6, 7]indolizino[1,2-b]quinoline-10,13(9H,15H)-dione Hydrochloride 625 mg of the compound prepared in (10) above was added to a mixed solution of 7.5 ml of concentrated hydrochloric acid, 18 ml of methanol and 12 ml of water, and stirred at 80° C. for 7 hours. Insoluble substances were removed by filtration and the filtrate was purified with HPLC (CAPCELL PAK C18) using a mixture of acetonitrile-water-1N hydrochloric acid (20:80:1) to obtain 138 mg of Isomer A and 143 mg Isomer B of the title compound.

Isomer A mp: 220°–250° C. (Decomposed). $[\alpha]_D^{20}=+198°$ (c=0.42, in H$_2$O) IRv$_{max}^{KBr}$ cm$^{-1}$: 3400, 1748, 1660, 1592. NMR (D$_2$O)δ: 0.73(3H, t, J=7.3 Hz), 1.74(2H, q, J=7.3 Hz), 2.13(3H, s), 2.45–2.55(1H, m), 2.6–2.7(1H, m), 2.85–3.0 (1H, m), 3.2–3.3(1H, m), 5.11(1H, m), 5.18, 5.25(2H, ABq, J=19 Hz), 5.18, 5.32(2H, ABq, J=16 Hz), 7.05(1H, s), 7.09(1H, d, J=11 Hz)

Isomer B mp: 220°–230° C. (Decomposed). NMR(D$_2$O)δ: 0.82 (3H, t, J=7.3 Hz), 1.83(2H, q, J=7.3 Hz), 2.13(3H, s), 2.1–2.3(1H, m), 2.5–2.6(1H, m), 2.9–3.1(1H, m), 3.1–3.3 (1H, m), 4.97(1H, br s), 5.06, 5.32(2H, ABq, J=19 Hz), 5.24, 5.37(2H, ABq, J=16 Hz), 6.99(1H, d, J=11 Hz), 7.16(1H, s)

Obviously, numerous modifications and variations of the present invention are possible in light of the above teachings. It is therefore to be understood that within the scope of the appended claims, the invention may be practiced otherwise than as specifically described herein.

1-1. Activity of DX-8951 on Cells (in vitro)

Test Method (MTT method):

See page 11 of the parent specification. In detail, p388 murine leukemia cells, MKN 28 (human stomach cancer cells), QG56 (human lung cancer cells) and HOC21 (human ovarian cancer cells) were provided. The cells were spread over a 96-well microplate, respectively, and a sample to be tested was added to each of them after 24 hours. Cells were cultivated under the conditions of 5% CO$_2$ at 37° C. for 3 days. 3-(4,5-Dimethylthiazol-2-yl)-2,5-diphenyl-2H-tetrazolium bromide (abbriviated as MTT) was added thereto 4 hours after the addition of the sample. Upon the addition of 200 µl/ml of isopropyl alcohol containing 0.04N HCl, the absorption at 540 nm was measured to determine IC$_{50}$.

The results are shown in Table 2-1.

TABLE 2-1

| Cells | IC$_{50}$ (ng/ml) | |
|---|---|---|
| | DX-8951 | SN-38 |
| p388 | 0.58 | 1.33 |
| MKN28 | 9.40 | 61.0 |
| QG56 | 0.67 | 2.46 |
| HOC21 | 12.80 | 53.2 |

1-2. In vitro Anti-proliferative Activities

In vitro anti-proliferative activities of the drugs against 4 human and 1 murine cell lines were measured by the MTT assay (see page 11 of the parent specification) after 3 days incubation, and expressed as the doses required to inhibit growth of 50% cells cultivated (GI$_{50}$, ng/ml).

The results are shown in Table 2-2.

TABLE 2-2

| in vitro anti-proliferative activity (GI$_{50}$, ng/ml) | | | |
|---|---|---|---|
| Tumor cells | DX-8951 | CPT-11*) | SN-38**) |
| MCF-7 (Breast) | 0.16 | 1198 | 0.49 |
| MKN28 (Stomach) | 1.75 | 8691 | 21.67 |
| QG90 (Lung) | 0.66 | 1553 | 1.43 |

TABLE 2-2-continued

| in vitro anti-proliferative activity (GI$_{50}$, ng/ml) | | | |
|---|---|---|---|
| Tumor cells | DX-8951 | CPT-11*) | SN-38**) |
| HOC-21 (Ovary) | 3.67 | 15062 | 21.36 |
| p388 (Mouse leukemia) | 1.06 | 2854 | 3.22 |
| MEAN | 1.46 | 5872 | 9.63 |

*) Miyasaka, Example 19 compound (irinotecan,INN)
**) SN-38 is a compound known to be the active center of CPT-11. (SN38: 7-Ethyl-10-hydroxycamptothecin)

2. In vivo Anti-tumor Activities

In vivo anti-tumor activities of drugs were assayed with Meth A fibrosarcoma in BALB/c mice. Mice were treated intravenously with several doses of drugs on days 5, 6, 7, and 8 (qd×4) after hypodermic tumor implantation, and the weight of the tumor masses measured on day 14. The anti-tumor activities of drugs against the tumor were expressed as the relative tumor weight of controls (%).

The results are shown in Table 3.

TABLE 3

| | Total Dose (mg/kg) | Tumor cell anti-proliferative activity (%) | Death Nos. |
|---|---|---|---|
| DX-8951 | 1.875 | 72.5 | 0/6 |
| | 3.75 | 78.3 | 0/6 |
| | 7.5 | 87.5 | 0/6 |
| | 15 | 96.6 | 0/6 |
| | 30 | 96.4 | 2/6 |
| CPT-11 | 25 | 31.4 | 0/6 |
| | 50 | 53.3 | 0/6 |
| | 100 | 62.3 | 0/6 |
| | 200 | 79.4 | 0/6 |

3. Topoisomerases Assay

Topoisomerase I was prepared from p388 mouse leukemia. One unit (the minimum amount of full relaxation of 0.5 µg SV40 DNA) of topoisomerase I, 0.5 µl of the test compounds, and 0.5 µg of SV40 DNA were added sequentially to the reaction buffer. The reaction mixture (50µl) was incubated for 10 min and 37° C. and analyzed by electrophoresis, the gel was stained with 0.05% ethydium bromide and photographed with UV light. The DNA was quantified using a densitometor. The inhibition rate of the topoisomerase activity was calculated as $$\left(1 - \frac{Frt - Fr}{Frc - Fr}\right) \times 100(\%)$$

where Frt and Frc are ratios of relaxed DNA to total DNA treated with topoisomerase in the presence and absence of the test drug, respectively. Fr is the proportion of relaxed DNA in untreated DNA. The IC$_{50}$ of each test drug was estimated from the dose-response.

| Inhibition of topoisomerase I-induced relaxation of supercoiled DNA by drugs ($IC_{50}$ (µg/ml)) | | | |
|---|---|---|---|
| | camptothecin | DX-8951 | SN-38 |
| $ID_{50}$ (µg/ml) | 15.3 | 0.53 | 1.40 |

4. Acute Toxicity in Mice

Groups of 5 male BALB/c mice were administered intravenously with several doses of drugs, and their survivals from death were recorded up to day 14. The 10 and 50% lethal doses ($LD_{10}$ and $LD_{50}$) were calculated form the survival rate on day 14 by the Probit method.

| Acute toxicity in mice (mg/m$^2$) | | |
|---|---|---|
| Compounds | $LD_{10}$ | $LD_{50}$ |
| DX-8951 | 228 | 270 |
| CPT-11 | 198 | 270 |

5. Diseases

The present compound DX-8951 (see claim 9, Ex.50) is considered to be effective against lung cancer, gastric cancer, colonic cancer, esophageal cancer, ovarial cancer, cervix cancer, breast cancer, hepatoma, head and neck cancer, leukemia, lymphoma, renal cancer and tisticular cancer.

6. Manner of Administration

The present compound can be administered in various manners such as via intravenous, intra muscular or subcutaneous injection and oral or percutaneous administration. Preferable manners of administration are intravenous injection and oral administration of the compound in an aqueous form, Aqueous preparations can be obtained by forming an acid addition salt between the compound and a pharmaceutically acceptable acid, or forming an alkali metal salt, such as a sodium salt. In case of oral administration, the compound can either be in a free form or a salt in the aqueous preparation.

The preparation can be obtained in a conventional process according to the manner of administration. Examples of the forms of the antitumor preparations of the present invention include tablets, powders, granules, capsules, liquid, syrups, elixirs, and oily or aqueous suspensions for oral route preparations. Injections may optionally include auxiliary ingredients such as stabilizers, preservatives, and solution aids. Solutions containing these auxiliary ingredients may be freeze-dried to form a solid preparation.

7. Dosage

Preferable dosage for non-oral administration is about 0.5 mg to 50 mg a day, more preferably about 1 mg to 20 mg a day, per 1 m$^2$ body surface. It is preferred that the present compound be administered to a subject in the above range at a time, and the administration be repeated every 3–4 weeks. In case of oral route-administration, it is preferred to administer the compound to a subject in an amount of from about 0.5 to 50 mg a day, more preferably about 1 to 20 mg a day, per 1 m$^2$ body surface at a time and to repeat the administration at a suitable interval.

What is claimed is:

1. (9S)-1-Amino-9-ethyl-5-fluoro-2,3-dihydro-9-hydroxy-4-methyl-1H,12H-benzo-[de]pyrano[3',4':6,7] indolizino[1,2-b]quinoline-10,13(9H,15H)-dione hydrochloride.

2. (9S)-1-Amino-9-ethyl-5-fluoro-2,3-dihydro-9-hydroxy-4-methyl-1H,12H-benzo-[de]pyrano[3',4':6,7] indolizino[1,2-b]quinoline-10,13(9H,15H)-dione methanesulfonate.

3. A composition having anti-tumor activity comprising an effective amount of the hexa-cyclic compound of claim 1 or 2 in admixture with a pharmaceutically acceptable carrier or excipient.

* * * * *

UNITED STATES PATENT AND TRADEMARK OFFICE
CERTIFICATE OF CORRECTION

PATENT NO. : 5,658,920
DATED : August 19, 1997
INVENTOR(S) : Hirofumi TERASAWA, et al.

It is certified that error appears in the above-indentified patent and that said Letters Patent is hereby corrected as shown below:

On the title page, item [54], and the top of column 1, should read:

SUBSTITUTED 1H,12H-BENZO-[DE]PYRANO[3',4':6,7]INDOLIZINO[1,2-B]QUINOLINE-10,13(9H,15H)- DIONE COMPOUNDS

Signed and Sealed this

Twenty-third Day of December, 1997

Attest:

BRUCE LEHMAN

*Attesting Officer*    *Commissioner of Patents and Trademarks*